(12) United States Patent
Stewart et al.

(10) Patent No.: US 11,866,724 B2
(45) Date of Patent: Jan. 9, 2024

(54) ADENOVIRAL VECTORS

(71) Applicant: Gene Bridges GMBH, Heidelberg (DE)

(72) Inventors: Adrian Francis Stewart, Dresden (DE); Jun Fu, Dresden (DE); Anja Ehrhardt, Witten (DE); Eric Ehrke-Schulz, Witten (DE); Wenli Zhang, Witten (DE)

(73) Assignee: Gene Bridges GMBH, Heidelberg (DE)

( * ) Notice: Subject to any disclaimer, the term of this patent is extended or adjusted under 35 U.S.C. 154(b) by 800 days.

(21) Appl. No.: 16/090,941

(22) PCT Filed: Apr. 6, 2017

(86) PCT No.: PCT/EP2017/058306
§ 371 (c)(1),
(2) Date: Oct. 3, 2018

(87) PCT Pub. No.: WO2017/174753
PCT Pub. Date: Oct. 12, 2017

(65) Prior Publication Data
US 2019/0382793 A1 Dec. 19, 2019

(30) Foreign Application Priority Data
Apr. 6, 2016 (GB) ...................................... 1605903

(51) Int. Cl.
| | | |
|---|---|---|
| C12N 15/86 | (2006.01) | |
| C12N 15/87 | (2006.01) | |
| C12N 7/00 | (2006.01) | |
| C12N 9/22 | (2006.01) | |
| C12N 15/11 | (2006.01) | |

(52) U.S. Cl.
CPC ............... *C12N 15/86* (2013.01); *C12N 7/00* (2013.01); *C12N 9/22* (2013.01); *C12N 15/11* (2013.01); *C12N 2310/20* (2017.05); *C12N 2710/10021* (2013.01); *C12N 2710/10043* (2013.01); *C12N 2800/80* (2013.01)

(58) Field of Classification Search
CPC . C12N 15/86; C12N 7/00; C12N 9/22; C12N 15/11
See application file for complete search history.

(56) References Cited

U.S. PATENT DOCUMENTS 6,140,087 A * 10/2000 Graham ............... C12N 15/86
435/320.1
2002/0102731 A1 8/2002 Hearing et al.
2006/0008884 A1 1/2006 Hearing et al.

FOREIGN PATENT DOCUMENTS

| WO | 2009104094 A2 | 8/2009 | |
|---|---|---|---|
| WO | WO-2011154927 A2 * | 12/2011 | ............. C12N 15/10 |
| WO | 2011154927 A3 | 2/2012 | |
| WO | 2012024351 A2 | 2/2012 | |

OTHER PUBLICATIONS

Zhang, Y., Buchholz, F., Muyrers, J. P., & Stewart, A. F. (1998). A new logic for DNA engineering using recombination in *Escherichia coli*. Nature genetics, 20(2), 123-128. (Year: 1998).*
Zhang, Y., Muyrers, J. P., Testa, G., & Stewart, A. F. (2000). DNA cloning by homologous recombination in *Escherichia coli*. Nature biotechnology, 18(12), 1314-1317. (Year: 2000).*
Muyrers JP, Zhang Y, Buchholz F, Stewart AF. RecE/RecT and Redα/Redβ initiate double-stranded break repair by specifically interacting with their respective partners. Genes & development. Aug. 1, 2000;14(15):1971-82. (Year: 2000).*
Chartier C, Degryse E, Gantzer M, Dieterle A, Pavirani A, Mehtali M. Efficient generation of recombinant adenovirus vectors by homologous recombination in *Escherichia coli*. J Virol. Jul. 1996;70(7):4805-10. doi: 10.1128/JVI.70.7.4805-4810.1996. PMID: 8676512; PMCID: PMC190422. (Year: 1996).*
Takahashi N, Yoshikura H, Kobayashi I. An *Escherichia coli* strain, BJ5183, that shows highly efficient conservative (two-progeny) DNA double-strand break repair of restriction breaks. Gene. Jan. 16, 2003;303:89-97. (Year: 2003).*
Lathe R, Vilotte JL, Clark AJ. Plasmid and bacteriophage vectors for excision of intact inserts. Gene. Jan. 1, 1987;57(2-3):193-201. ( Year: 1987).*
Sørensen HP, Mortensen KK. Advanced genetic strategies for recombinant protein expression in *Escherichia coli*. Journal of biotechnology. Jan. 26, 2005;115(2):113-28. (Year: 2005).*
Fu J, Bian X, Hu S, Wang H, Huang F, Seibert PM, Plaza A, Xia L, Müller R, Stewart AF, Zhang Y. Full-length RecE enhances linear-linear homologous recombination and facilitates direct cloning for bioprospecting. Nature biotechnology. May 2012;30(5):440-6. (Year: 2012).*
He TC, Zhou S, Da Costa LT, Yu J, Kinzler KW, Vogelstein B. A simplified system for generating recombinant adenoviruses. Proceedings of the National Academy of Sciences. Mar. 3, 1998;95(5):2509-14. (Year: 1998).*
O'Hanlon Cohrt, Karen. How to Manipulate Plasmid Copy Number Bite Size Bio: Jan. 14, 2015 (https://bitesizebio.com/profile/karenohanlon/) (Year: 2015).*
Boros I, Pósfai G, Venetianer P. High-copy-number derivatives of the plasmid cloning vector pBR322. Gene. Oct. 1, 1984;30(1-3): 257-60. (Year: 1984).*
Muyrers JP, Zhang Y, Stewart AF. Techniques: recombinogenic engineering-new options for cloning and manipulating DNA. Trends in biochemical sciences. May 1, 2001;26(5):325-31. (Year: 2001).*
Hanahan DO, Gluzman YA. Rescue of functional replication origins from embedded configurations in a plasmid carrying the adenovirus genome. Molecular and cellular biology. Feb. 1984;4(2):302-309. (Year: 1984).*

(Continued)

*Primary Examiner* — Quang Nguyen
(74) *Attorney, Agent, or Firm* — McNeill Baur PLLC

(57) ABSTRACT

The invention relates to adenoviral vectors, cells for use in generating adenoviral vectors, methods for generating adenoviral vectors, and therapeutic uses of adenoviral vectors in gene therapy, tumour therapy and as vaccines.

10 Claims, 27 Drawing Sheets

Specification includes a Sequence Listing.

(56) References Cited

OTHER PUBLICATIONS

GenBank (Gene ID: 945918) "recE Rac prophage; exonuclease VIII, ds DNA exonuclease, 5'→3' specific" and PubMed of internal references; retrieved online on Feb. 16, 2021 (Year: 2021).*
Alignment of amino acid sequence from Gene ID: 945918 with SEQ ID No. 1412 of U.S. Appl. No. 16/090,941 (Year: 2021).*
Danthinne et al.,"Production of first generation adenovirus vectors: a review," Gene Therapy, vol. 7, No. 20, pp. 1707-1714, Jan. 1, 2000.
International Search Report and Written Opinion of PCT/EP2017/058306, dated Sep. 14, 2017 (23 pages).
Aiuti et al., "Lentiviral hematopoietic stem cell gene therapy in patients with Wiskott-Aldrich syndrome," Science 341, 1233151, 14 pages, (2013).
Barnes et al., "Novel adenovirus-based vaccines induce broad and sustained T cell responses to HCV in man," Sci. Transl. Med. 4, 115ra1, 12 pages, (2012).
Barouch et al., "Novel adenovirus vector-based vaccines for HIV-1," Curr. Opin. HIV AIDS 5, pp. 386-390, 8 pages, (2010).
Biffi et al., "Lentiviral hematopoietic stem cell gene therapy benefits metachromatic leukodystrophy," Science 341, 1233158, 14 pages, (2013).
Bradley et al., "Adenovirus serotype 5 neutralizing antibodies target both hexon and fiber following vaccination and natural infection," J. Virol. 86, pp. 625-629, 5 pages, (2012).
Cheong, et al., "E1A-expressing adenoviral E3B mutants act synergistically with chemotherapeutics in immunocompetent tumor models," Cancer Gene Ther. 15, 20 pages, (2008).
Cody et al., "Armed replicating adenoviruses for cancer virotherapy," Cancer Gene Ther. 16, pp. 473-488, 30 pages, (2009).
Cong et al., "Multiplex Genome Engineering using CRISPR/Cas Systems," Science 15, 819-823, 7 pages, (2013).
Crystal, R., "Adenovirus: the first effective in vivo gene delivery vector," Human gene therapy 25, 3-11, 11 pages, (2014).
Davison et al., "Genetic content and evolution of adenoviruses," J. Gen. Virol. 84, 2895-2908, 15 pages, (2003).
Doronin et al., "Chemical modification with high molecular weight polyethylene glycol reduces transduction of hepatocytes and increases efficacy of intravenously delivered oncolytic adenoviruses," Hum. Gene Ther. 20, 975-988, 14 pages, (2009).
Gaggar et al., "CD46 is a cellular receptor for group B adenoviruses," Nat. Med. 9, 1408-1412, 5 pages, (2003).
Geisbert et al., "Recombinant adenovirus serotype 26 (Ad26) and Ad35 vaccine vectors bypass immunity to Ad5 and protect nonhuman primates against Ebolavirus challenge," J. Virol, 85, 4222-4233, 13 pages, (2011).
Ghebremedhin, B, "Human adenovirus: viral pathogen with increasing importance," Eur. J. Microbiol. Immunol. 4, 26-33, 9 pages, (2014).
Green et al., "Extended plasma circulation time and decreased toxicity of polymer-coated adenovirus," Gene Ther. 11, 1256-1263, 9 pages, (2004).
Hage et al., "Human Adenovirus type 70: A novel, multiple recombinant species D adenovirus isolated from diarrheal faeces of a haematopoietic stem cell transplantation recipient," J. Gen. Virol. 96, 2734-2742, 9 pages, (2015).
Hausl et al., "Development of Adenovirus Hybrid Vectors for Sleeping Beauty Transposition in Large Mammals," Curr. Gene Ther. 11, 363-374, 12 pages, (2011).
Kaufman et al., "Oncolytic viruses: a new class of immunotherapy drugs," Nature reviews. Drug discovery 14, 642-662, 22 pages, (2015).
Li et al., "PiggyBac transposase tools for genome engineering," Proc. Nat. Acad. Sci. USA 110, E2279-E2287, 9 pages, (2013).
Mashal et al., "Detection of mutations by cleavage of DNA heteroduplexes with bacteriophage resolvases," Nat. Genet. 9, 177-183, 7 pages, (1995).
Miralles et al., "The Adenovirus Inverted Terminal Repeat Functions as an Enhancer in a Cell-free System," The Journal of Biological Chemistry, vol. 264, No. 18, Issue of Jun. 25, pp. 10763-10772, 1989.
Nathwani et al., "Adenovirus-associated virus vector-mediated gene transfer in hemophilia B," The New England Journal of Medicine 365, 9 pages, (2011).
Kusano et al., "Plasmid-mediated Lethality and Plasmid Multimer Formation in an *Escherichia coli* recBC sbcBC Mutant Involvement of RecF Recombination Pathway Genes," J. Mol. Biol. (1989), 209 pp. 623-634 (12 pages).
Zabner et al., "Adenovirus-mediated gene transfer transiently corrects the chloride transport defect in nasal epithelia of patients with cystic fibrosis," Cell, vol. 75, 207-216 10 pages, (1993).
Penaloza-MacMaster, "Alternative serotype adenovirus vaccine vectors elicit memory T cells with enhanced anamnestic capacity compared to Ad5 vectors," J. Virol. 87, 1373-1384, 14 pages, (2013).
Rauschhuber et al., "RNAi suppressor P19 can be broadly exploited for enhanced adenovirus replication and microRNA knockdown experiments," Sci. rep. 3:1363, 7 pages, (2013).
Rodriguez et al., "Prostate attenuated replication competent adenovirus (ARCA) CN706: a selective cytotoxic for prostate-specific antigen-positive prostate cancer cells," Cancer Res. 57, 2559-2563, 6 pages, (1997).
Salzberg et al., "Microbial gene identification using interpolated Markov models," Nucleic Acids Research vol. 26, No. 2, pp. 544-548, 5 pages, (1998).
Search Report issued in Great Britain Application No. GB1605903.2, dated Feb. 28, 2017, (4 pages).
Slater et al., "Automated generation of heuristics for biological sequence comparison," BMC Bioinformatics 6:31, 11 pages, (2005).
Tuve et al., "A new group B adenovirus receptor is expressed at high levels on human stem and tumor cells," J. Virol. 80, No. 24, pp. 12109-12120, 13 pages, (2006).
Wang, et al., "Desmoglein 2 is a receptor for adenovirus serotypes 3, 7, 11 and 14," Nat. Med. vol. 17, No. 1, 96-105, 11 pages, (2011).
Wang, et al., "Improved seamless mutagenesis by recombineering using ccdB for counterselection.," Nucleic Acids Res. 42, e37, 12 pages, (2014).
Wikipedia, "Plasmid copy number," 3 pages. https://en.wikipedia.org/wiki/Plasmid_copy_number.
Wilson, J. M., "Gendicine: the first commercial gene therapy product," Human gene therapy 16, 1014-1015, 2 pages, (2005).
Wold et al., "Adenovirus vectors for gene therapy, vaccination and cancer gene therapy," Curr. Gene Ther. 13(6), 421-433 26 pages, (2013).
Yamamoto et al., "Current issues and future directions of oncolytic adenoviruses," Mol Ther. vol. 18, No. 2, 243-250, 8 pages, (2010).
Zhang et al., "Adenovirus receptors," J. Virol. 79, No. 19, 12125-12131, 7 pages, (2005).
Zhang et al., DNA cloning by homologous recombination in *Escherichia coli*, Nature biotechnology, 18(12), pp. 1314-1317 (2000).
Hofmayer et al., "Unique Sequence features of the Human Adenovirus 31 complete genomic sequence are conserved in clinical isolates," BMC Genomics, 10:557, Nov. 25, 2009 (14 pages).
Ginn et al., "Gene therapy clinical trials worldwide to 2012—an update," J Gene Med 2013; 15: 65-77 (13 pages).
Harrach, B. et al., "Virus Taxonomy: Classification and Nomenclature of Viruses," Adenoviradae, pp. 125-141 2011, (19 pages).
Jin et al., "Research Progress of Adenovirus and Its Vector," Journal of Tianjin Agriculture University, Jun. 2007, 14 (2): 48-51 (4 pages).
Li et al., "Construction of recombinant adenoviral vector by a simple, cheap, and high performance method," JTMU, 2005 11(2): 171-174 (4 pages).
Zhongbo et al., "A Method for Production and Manipulation of Recombinant Adenovirus Vector," J Huazhong Univ Sci Tech, vol. 32, No. 4, Aug. 2003 (4 pages).
English Translation of First Office Action issued in Chinese Application No. 20178003095.2, dated May 6, 2022 (23 pages).
Gao et al., "State-of-the-art human adenovirus vectorology for therapeutic approaches," FEBS Letters, 593, pp. 3609-3622, Dec. 2019 (14 pages).

(56) References Cited

OTHER PUBLICATIONS

Lu, Q., "Seamless cloning and gene fusion," Trends in Biotechnology, vol. 23, No. 4, pp. 199-207, Apr. 2005 (9 pages).

* cited by examiner

FIGURE 12
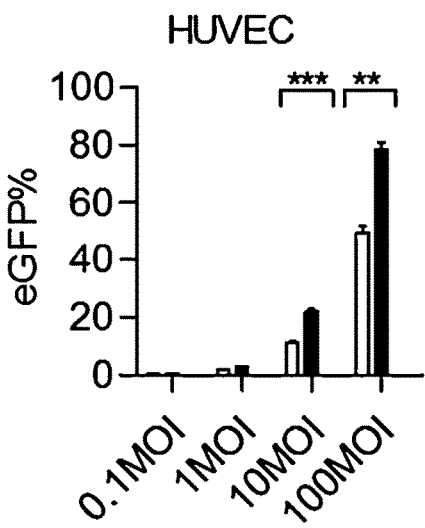
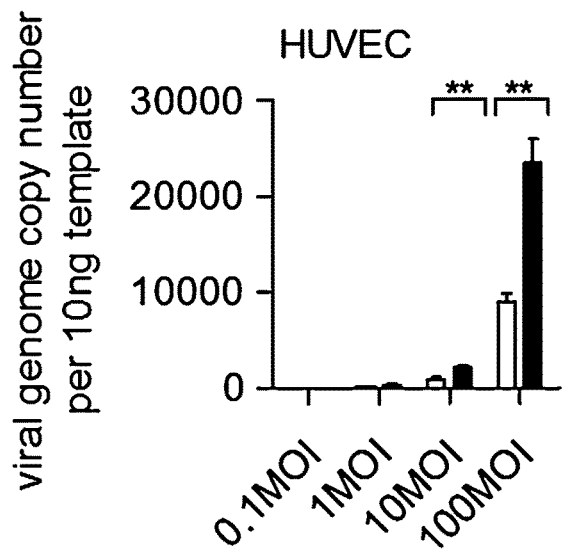
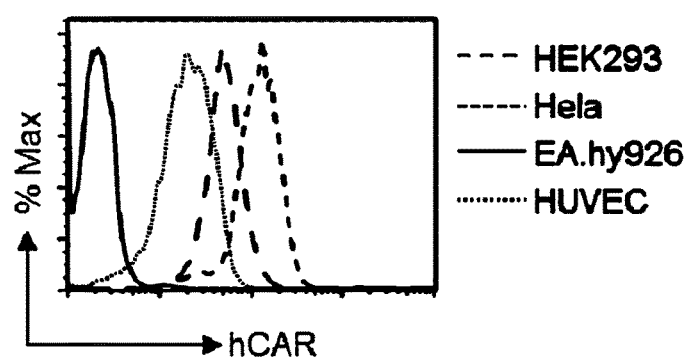
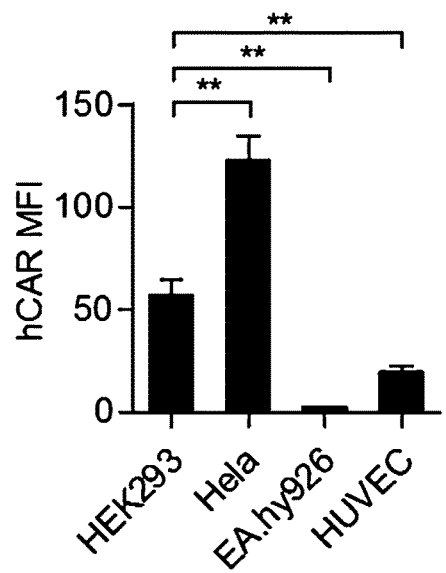

pHAdV17E1-IRES-neo

Methylene blue staining after G418 selection

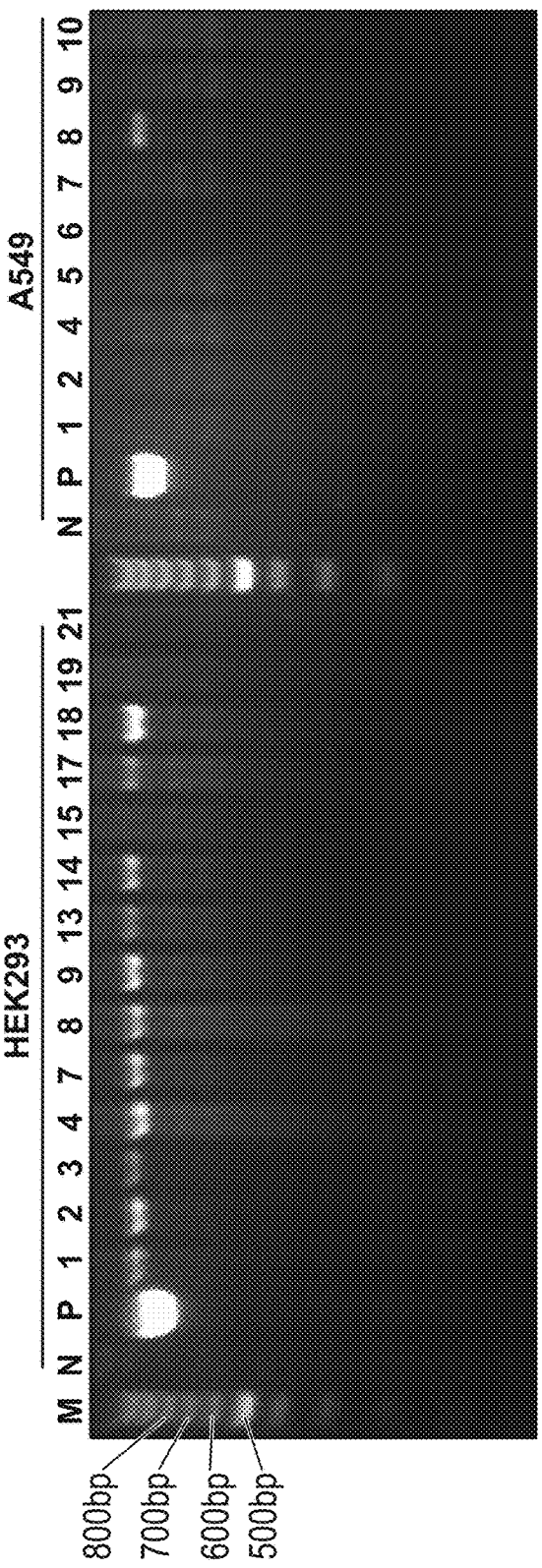
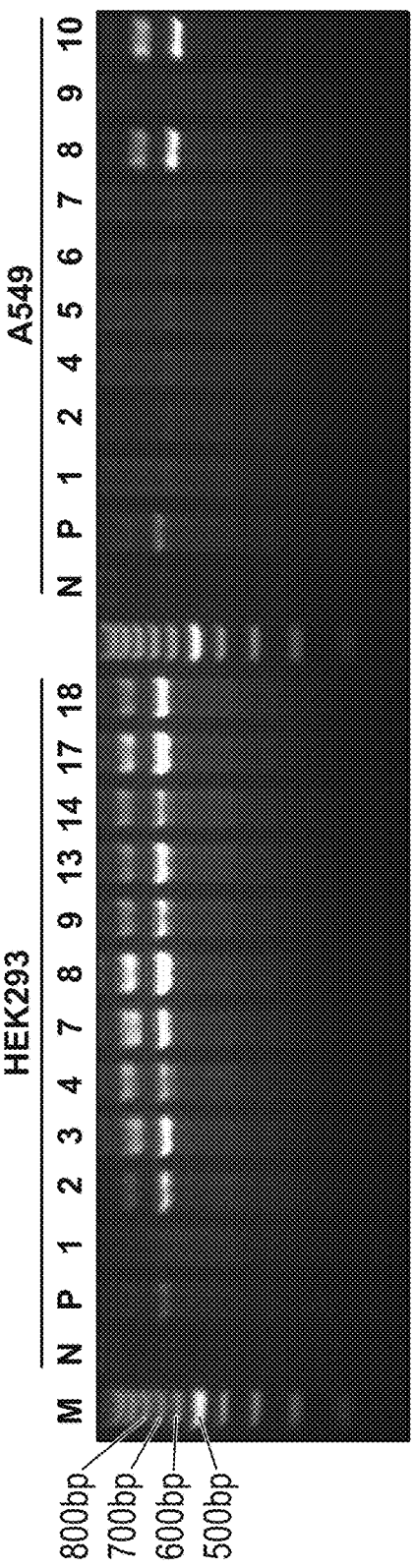
FIGURE 18C

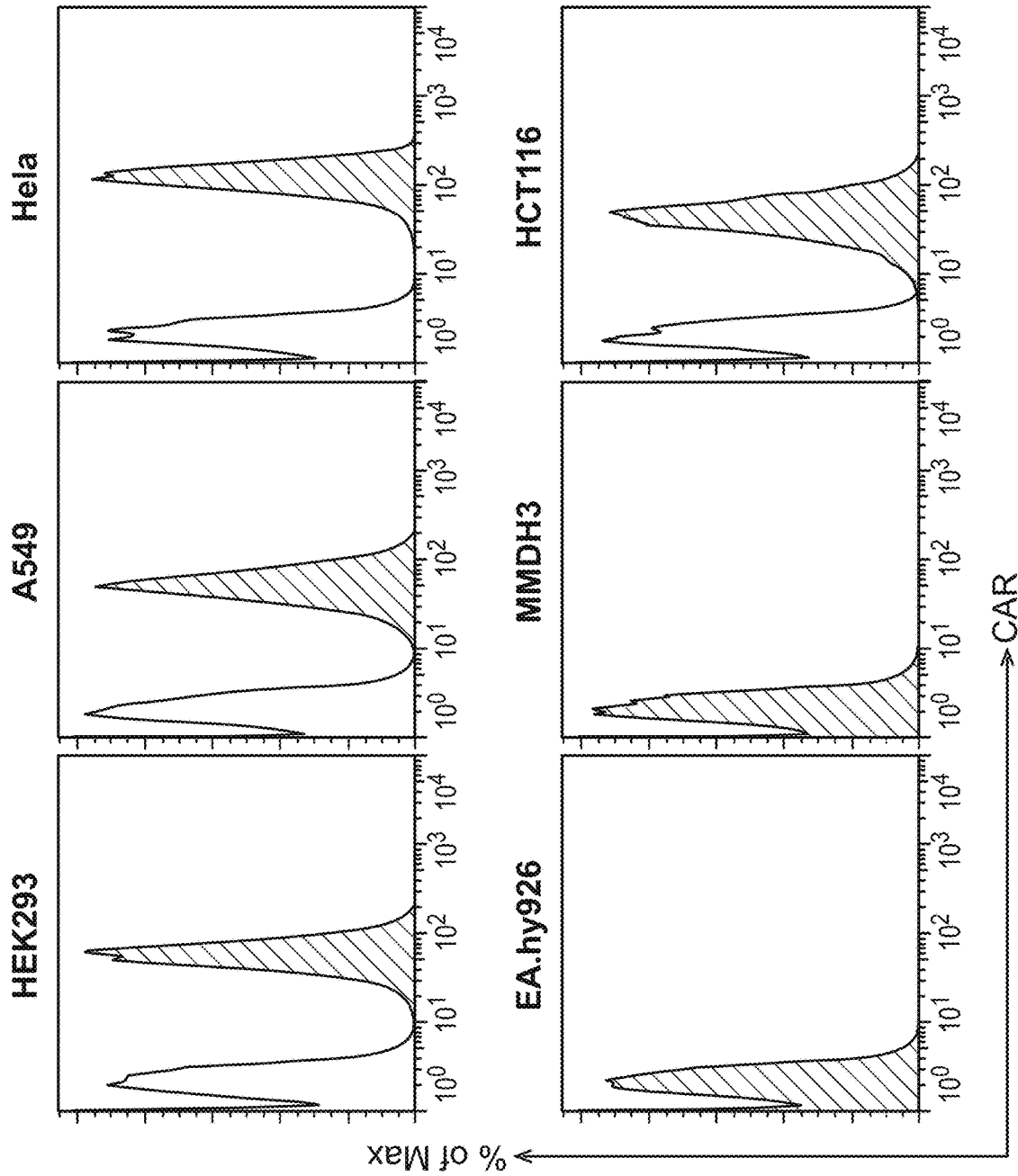

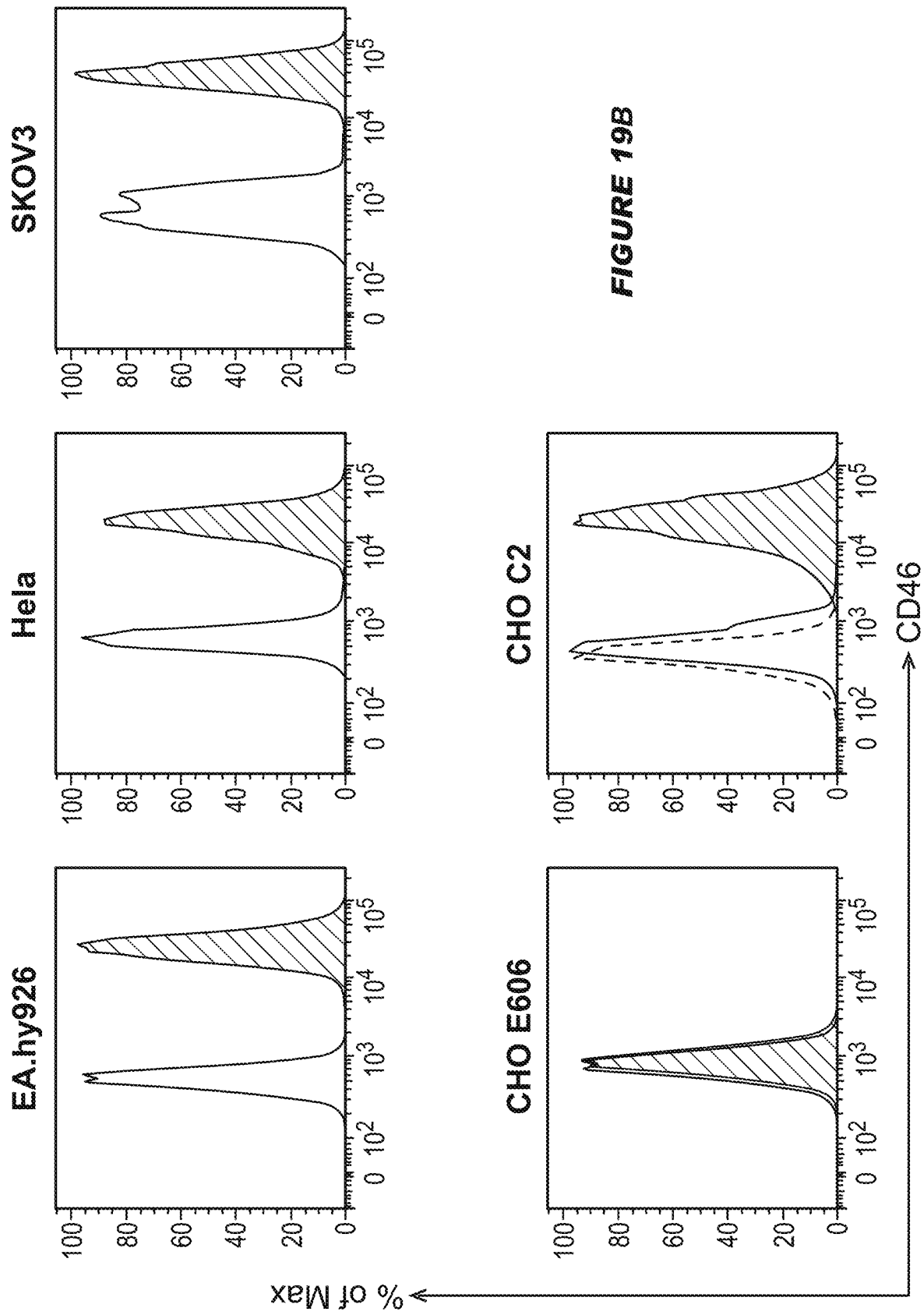

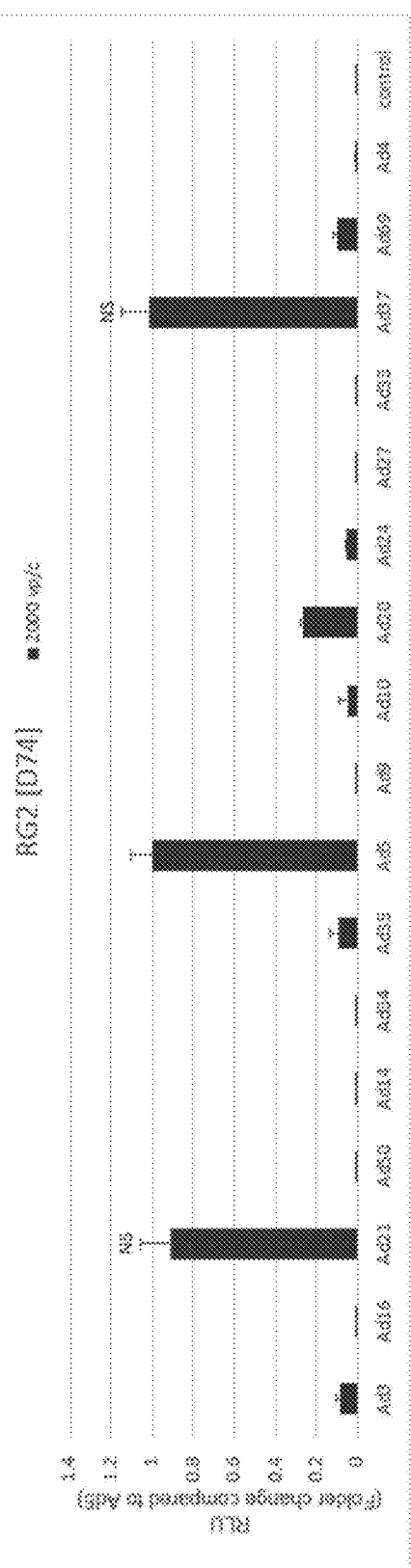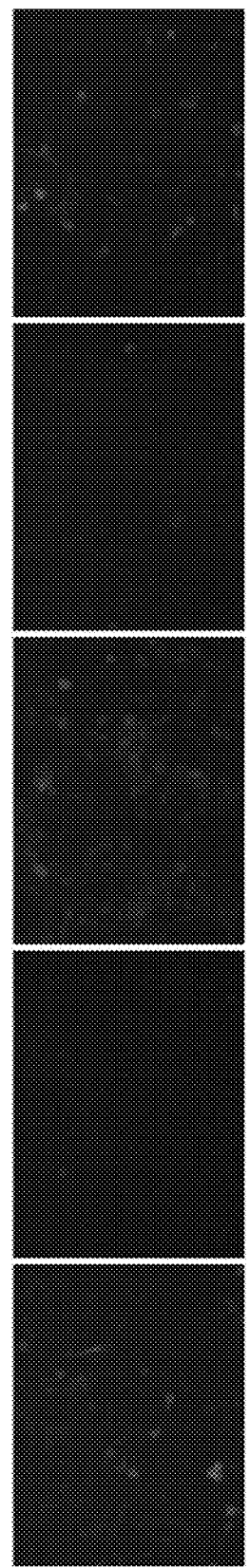
FIGURE 23

ADENOVIRAL VECTORS

CROSS-REFERENCE TO RELATED APPLICATIONS

This application is a national phase entry pursuant to 35U.S.C. § 371 of International Application No. PCT/EP2017/058306, filed Apr. 6, 2017, which claims the benefit of priority of Great Britain Application No. 1605903.2, filed Apr. 6, 2016, each of which is incorporated by reference herein in its entirety for any purpose.

SEQUENCE LISTING

The present application includes a Sequence Listing in electronic format. The Sequence Listing is provided as a file entitled "2021-12-03_01169-0014-00US_Seq_List_ST25.txt" created on Dec. 3, 2021, which is 3,576,078 bytes in size. The information in the electronic format of the sequence listing is incorporated herein by reference in its entirety.

FIELD OF THE INVENTION

The invention relates to adenoviral vectors, cells for use in generating adenoviral vectors, methods for generating adenoviral vectors, and therapeutic uses of adenoviral vectors in gene therapy, tumour therapy and as vaccines.

BACKGROUND TO THE INVENTION

Adenoviruses (Ad) are non-enveloped dsDNA viruses, typically 26-46 kb in length, flanked by inverted terminal repeats (ITR) at both ends. An increasing number of human and nonhuman Ad types are being identified. Besides the fact that adenoviruses are emerging pathogens in immunocompromised patients, they represent the most frequently used vector type for tumour therapy, gene therapeutic approaches and vaccination studies, largely owing to their robust gene delivery efficiencies and the ability to transduce a broad variety of cell types. However, exploration of the complete natural adenovirus diversity for broad applications has been absent because an efficient high throughput cloning (HTC) system has been lacking.

In recent years, adenoviruses have received increasing attention both as human and veterinary pathogens and as emerging therapeutics. As pathogens, adenoviruses cause a multitude of infections with growing numbers of fatalities. An effective treatment is lacking and lethality in immunocompromised patients amounts to 70%. As therapeutics, adenoviruses belong to the currently most promising candidates in the group of advanced-therapy medicinal products (ATMPs), with high potential for the treatment of malignant tumours as oncolytic viruses, as genetic vaccines against infectious diseases, and as gene transfer vectors for gene therapy applications. Increasing numbers of novel adenovirus types are being identified and it has become clear that adenoviruses comprise an enormous natural diversity of several hundred entities. However, most scientific knowledge on the virology of adenoviruses is based on a very small number of human type C adenoviruses, in particular human adenovirus 5 (HAdV-C5), despite the fact that the sequence diversity of the many adenovirus types is reflected in differences in their biology (e.g. tropism, infectious cycle, host interaction, persistence, immune evasion) and also in their virulence. Similarly, HAdV-C5 has served for many clinical tumour and gene therapy applications despite there being evidence that its therapeutic efficacy is strongly limited.

Gene therapy is an emerging field where therapeutic nucleic acids are delivered into target cells of interest. Recent success stories include the treatment of rare genetic diseases such as Wiskott-Aldrich syndrome[1], hemophilia B[2], and metachromatic leukodystrophy[3]. Adenovirus-based vectors represent the most frequently used vector types worldwide[4,5] for tumour therapy, gene therapeutic approaches, and vaccination studies, largely owing to their robust gene delivery properties and the ability to transduce a broad variety of cell types. First clinical trials utilising recombinant adenovirus for cystic fibrosis were initiated in 1993[6]. Adenoviral vectors gained global attention as a gene therapeutic agent when Gendicine was approved by the Chinese food and drug administration in 2003 for treatment of head and neck cancers[7]. Another option to treat malignancies is the use of tumour-specific replication competent adenoviruses for oncolytic virotherapy. In combination with chemotherapies and with further improvements, biologicals such as oncolytic viruses are being evaluated in clinical trials, which are likely to herald a growing repertoire of applications[8].

Although ~70 types of human Ad and numerous nonhuman Ad (>200) have been identified so far, a system for efficient Ad genome cloning and manipulation has been lacking. Previous studies have suggested using homologous recombination based techniques to clone adenoviral genomes into plasmids (Chartier, C. et al. (1996) *Efficient generation of recombinant adenovirus vectors by homologous recombination in Escherichia coli*. J. Virol. 70, 4805-4810; Renaut, L. et al. (2002) *A rapid and easy method for production and selection of recombinant adenovirus genomes*. J Virol Methods 100, 121-31). However, the homologous recombination in the bacterial strains used in these studies is highly inefficient, and these systems therefore require long homology arms and pure concentrated forms of adenoviral DNA. Accordingly, the majority of recombinant adenoviral vectors (AdVs) are still based on only a small fraction of Ad types and their variants[9,10,13]. However, predefined tissue tropism and pre-existing immunity considerably limit their applications. Limitations of vectors and oncolytic viruses based on HAd5 include cell tropism and pre-existing immunity in the human population against HAd5. HAd5 has a strong liver tropism in mice, as well as in humans when delivered intravenously, which is associated with a high innate immunity toxicity profile and sequestration of virus in the liver. The high seroprevalence of HAd5 in the human population results in induction of robust adaptive immune responses against vectors and oncolytic viruses based on this serotype, which hinder their effectiveness. Immune responses and liver sequestration of such vectors and viruses also mean that high doses are often administered to circumvent these problems, risking liver injury and inflammatory shock syndrome.

The present invention addresses the problems of pre-existing immunity and limited cell tropism of existing adenovirus vectors and oncolytic adenoviruses. By providing a novel engineered library of human adenoviral genomes, the inventors have facilitated the development of a vast repertoire of new adenoviral vectors and oncolytic viruses that can be used greatly to expand the range of possible applications, with the potential to improve therapeutic efficacy.

SUMMARY OF THE INVENTION

The present invention is based on the generation of a novel engineered full-genome, type-specific human adenovirus (HAdV) library made through novel recombineering technologies. This library provides the tools for arbitrary genetic modification of viral genomes and allows the generation of new adenoviral vectors, vaccines and oncolytic viruses, for example with improved efficacy and safety.

The inventors have established that adenoviral genomes can be high-throughput cloned (HTC) and tagged by using advanced linear-linear homologous recombination (LLHR) and linear-circular homologous recombination (LCHR) techniques[11,12]. Wild-type Ad from clinical isolates, including around half of the currently known adenovirus types, were propagated and direct high throughput cloning applied. The integrity of cloned Ad genomes was confirmed by DNA restriction pattern and virus reconstitution, and next-generation sequencing (NGS) and phylogenetic analysis was performed. The recombinant TurboGFP fluorescent/NanoLuc luciferase double reporter-marked AdVs facilitate vector characterisation and in vivo imaging. This new engineered adenoviral library will facilitate broader applications in molecular medicine including gene therapy and vaccination studies, as well as basic virology. The library of cloned genomes provided by the inventors facilitates generation of various vector types, genetic modification, insertion of transgenes, and tagging with reporter genes of adenoviruses of various different serotypes, using the methods disclosed herein. Such a system for straightforward manipulation of adenoviral genomes has been lacking.

The library provides for an improved scientific understanding of viral and host factors that determine the type-specific interactions of adenoviruses with their host, e.g. as regards tissue tropism, virus persistence, pathogenesis and virulence, and those factors essential to address potential risks associated with newly evolving adenoviruses. This library can also be used to screen for potential new drug targets for anti-adenoviral therapeutic strategies.

In one aspect, the invention provides adenoviral vectors with sequences derived from the newly-cloned adenoviral genomes in the library. Vectors comprising these novel sequences have various advantages of therapeutic potential, including altered cell tropisms relative to HAdV5-based vectors, so facilitating the targeting of different cell types, and/or the avoidance of pre-existing immunity against the HAdV5 serotype. For example, in one embodiment, the invention provides an adenoviral vector comprising a sequence derived from an adenoviral genome sequence contained within any one of SEQ ID Nos 1-32 and/or 1411, for example, contained within any one of SEQ ID Nos 1-15, 17-32 and/or 1411 or contained within any one of SEQ ID NOs: 1-3, 5-8, 10-12, 14-15, 17-25 and 27-32 and/or 1411, or contained within any one of SEQ ID NOs: 1-3, 5-8, 10-12, 14-15, 17-25 and 27-32, or a sequence at least 50% identical thereto. In another embodiment, the invention provides an adenoviral vector comprising the full adenoviral genome sequence contained within any one of SEQ ID Nos 1-32 and/or 1411, for example, contained within any one of SEQ ID Nos 1-15 and 17-32 and/or 1411 or contained within SEQ ID NOs: 1-3, 5-8, 10-12, 14-15, 17-25 and 27-32 and/or 1411, or contained within any one of SEQ ID NOs: 1-3, 5-8, 10-12, 14-15, 17-25 and 27-32, or a sequence at least 50% identical thereto. Preferably, the degree of sequence identity is at least 60%, 70%, 80%, 85%, 90%, 95%, 96%, 97%, 98%, 99%, 99.5% or 99.9%.

In another embodiment, the adenoviral vector lacks the E1 region. For example, in some embodiments, the invention provides an adenoviral vector comprising the adenoviral genome sequence contained within any one of the sequences listed in SEQ ID Nos 1-32 and/or 1411, for example, contained within any one of SEQ ID Nos 1-15 and 17-32 and/or 1411, or contained within any one of SEQ ID NOs: 1-3, 5-8, 10-12, 14-15, 17-25 and 27-32 and/or 1411, or a sequence at least 50% identical thereto, that lacks the E1 region. In one embodiment, the invention provides an adenoviral vector comprising a sequence selected from SEQ ID NOs: 1-3, 5-8, 10-12, 14-15, 17-25 and 27-32, or a sequence at least 50% identical thereto, that lacks the E1 region. Preferably, the degree of sequence identity is at least 60%, 70%, 80%, 85%, 90%, 95%, 96%, 97%, 98%, 99%, 99.5% or 99.9%.

In another embodiment, the adenoviral vector lacks the E1 region and the E3 region. For example, in some embodiments, the invention provides an adenoviral vector comprising the adenoviral genome sequence contained within any one of the sequences listed in SEQ ID Nos 1-32 and/or 1411, for example, contained within any one of SEQ ID Nos 1-15 and 17-32 and/or 1411 or contained within any one of SEQ ID NOs:1-8, 10-12, 14-15 and 17-32 and/or 1411, or a sequence at least 50% identical thereto, that lacks the E1 region and the E3 region. In another embodiment, the invention provides an adenoviral vector comprising a sequence selected from SEQ ID NOs:1-8, 10-12, 14-15 and 17-32, or a sequence at least 50% identical thereto, that lacks the E1 region and the E3 region. Preferably, the degree of sequence identity is at least 60%, 70%, 80%, 85%, 90%, 95%, 96%, 97%, 98%, 99%, 99.5% or 99.9%.

In another embodiment, the adenoviral vector lacks the E3 region. For example, in some embodiments, the invention provides an adenoviral vector comprising the adenoviral genome sequence contained within any one of the sequences listed in SEQ ID Nos 1-32 and/or 1411, for example, contained within any one of SEQ ID Nos 1-15 and 17-32 and/or 1411 or contained within any one of SEQ ID NOs: 1-3, 5-12, 14-15 and 17-32 and/or 1411, or a sequence at least 50% identical thereto, that lacks the E3 region. In another embodiment, the invention provides an adenoviral vector comprising a sequence selected from SEQ ID NOs: 1-3, 5-12, 14-15 and 17-32, or a sequence at least 50% identical thereto, that lacks the E3 region. Preferably, the degree of sequence identity is at least 60%, 70%, 80%, 85%, 90%, 95%, 96%, 97%, 98%, 99%, 99.5% or 99.9%.

In another embodiment, the invention provides a library of adenoviral vectors comprising at least 2 (for example, at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, or 33) of the adenovirus genome sequences described in SEQ ID NOs 1-32 and 1411, for example, of the adenovirus genome sequences described in SEQ ID NOs: 1-3, 5-8, 10-12, 14-15, 17-25 and 27-32 and/or 1411, and/or the other adenoviral vectors described herein. In some embodiments these adenoviral sequences are contained within a plasmid backbone.

In another embodiment, the invention provides an adenoviral vector comprising the 5' and 3' inverted terminal repeat (ITR) sequences from an adenoviral genome sequence disclosed herein. Preferably the 5' and 3' ITR regions are taken from the same adenoviral genome and are present at the 5' end and the 3' end, respectively, of the vector. Such vectors are used in conjunction with an adenovirus helper vector according to the invention. For example, in some embodiments, the invention provides an adenoviral vector comprising the 5' ITR sequence contained within any one of the sequences listed in SEQ ID Nos 1-32 and/or 1411, or a sequence at least 80% identical to the 5' ITR sequence, at the 5' end, and comprising the 3' ITR sequence contained within any one of the sequences listed in SEQ ID Nos 1-32 and/or 1411, or a sequence at least 80% identical to the 3' ITR sequence, at the 3' end. For example, in some embodiments, the invention provides an adenoviral vector comprising the 5' ITR sequence contained within any one of the sequences listed in SEQ ID Nos 1-15 and 17-32 and/or 1411 or contained within any one of SEQ ID NOs: 1-13 and 18-32 and/or 1411, or a sequence at least 80% identical to the 5' ITR sequence, at the 5' end, and comprising the 3' ITR sequence contained within any one of the sequences listed in SEQ ID Nos 1-15 and 17-32 and/or 1411 or contained within any one of SEQ ID NO: 1-13 and 18-32 and/or 1411, or a sequence at least 80% identical to the 3' ITR sequence, at the 3' end. For example, in some embodiments, the invention provides an adenoviral vector comprising a sequence selected from the sequences contained within any one of SEQ ID Nos 1-32 and/or 1411 at the positions defined in Table 1 column 4 or a sequence at least 80% identical thereto, at the 5' end, and at the positions defined in Table 1, column 5, or a sequence at least 80% identical thereto, at the 3' end. In some such embodiments, the invention provides an adenoviral vector comprising a sequence selected from the sequences contained within any one of SEQ ID Nos 1-15 and 17-32 and/or 1411 or contained within any one of SEQ ID NO: 1-13 and 18-32 and/or 1411 at the positions defined in Table 1, column 4 or a sequence at least 80% identical thereto, at the 5' end, and at the positions defined in Table 1, column 5, or a sequence at least 80% identical thereto, at the 3' end.

TABLE 1

Positions of inverted terminal repeats (ITRs) in genome sequences

| Adeno-virus | Genome SEQ ID NO | Positioning in genome sequence | | |
| --- | --- | --- | --- | --- |
| | | 5'ITR | 5'ITR + packaging signal | 3' ITR |
| A12 | 1 | 120-280 | 120-619 | 34095-34255 |
| A18 | 2 | 122-288 | 122-621 | 34088-34254 |
| A31 | 3 | 122-271 | 122-621 | 33777-33925 |
| B3 | 4 | 8-143 | 8-507 | 35214-35350 |
| B7 | 5 | 141-276 | 141-640 | 35210-35445 |
| B16 | 6 | 9-122 | 9-508 | 35418-35530 |
| B21 | 7 | 120-231 | 120-619 | 35423-35534 |
| B50 | 8 | 120-233 | 120-619 | 35392-35505 |
| B11 | 9 | 122-223 | 122-621 | 34816-35298 |
| B14a | 10 | 60-196 | 60-559 | 32328-32464 |
| B14b | 11 | 120-256 | 120-619 | 34747-34879 |
| B34 | 12 | 258-394 | 258-757 | 34896-35032 |
| B35 | 13 | 108-244 | 108-607 | 34761-34897 |
| C1 | 14 | 9-111 | 9-508 | 35906-36008 |
| C2 | 15 | 8-110 | 8-507 | 35842-35944 |
| C5 | 16 | 9-111 | 9-508 | 35840-35942 |
| C6 | 17 | 10-111 | 10-509 | 35667-35767 |
| D8 | 18 | 1-130 | 1-500 | 31390-31514 |
| D9 | 19 | 278-436 | 278-777 | 35044-35204 |
| D10 | 20 | 1-148 | 1-500 | 34938-35085 |
| D13 | 21 | 1-145 | 1-500 | 35062-35217 |
| D17 | 22 | 1-146 | 1-500 | 34998-35136 |
| D20 | 23 | 1-145 | 1-500 | 35031-35177 |
| D24 | 24 | 1-146 | 1-500 | 35580-35727 |
| D25 | 25 | 1-146 | 1-500 | 35105-35249 |
| D26 | 26 | 1-146 | 1-500 | 34987-35132 |
| D27 | 27 | 1-158 | 1-500 | 35000-35145 |
| D33 | 28 | 1-146 | 1-500 | 34966-35121 |
| D37 | 29 | 1-159 | 1-500 | 35056-35214 |
| D69 | 30 | 1-148 | 1-500 | 35001-35148 |
| E4 | 31 | 1-116 | 1-500 | 35877-35992 |
| G52 | 32 | 120-170 | 120-619 | 34885-34943 |
| F41 | 1411 | 1-155 | 1-500 | 34032-34189 |

In another embodiment, the invention provides an adenoviral vector comprising a sequence selected from SEQ ID NOs:33-45 and 50-64, or a sequence at least 80% identical thereto, at the 5' end, and a sequence selected from SEQ ID NOs:97-109 and 114-128, or a sequence at least 80% identical thereto, at the 3' end. Such vectors are used in conjunction with an adenovirus helper vector according to the invention. For example, in one embodiment, the invention provides an adenoviral vector comprising the sequence provided in Table 3, column 2 (headed "500 bp 5' UTR") of an adenovirus selected from B3, B16, C1, C2, C5, C6, D10, D13, D20, D24, D25, D26, D27, D33, D37, D69 and E4, or a sequence at least 80% identical thereto, at the 5' end, and comprising the sequence provided in Table 3, column 4 (headed "150 bp 3' ITR") of an adenovirus selected from B3, B16, C1, C2, C5, C6, D10, D13, D20, D24, D25, D26, D27, D33, D37, D69 and E4, or a sequence at least 80% identical thereto, at the 3' end. Preferably, the 5' and 3' sequences are derived from the same adenovirus.

In a further embodiment, the invention provides an adenoviral vector comprising a fiber gene from a genome sequence provided herein. For example, the invention provides an adenoviral vector comprising a fiber gene selected from any one of SEQ ID NOs 129-160 and 1443, for example, any one of SEQ ID NOs 129-160, or a sequence at least 70% identical thereto. In a further embodiment, the invention provides an adenoviral vector comprising a fiber gene selected from SEQ ID NOs:130-131, 135, 138-140, 142, 145-146, 149, 151, 153, 155 and 158-160, or a sequence at least 70% identical thereto. In some embodiments, the adenoviral vector does not contain any regions coding for adenoviral proteins other than these fiber proteins. The invention also provides adenoviral helper vectors with the same features.

The vector may further or alternatively comprise a penton gene selected from any one of SEQ ID NOs 161-192 and 1426, for example, any one of SEQ ID NOs: 161-192, for example selected from SEQ ID NOs:161-175 and 177-192, or a sequence at least 70% identical thereto, and/or a hexon gene selected from any one of SEQ ID NOs 193-224 and 1431, for example, any one of SEQ ID NOs:193-224, for example, selected from SEQ ID NOs:193-207 and 209-224, or a sequence at least 70% identical thereto.

The adenoviral vectors of the invention may be used as adenoviral vaccine vectors comprising a gene encoding an antigen, for example from human immunodeficiency virus (HIV), Ebolavirus, Zika virus, hepatitis B virus, hepatitis C virus, influenza virus, *Mycobacterium tuberculosis*, or *Plasmodium falciparum*.

The invention also provides an adenoviral helper vector comprising the adenoviral genome sequence contained within any one of SEQ ID NOs:1-32 and/or 1411, for example, contained within any one of SEQ ID NOs: 1-13 and 18-32 and 1411 or contained within any one of SEQ ID NOs: 1-13 and 18-32, or a sequence at least 50% identical thereto, that lacks the E1 region and comprises loxP sites (SEQ ID NO:221) or FRT sites (SEQ ID NO:222), wherein the loxP or FRT sites are positioned such that the first is downstream of the part of the sequence corresponding to the 5'ITR and upstream of the packaging signal (Table 1, column 4), and the second is upstream of the position of the deleted E1 region and downstream of the part of the sequence corresponding to the 5'ITR and packaging signal (Table 1, column 4).

The invention also provides an adenoviral helper vector comprising a sequence selected from SEQ ID NOs:1-13 and 18-32, or a sequence at least 50% identical thereto, that lacks the E1 region and comprises loxP sites (SEQ ID NO:221) or FRT sites (SEQ ID NO:222), wherein the loxP or FRT sites are positioned such that the first is downstream of the part of the sequence corresponding to SEQ ID NOs:65-77 and 82-96, respectively, and the second is upstream of the position of the deleted E1 region and downstream of the part of the sequence corresponding to SEQ ID NOs:33-45 and 50-64, respectively.

The invention also provides a cell encoding, and capable of expressing, an adenoviral E1 region contained within any one of SEQ ID Nos 1-32 and/or 1411, or a sequence at least 70% identical to said E1 region. In some embodiments, the invention provides a cell encoding, and capable of expressing, an adenoviral E1 region selected from within any one of SEQ ID NOs: 1-3, 5-8, 10-12, 14-15, 17-25, 27-32 and 1411, for example, selected from SEQ ID NOs: 1-3, 5-8, 10-12, 14-15, 17-25 or 27-32, or a sequence at least 70% identical to said E1 region. The cell may further express Cre recombinase or Flp recombinase. Such cells are used for producing adenovirus vectors according to the invention.

In another embodiment, the invention provides an oncolytic adenoviral vector comprising an E1 region selected from SEQ ID NOs 1-32 and 1411, for example, selected from SEQ ID NOs:1-8, 10-12, 14-15, 18-25, 27-32 or 1411, or for example selected from SEQ ID NOs:1-8, 10-12, 14-15, 18-25 or 27-32, or a sequence at least 70% identical to said E1 region. The oncolytic vector may further comprise:
a) an E2 region derived from SEQ ID NOs 1-32 and 1411, for example selected from SEQ ID NOs:1-8, 10-12, 14-15, 18-25, 27-32 or 1411, or for example selected from SEQ ID NOs:1-8, 10-12, 14-15, 18-25 or 27-32, or a sequence at least 70% identical to said E2 region;
b) an E4 region derived from SEQ ID NOs 1-32 and 1411, for example selected from SEQ ID NOs:1-8, 10-12, 14-15, 18-25, 27-32 or 1411, or for example selected from SEQ ID NOs:1-8, 10-12, 14-15, 18-25 or 27-32, or a sequence at least 70% identical to said E4 region;
c) an L1 region derived from SEQ ID NOs 1-32 and 1411, for example selected from SEQ ID NOs:1-8, 10-12, 14-15, 18-25, 27-32 or 1411, or for example selected from SEQ ID NOs:1-8, 10-12, 14-15, 18-25 or 27-32, or a sequence at least 70% identical to said L1 region;
d) an L2 region derived from SEQ ID NOs 1-32 and 1411, for example selected from SEQ ID NOs:1-8, 10-12, 14-15, 18-25, 27-32 or 1411, or for example selected from SEQ ID NOs:1-8, 10-12, 14-15, 18-25 or 27-32, or a sequence at least 70% identical to said L2 region;
e) an L3 region derived from SEQ ID NOs 1-32 and 1411, for example selected from SEQ ID NOs:1-8, 10-12, 14-15, 18-25, 27-32 or 1411, or for example selected from SEQ ID NOs:1-8, 10-12, 14-15, 18-25 or 27-32, or a sequence at least 70% identical to said L3 region;
f) an L4 region derived from SEQ ID NOs 1-32 and 1411, for example selected from SEQ ID NOs:1-8, 10-12, 14-15, 18-25, 27-32 or 1411, or for example selected from SEQ ID NOs:1-8, 10-12, 14-15, 18-25 or 27-32, or a sequence at least 70% identical to said L4 region; and
g) an L5 region derived from SEQ ID NOs 1-32 and 1411, for example selected from SEQ ID NOs:1-8, 10-12, 14-15, 18-25, 27-32 or 1411, or for example selected from SEQ ID NOs:1-8, 10-12, 14-15, 18-25 or 27-32, or a sequence at least 70% identical to said L5 region.

The E1 and/or E2 region of the oncolytic vector may be mutated or partially deleted to enhance replication activity and/or tumour specificity.

In embodiments in which the vectors comprise multiple different regions, these multiple regions may be derived from the same adenovirus genome or from different adenoviral genomes.

The oncolytic adenoviral vectors of the invention may further comprise:
a) a gene that enhances replication;
b) an immune-modulatory transgene;
c) a suicide gene or an interfering nucleic acid that enhances cell killing;
d) a gene or interfering nucleic acid that renders cells more sensitive to apoptosis or therapy with other drugs;
e) a tumour- or tissue-selective promoter; and/or
f) a gene for modulation of the tumour microenvironment.

The adenoviral vectors of the invention may be used in therapy. The invention also provides a method of treatment comprising administering an adenoviral vector of the invention to a patient. In some embodiments, the adenoviral vector comprises a transgene. In some embodiments, the invention comprises treating cancer comprising administering an adenoviral vector as described herein that is oncolytic for cells of the cancer.

The invention also provides a method of generating an adenoviral vector or helper vector, a cell, or an oncolytic adenoviral vector as defined above.

The invention further provides a method of inserting one or more transgenes into an adenoviral vector or helper vector or an oncolytic adenoviral vector according to the invention.

The invention also provides an adenoviral genome sequence selected from within any one of SEQ ID NOs 1-32 and 1411, for example, selected from within any one of SEQ ID NOs:1-3, 5-12, 14-15, 17-32 and 1411, or selected from within any one of SEQ ID NOs:1-3, 5-12, 14-15 and 17-32, comprising one or more reporter genes and means for their expression, replacing part or all of the E3 region. For example, the invention provides an adenoviral sequence selected from SEQ ID NOs:1-3, 5-12, 14-15 and 17-32, comprising one or more reporter genes and means for their expression, replacing part or all of the E3 region. Vectors comprising such sequences are also provided.

The invention also provides a method of screening for anti-adenoviral drugs, comprising:
a) infecting a cell with a vector comprising the adenoviral sequence within any one of the sequences selected from SEQ ID NOs: 1-3, 5-12, 14-15 and 17-32, comprising one or more reporter genes, and means for their expression, replacing part or all of the E3 region, in the presence and in the absence of a drug of interest;
b) detecting the expression level of the reporter gene product in the presence and in the absence of the drug; and
c) comparing the expression level of the reporter gene product in the presence and in the absence of the drug.

Definitions

In order to facilitate the understanding of the present description, the meaning of some terms and expressions in the context of the invention will be explained below. Further definitions will be included throughout the description as necessary.

"Sequence identity" as defined herein means sequence identity determined by the Smith-Waterman homology search algorithm as implemented in MPSRCH program (Oxford Molecular) using an affine gap search with parameters: gap penalty 10, gap extension penalty 0.5.

The term "high-capacity adenoviral vector" refers to an adenoviral vector that comprises only non-coding adenoviral sequences, and lacks all adenoviral coding regions.

"First generation adenoviral vector" refers to an adenoviral vector lacking the E1 and/or E3 regions.

An "adenoviral helper vector" is an adenoviral vector which provides the required early and late proteins necessary for replication, and is used in conjunction with high-capacity or "helper-dependent" vectors to allow their construction and propagation.

The term "transgene" refers to a gene or genetic material from a heterologous organism or virus. A transgene inserted into an adenoviral vector or oncolytic adenovirus will be a gene that is not derived from that particular adenovirus. The gene may be derived from any other organism or virus.

The term "expression cassette" (in relation to a transgene or antigen) refers to the transgene or antigen to be expressed, in conjunction with means for its expression (e.g. a promoter).

The term "antigen" in the present disclosure refers to an immunogenic protein that is not endogenous to the adenovirus of interest, i.e. it is encoded by a transgene derived from a heterologous organism or virus.

The term "immunomodulatory" refers to the inhibition or reduction of one or more biological activities of the immune system and includes, but is not limited to, downregulation of immune responses and inflammatory states as well as changes in cytokine profile, cytotoxic activity and antibody production.

The term "therapy" or "treatment" refers to treatment of a disease or disease pathology, and includes both therapeutic and prophylactic treatment. The term is not limited to curative treatment and covers any beneficial effect on disease processes (e.g. reducing the risk of, slowing, halting or reversing a disease process).

The term "about" refers to a range of ±10% of the stated value.

The term "comprising" encompasses "including" as well as "consisting" e.g. a composition "comprising" X may consist exclusively of X or may include something additional e.g. X+Y.

Where the invention refers to a sequence that has at least X % sequence identity with another sequence, in alternative embodiments, the invention further comprises sequences having a higher level of sequence identity with that sequence. For example, if a sequence is said to have at least 50% sequence identity with another sequence, then in alternative embodiments, a sequence having at least 55%, 60%, 65%, 70%, 75%, 80%, 85%, 90%, 95%, 97%, 98%, 99%, 99.5%, 99.8%, 99.9% is also provided.

When referring to the adenovirus type, this may be in the form of the species and number, e.g. adenovirus C5, or simply by "Ad" followed by the number, e.g. Ad5. These terms are used interchangeably and have the same meaning.

DETAILED DESCRIPTION OF THE INVENTION

The adenovirus library generated by the present inventors forms the basis for the generation of new adenovirus vectors, vaccines and oncolytic adenoviruses, as described below. In many cases, the novel sequences from the newly-cloned adenoviruses confer improved properties on the vectors and oncolytic viruses.

The sequences of the newly-cloned adenoviral genomes are given in the sequence listing. Table 2 summarises the SEQ ID NOs corresponding to each cloned genome.

TABLE 2

Cloned adenovirus genome sequences

| Adenovirus | SEQ ID NO |
|---|---|
| A12 | SEQ ID NO: 1 |
| A18 | SEQ ID NO: 2 |
| A31 | SEQ ID NO: 3 |
| B3 | SEQ ID NO: 4 |
| B7 | SEQ ID NO: 5 |
| B16 | SEQ ID NO: 6 |
| B21 | SEQ ID NO: 7 |
| B50 | SEQ ID NO: 8 |
| B11 | SEQ ID NO: 9 |
| B14a | SEQ ID NO: 10 |
| B14b | SEQ ID NO: 11 |
| B34 | SEQ ID NO: 12 |
| B35 | SEQ ID NO: 13 |
| C1 | SEQ ID NO: 14 |
| C2 | SEQ ID NO: 15 |
| C5 | SEQ ID NO: 16 |
| C6 | SEQ ID NO: 17 |
| D8 | SEQ ID NO: 18 |
| D9 | SEQ ID NO: 19 |
| D10 | SEQ ID NO: 20 |
| D13 | SEQ ID NO: 21 |
| D17 | SEQ ID NO: 22 |
| D20 | SEQ ID NO: 23 |
| D24 | SEQ ID NO: 24 |
| D25 | SEQ ID NO: 25 |
| D26 | SEQ ID NO: 26 |
| D27 | SEQ ID NO: 27 |
| D33 | SEQ ID NO: 28 |
| D37 | SEQ ID NO: 29 |
| D69 | SEQ ID NO: 30 |
| E4 | SEQ ID NO: 31 |
| G52 | SEQ ID NO: 32 |

In addition to the cloned adenoviruses recited in Table 1, SEQ ID NO: 1411 corresponds to the sequence of the newly-cloned F41 adenovirus genome. Sequence variants of the B11, D8 and D17 adenoviruses are contained within SEQ ID NOs 1413, 1414 and 1415 respectively. It will be understood that any embodiments of the invention related to SEQ ID NOs 9, 18 and 22 may also be extrapolated to encompass SEQ ID NOs 1413, 1414 and 1415 respectively, if required.

Sequences of individual transcription units and genes of particular importance from the novel cloned adenoviruses are also provided in the sequence listing. The SEQ ID NOs of these genes are set out in the tables below, together with an indication of the function of relevant genes. Any plasmid sequences contained at the 5' and/or 3'-ends of the genome sequences in SEQ ID Nos 1-32 and 1411 would be straightforward for a person skilled in the art to identify, as they would simply identify the ITRs of the adenovirus genomes, which are known in the art, and are known to define the ends of the adenovirus genome.

Non-Coding Regions for High-Capacity Adenoviral Vectors

Non-coding regions from the 5' and 3' untranslated regions of the adenoviral genomes are important in generating high-capacity adenoviral vectors of the invention (see below). High-capacity adenoviral vectors comprise 5' and 3' inverted terminal repeats (ITRs), which are included in high-capacity adenoviral vectors. These are found within around 150 bp of each end of the viral genome. The 5' region also comprises the packaging signal 4). This ensures that the DNA is packaged into virus particles. The packaging signal is found within 500 bp of the 5' end of the genome, downstream of the 5' ITR. The positions of the regions in SEQ IDs 1-32 and 1411 which contain the 5'ITR, the 5'ITR and the packaging signal, and the 3'ITR are shown in Table 1.

The sequences comprising the 500 bp and 150 bp of the 5'-end, and the 150 bp of the 3'-end of SEQ IDs 1-32 are shown in Table 3. Some of these sequences comprise plasmid sequence. However, the 150 bp 5'UTR and 150 bp 3'ITR SEQ ID NOs corresponding to the B3, B16, 01, C2, C5, C6, D10, D13, D20, D24, D25, D26, D27, D33, D37, D69 and E4 adenoviruses in Table 3 do comprise the 5'ITRs and the 3'ITRs, respectively as defined in Table 1.

TABLE 3 key non-coding regions

| Adenovirus | 500 bp 5' UTR | 150 bp 5' UTR | 150 bp 3' ITR |
|---|---|---|---|
| A12 | SEQ ID NO: 33 | SEQ ID NO: 65 | SEQ ID NO: 97 |
| A18 | SEQ ID NO: 34 | SEQ ID NO: 66 | SEQ ID NO: 98 |
| A31 | SEQ ID NO: 35 | SEQ ID NO: 67 | SEQ ID NO: 99 |
| B3 | SEQ ID NO: 36 | SEQ ID NO: 68 | SEQ ID NO: 100 |
| B7 | SEQ ID NO: 37 | SEQ ID NO: 69 | SEQ ID NO: 101 |
| B16 | SEQ ID NO: 38 | SEQ ID NO: 70 | SEQ ID NO: 102 |
| B21 | SEQ ID NO: 39 | SEQ ID NO: 71 | SEQ ID NO: 103 |
| B50 | SEQ ID NO: 40 | SEQ ID NO: 72 | SEQ ID NO: 104 |
| B11 | SEQ ID NO: 41 | SEQ ID NO: 73 | SEQ ID NO: 105 |
| B14a | SEQ ID NO: 42 | SEQ ID NO: 74 | SEQ ID NO: 106 |
| B14b | SEQ ID NO: 43 | SEQ ID NO: 75 | SEQ ID NO: 107 |
| B34 | SEQ ID NO: 44 | SEQ ID NO: 76 | SEQ ID NO: 108 |
| B35 | SEQ ID NO: 45 | SEQ ID NO: 77 | SEQ ID NO: 109 |
| C1 | SEQ ID NO: 46 | SEQ ID NO: 78 | SEQ ID NQ: 110 |
| C2 | SEQ ID NO: 47 | SEQ ID NO: 79 | SEQ ID NO: 111 |
| C5 | SEQ ID NO: 48 | SEQ ID NO: 80 | SEQ ID NO: 112 |
| C6 | SEQ ID NO: 49 | SEQ ID NO: 81 | SEQ ID NO: 113 |
| D8 | SEQ ID NO: 50 | SEQ ID NO: 82 | SEQ ID NO: 114 |
| D9 | SEQ ID NO: 51 | SEQ ID NO: 83 | SEQ ID NO: 115 |
| D10 | SEQ ID NO: 52 | SEQ ID NO: 84 | SEQ ID NO: 116 |
| D13 | SEQ ID NO: 53 | SEQ ID NO: 85 | SEQ ID NO: 117 |
| D17 | SEQ ID NO: 54 | SEQ ID NO: 86 | SEQ ID NO: 118 |
| D20 | SEQ ID NO: 55 | SEQ ID NO: 87 | SEQ ID NO: 119 |
| D24 | SEQ ID NO: 56 | SEQ ID NO: 88 | SEQ ID NO: 120 |
| D25 | SEQ ID NO: 57 | SEQ ID NO: 89 | SEQ ID NO: 121 |
| D26 | SEQ ID NO: 58 | SEQ ID NO: 90 | SEQ ID NO: 122 |
| D27 | SEQ ID NO: 59 | SEQ ID NO: 91 | SEQ ID NO: 123 |
| D33 | SEQ ID NO: 60 | SEQ ID NO: 92 | SEQ ID NO: 124 |
| D37 | SEQ ID NO: 61 | SEQ ID NO: 93 | SEQ ID NO: 125 |
| D69 | SEQ ID NO: 62 | SEQ ID NO: 94 | SEQ ID NO: 126 |
| E4 | SEQ ID NO: 63 | SEQ ID NO: 95 | SEQ ID NO: 127 |
| G52 | SEQ ID NO: 64 | SEQ ID NO: 96 | SEQ ID NO: 128 |

Late Transcription Units and Capsid Proteins

The late transcription units (L1-L5) encode structural proteins, which are responsible for virus tropism. The main structural proteins which form the viral capsid are hexon, penton base, and fiber. Fiber proteins protrude from the capsid surface and are primarily responsible for cell tropism, though other parts of the viral capsid (e.g. penton base) may contribute in some cases[17]. The fiber knob binds to receptors on the surface of certain cells in order to mediate cell attachment and the first step of cell entry. Penton base is involved in internalisation of virus particles via interaction with cellular integrins[13]. The hexon protein contains hyper-variable regions (HVRs) which are serotype-specific and are therefore considered to be major immune determinants. Most neutralising antibodies against HAd5 bind to the hexon HVR sequences, and to a lesser extent the fiber knob[14].

The capsid proteins are also responsible for the induction of host immune responses such as neutralising antibodies. Antigens at the surface of the virion are mainly type-specific[13]. Accordingly, constructing vectors or oncolytic viruses with one or more capsid proteins listed in Table 4 below may help to avoid the issues of pre-existing immunity encountered with HAdV5-based vectors and viruses, for example if the virus from which the capsid protein is derived has a lower seroprevalence in the human population than HAdV5. In addition to the capsid proteins in Table 4, SEQ ID NOs 1443, 1426 and 1431 correspond to the fiber, penton and hexon genes of the newly-cloned F41 adenovirus genome, respectively, and the invention similarly encompasses constructing vectors or oncolytic viruses with these sequences.

Where a vector includes the L1 region, this means that it comprises all of the open reading frames (ORFs) forming part of the L1 region, as well as any intervening sequences (coding or non-coding). The vector also includes any flanking sequence involved in expression of the L1 genes (e.g. starting from the upstream transcription start site). Analogous provisions apply to the L2, L3, L4 and L5 regions. ORFs from each of these regions, for each of the cloned viruses, are provided in Table 5.

TABLE 4 capsid proteins

| Adenovirus | Fiber | Penton | Hexon |
|---|---|---|---|
| A12 | SEQ ID NO: 129 | SEQ ID NO: 161 | SEQ ID NO: 189 |
| A18 | SEQ ID NO: 130 | SEQ ID NO: 162 | SEQ ID NO: 190 |
| A31 | SEQ ID NO: 131 | SEQ ID NO: 163 | SEQ ID NO: 191 |
| B3 | SEQ ID NO: 132 | SEQ ID NO: 164 | SEQ ID NO: 192 |
| B7 | SEQ ID NO: 133 | SEQ ID NO: 165 | SEQ ID NO: 193 |
| B16 | SEQ ID NO: 134 | SEQ ID NO: 166 | SEQ ID NO: 194 |
| B21 | SEQ ID NO: 135 | SEQ ID NO: 167 | SEQ ID NO: 195 |
| B50 | SEQ ID NO: 136 | SEQ ID NO: 168 | SEQ ID NO: 196 |
| B11 | SEQ ID NO: 137 | SEQ ID NO: 169 | SEQ ID NO: 197 |
| B14a | SEQ ID NO: 138 | SEQ ID NO: 170 | SEQ ID NO: 198 |
| B14b | SEQ ID NO: 139 | SEQ ID NO: 171 | SEQ ID NO: 199 |
| B34 | SEQ ID NO: 140 | SEQ ID NO: 172 | SEQ ID NO: 200 |
| B35 | SEQ ID NO: 141 | SEQ ID NO: 173 | SEQ ID NO: 201 |
| C1 | SEQ ID NO: 142 | SEQ ID NO: 174 | SEQ ID NO: 202 |
| C2 | SEQ ID NO: 143 | SEQ ID NO: 175 | SEQ ID NO: 203 |
| C5 | SEQ ID NO: 144 | — | SEQ ID NO: 204 |
| C6 | SEQ ID NO: 145 | — | SEQ ID NO: 205 |
| D8 | SEQ ID NO: 146 | SEQ ID NO: 176 | SEQ ID NO: 206 |
| D9 | SEQ ID NO: 147 | SEQ ID NO: 177 | SEQ ID NO: 207 |
| D10 | SEQ ID NO: 148 | SEQ ID NO: 178 | SEQ ID NO: 208 |
| D13 | SEQ ID NO: 149 | SEQ ID NO: 179 | SEQ ID NO: 209 |
| D17 | SEQ ID NO: 150 | SEQ ID NO: 180 | SEQ ID NO: 210 |
| D20 | SEQ ID NO: 151 | SEQ ID NO: 181 | SEQ ID NO: 211 |
| D24 | SEQ ID NO: 152 | SEQ ID NO: 182 | SEQ ID NO: 212 |
| D25 | SEQ ID NO: 153 | SEQ ID NO: 183 | SEQ ID NO: 213 |
| D26 | SEQ ID NO: 154 | SEQ ID NO: 184 | SEQ ID NO: 214 |
| D27 | SEQ ID NO: 155 | SEQ ID NO: 185 | SEQ ID NO: 215 |
| D33 | SEQ ID NO: 156 | SEQ ID NO: 186 | SEQ ID NO: 216 |
| D37 | SEQ ID NO: 157 | SEQ ID NO: 187 | SEQ ID NO: 217 |
| D69 | SEQ ID NO: 158 | SEQ ID NO: 188 | SEQ ID NO: 218 |
| E4 | SEQ ID NO: 159 | — | SEQ ID NO: 219 |
| G52 | SEQ ID NO: 160 | — | SEQ ID NO: 220 |

TABLE 5

ORFs in L1, L2, L3, L4 and L5 regions

| Adeno-virus | SEQ ID NOs | | | | |
|---|---|---|---|---|---|
| | L1 ORFs | L2 ORFs | L3 ORFs | L4 ORFs | L5 ORFs |
| A12 | 253-254 | 249-252 | 246-248 | 242-244 | 234 |
| A18 | 290-291 | 287-289 | 283-285 | 279-281 | 271 |
| A31 | 326-327 | 323-325 | 320-322 | 316-318 | 308 |
| B3 | 363-364 | 359-362 | 355-358 | 351-353 | 341 |
| B7 | 401-402 | 397-400 | 393-396 | 389-391 | 378 |
| B16 | 439-440 | 435-438 | 431-434 | 426-429 | 416 |
| B21 | 478-479 | 474-477 | 470-473 | 465-468 | 455 |
| B50 | 516-517 | 512-515 | 508-511 | 503-506 | 493 |
| B11 | 551, 553 | 548-550 | 545-547 | 541-543 | 531 |
| B14a | 587-588 | 583-586 | 580-582 | 576-578 | 571 |
| B14b | 627-628 | 623-626 | 620-622 | 616-618 | 606 |
| B34 | 664-665 | 661-663 | 658-660 | 654-656 | 644 |
| B35 | 701, 703 | 698-700 | 695-697 | 691-693 | 681 |
| C1 | 740-741 | 736, 738 | 733, 739 | 729, 734 | 720, 731 |

TABLE 5-continued

ORFs in L1, L2, L3, L4 and L5 regions

| Adeno-virus | SEQ ID NOs | | | | |
|---|---|---|---|---|---|
| | L1 ORFs | L2 ORFs | L3 ORFs | L4 ORFs | L5 ORFs |
| C2 | 778-779 | 774-777 | 771-773 | 768-769 | 760 |
| C5 | 816-817 | 812, 814 | 809-810 | 805 | 796, 807 |
| C6 | — | 850, 852 | 847-848 | 842 | 834 |
| D8 | 885-886 | 881-884 | 878-880 | 874-876 | 870 |
| D9 | 923-924 | 919-922 | 916-918 | 911-914 | 901 |
| D10 | 959-960 | 955-958 | 952-954 | 948-950 | 938 |
| D13 | 997-999 | 993-996 | 990-992 | 986-988 | 975 |
| D17 | 1035-1036 | 1030-1034 | 1027-1029 | 1022-1025 | 1013 |
| D20 | 1069-1070 | 1066-1068 | 1063-1065 | 1059-1061 | 1049 |
| D24 | 1105-1106 | 1101-1104 | 1098-1100 | 1094-1096 | 1084 |
| D25 | 1143-1145 | 1139-1142 | 1136-1138 | 1131-1134 | 1120 |
| D26 | 1181-1182 | 1178-1180 | 1175-1177 | 1170-1173 | 1160 |
| D27 | 1219-1220 | 1216-1218 | 1213-1215 | 1208-1211 | 1197 |
| D33 | 1257-1258 | 1253-1256 | 1250-1252 | 1245-1248 | 1234 |
| D37 | 1294-1295 | 1291-1293 | 1288-1290 | 1283-1286 | 1273 |
| D69 | 1330, 1332 | 1326-1329 | 1323-1325 | 1318-1321 | 1308 |
| E4 | 1368-1369 | 1364-1367 | 1360-1363 | 1356-1358 | 1346 |
| G52 | — | — | 1394-1395 | — | 1381-1382 |
| F41 | — | 1429 | 1431-1432 | — | — |

Cell Tropism

Most adenoviral vectors and oncolytic adenoviruses currently in use or development are based on HAdV5. One limitation of HAdV5-based vectors and viruses is the strong liver cell tropism of HAdV5 when administered intravenously.

The adenoviral genome sequences cloned by the present inventors provide a wide repertoire of sequences from which vectors and oncolytic viruses can be made, and many of these vectors and oncolytic viruses will have the advantage of a different cell tropism from HAdV5, based on the cell tropism of the virus from which the vector or oncolytic virus sequence is derived. If the vector or oncolytic virus is made as a hybrid of sequences from different viruses, its cell tropism will be determined by the tropism of the virus from which the capsid genes are derived (in particular the fiber shaft and knob).

For example, human adenovirus type 17 (HAdV17) shows endothelial cell tropism (see Example 3). Species B viruses demonstrate high transduction efficiencies in epithelial (HeLa and A549 cells) and endothelial cells, while Ad5 still displays the highest transduction rates in other human and murine cell types (hepatocytes, lymphocytes, neuroblastoma cells and myoblasts). Exploring natural adenovirus diversity revealed distinct tropisms in vivo (Example 1; FIG. 2)

Table 6 summarises the cell and/or tissue tropism of the cloned adenoviruses, any known cellular receptors for the cloned adenoviruses, and the types of infection caused by these adenoviruses. The tissue tropism and type of infection caused provide some guidance as to the likely cell tropism.

Table 6 also lists some possible therapeutic uses of vectors or oncolytic viruses derived from these adenoviral genomes, based on their tropism.

TABLE 6 tropism
Information adapted from references 15 and 16 (incorporated herein by reference).

| Ad | Cell tropism | Receptors | Tissue tropism | Type of infection | Possible therapeutic uses |
|---|---|---|---|---|---|
| A12 | | | Intestine | Gastrointestinal, respiratory, urinary | |
| A18 | | | Intestine | Gastrointestinal, respiratory, urinary | |
| A31 | | | Intestine | Gastrointestinal, respiratory, urinary | |
| B3 | Epithelial/ endothelial | DSG-2[17] | Tonsils/ respiratory tract | Keratoconjunctivitis, gastrointestinal, respiratory, urinary | Epithelial tumours |
| B16 | Epithelial/ endothelial | CD46[18] | Tonsils/ respiratory tract | Keratoconjunctivitis, gastrointestinal, respiratory, urinary | |
| B21 | Epithelial/ endothelial | CD46[18] | Tonsils/ respiratory tract | Keratoconjunctivitis, gastrointestinal, respiratory, urinary | |
| B50 | Epithelial/ endothelial | CD46[18] | Tonsils/ respiratory tract | Keratoconjunctivitis, gastrointestinal, respiratory, urinary | |
| B11 | Epithelial/ endothelial | CD46 DSG-2[17] | Hematopoietic cells, kidney, urinary bladder | Gastrointestinal, respiratory, urinary | Epithelial tumours |
| B14 | Epithelial/ endothelial | DSG-2[17] | Hematopoietic cells, kidney, urinary bladder | Gastrointestinal, respiratory, urinary | Epithelial tumours |
| B34 | Epithelial/ endothelial | | Hematopoietic cells, kidney, urinary bladder | Gastrointestinal, respiratory, urinary | |
| B35 | Epithelial/ endothelial | CD46[18] | Hematopoietic cells, kidney, urinary bladder | Gastrointestinal, respiratory, urinary | |
| C1 | | | Respiratory tract | Respiratory, gastrointestinal including hepatitis, urinary | |

TABLE 6-continued tropism
Information adapted from references 15 and 16 (incorporated herein by reference).

| Ad | Cell tropism | Receptors | Tissue tropism | Type of infection | Possible therapeutic uses |
|---|---|---|---|---|---|
| C5 | | | Respiratory tract (liver in mice) | Respiratory, gastrointestinal including hepatitis, urinary | |
| C6 | | | Respiratory tract | Respiratory, gastrointestinal including hepatitis, urinary | |
| D8 | | | Eye | Keratoconjunctivitis, gastrointestinal | |
| D9 | | | Eye | Keratoconjunctivitis, gastrointestinal | |
| D10 | | | Eye | Keratoconjunctivitis, gastrointestinal | |
| D13 | | | Eye | Keratoconjunctivitis, gastrointestinal | |
| D17 | Endothelial cells | hCAR CD46 | Eye | Keratoconjunctivitis, gastrointestinal | Endothelial disease or dysfunction, including coagulation disorders |
| D20 | | | Eye | Keratoconjunctivitis, gastrointestinal | |
| D24 | | | Eye | Keratoconjunctivitis, gastrointestinal | |
| D25 | | | Eye | Keratoconjunctivitis, gastrointestinal | |
| D26 | | | Eye | Keratoconjunctivitis, gastrointestinal | |
| D27 | | | Eye | Keratoconjunctivitis, gastrointestinal | |
| D33 | | | Eye | Keratoconjunctivitis, gastrointestinal | |
| D37 | | | Eye | Keratoconjunctivitis, gastrointestinal | |
| D69 | | | Eye | Keratoconjunctivitis, gastrointestinal | |
| E4 | | | Respiratory tract, eye | Keratoconjunctivitis, respiratory | | hCAR: human coxsackievirus and adenovirus receptor
DSG-2: desmoglein 2 is a calcium-binding transmembrane glycoprotein and forms part of the cadherin protein family.
DSG-2 is a component of the cell-cell adhesion structure in epithelial cells, and is overexpressed in various epithelial cancers, including gastric cancer, squamous cell carcinomas, melanoma, metastatic prostate cancer and bladder cancer[17].

Accordingly, the invention provides a method of infecting a cell with an adenoviral vector according to the invention wherein the cell is an epithelial cell or an endothelial cell. Also provided is a method of infecting a tissue with an adenoviral vector according to the invention wherein the tissue is selected from the intestine, tonsils, respiratory tract, hematopoietic cells, kidney, urinary bladder and eye. In some embodiments, the invention provides a method for treating one or more diseases recited in Table 4, for example, wherein the treatment comprises infecting the corresponding cell and/or tissue as recited in Table 4. For example, the invention provides a method of treating epithelial tumours comprising administering an adenoviral vector of the invention. Similarly, the invention provides a method of treating endothelial disease or dysfunction, for example a coagulation disorder, comprising administering an adenoviral vector of the invention. The invention further provides a method of treating a disease affecting the gastrointestinal, respiratory or urinary tract or the keratoconjunctiva or hepatitis infection comprising administering an adenoviral vector of the invention.

In some embodiments, the invention provides an oncolytic adenoviral vector, for use in treating osteosarcoma, wherein the oncolytic adenoviral vector is derived from the adenovirus B21. Similarly, the invention provides a method of treating osteosarcoma or glioblastoma comprising administering an oncolytic adenoviral vector derived from adenovirus B21 (B21 is the same as Ad21).

In other embodiments, the invention provides an oncolytic adenoviral vector, for use in treating lung carcinomas, wherein the oncolytic adenoviral vector is derived from the adenovirus B35 or D69. Similarly, the invention provides a method of treating a lung carcinoma comprising administering an oncolytic adenoviral vector derived from adenovirus B35 or D69.

Similarly, the invention provides a method of targeting human airway epithelial comprising administering an adenoviral vector derived from adenovirus B21, D37 or D69.

In some embodiments, the invention provides an adenoviral vector for use in infecting lung cells or tissue. In some embodiments, the adenoviral vector is derived from Ad21, Ad3, Ad37, or Ad69. In some embodiments, the adenoviral viral vector is for use in treating a disease of the lung, such as lung cancer or cystic fibrosis. Similarly, the invention provides a method of treating a disease of the lung comprising administering an adenoviral vector derived from adenovirus Ad21. In some embodiments, the adenoviral vector is oncolytic. In some embodiments the adenoviral vector comprises a transgene capable of treating the disease. In some embodiments, the adenoviral vector carries the CRISPR/Cas9 components and the treatment involves correcting the mutated gene sequence.

In one embodiment, the invention provides a method of transducing osteosarcoma cells or an osteosarcoma-derived cell line, comprising contacting the cells with a plasmid or adenoviral vector of the present invention, preferably wherein adenoviral sequences are derived from the adenovirus B21.

In another embodiment, the invention provides a method of transducing epithelial cells or an epithelial-derived cell line, comprising contacting the cells with a plasmid or adenoviral vector of the present invention, preferably wherein adenoviral sequences are derived from the adenovirus B3, B14, B16, B35 or B50.

In another embodiment, the invention provides a method of transducing endothelial cells or an endothelial-derived cell line, comprising contacting the cells with a plasmid or adenoviral vector of the present invention, preferably wherein adenoviral sequences are derived from the adenovirus B16 or B50.

In another embodiment, the invention provides a method of transducing breast cancer cells or a breast cancer-derived cell line, comprising contacting the cells with a plasmid or adenoviral vector of the present invention, preferably wherein adenoviral sequences are derived from the adenovirus D37. The invention also provides a method of treating breast cancer comprising administering an adenoviral vector derived from adenovirus D37. In some embodiments, the adenoviral vector is oncolytic. In some embodiments the adenoviral vector comprises a transgene capable of treating the disease.

In another embodiment, the invention provides a method of transducing liver cells or a liver-derived cell line, comprising contacting the cells with a plasmid or adenoviral vector of the present invention, preferably wherein adenoviral sequences are derived from the adenovirus C5, or B50.

In another embodiment, the invention provides a method of transducing lung cells or a lung-derived cell line, comprising contacting the cells with a plasmid or adenoviral vector of the present invention, preferably wherein adenoviral sequences are derived from the adenovirus Ad21, Ad37 or Ad69.

In one embodiment, the invention also provides adenoviral vectors of the invention for use in treating osteosarcoma, preferably wherein adenoviral sequences are derived from the adenovirus B21.

The invention provides a method of screening for cell tropisms, which comprises:
a) contacting a cell with an adenoviral vector as described herein; and
b) determining whether the vector infects the cell.

Similarly, the invention provides a method of screening for cell tropisms, which comprises:
a) contacting a cell with an adenoviral vector from a library of two or more adenoviral vectors as described herein;
b) determining whether the vector infects the cell; and
c) repeating steps a) and b) for at least one more member of the library (e.g. for at least 2, 3, 4, 5, 6, 7 or more) or each member of the library; and
d) optionally repeating steps a) to c) using a different cell type.

Advantageously, the vector may comprise a reporter gene which is a fluorescent protein or luciferase, and step b) may comprise determining whether the cell fluoresces or glows as a result of expression of the fluorescent protein or the luciferase. For example, step b) may comprise adding a luciferase substrate, such as furimazine or luciferin, and measuring the luminescence units.

In some embodiments, the method of screening for cell tropisms is carried out in vitro. In some embodiments, the method of screening for cell tropisms is carried out in vivo and comprises analysing the biodistribution as detected by transgene expression levels and/or viral genome level. For example, an in vivo method may be carried out in a mouse, rat, rabbit or guinea pig.

The invention further provides a method of screening for cell tropisms, which comprises:
a) contacting a cell with an adenoviral vector as described herein; and
b) determining whether the vector lyses the cell.

Similarly, the invention provides a method of screening for cell tropisms, which comprises:
a) contacting a cell with an adenoviral vector from a library of two or more adenoviral vectors as described herein;
b) determining whether the vector lyses the cell; and
c) repeating steps a) and b) for at least one more member of the library (e.g. for at least 2, 3, 4, 5, 6, 7 or more) or each member of the library; and
d) optionally repeating steps a) to c) using a different cell type.

In some embodiments, the step of determining whether the vector lyses the cells comprises staining the cells with crystal violet or methylene blue.

Advantageously, use of a method of screening for cell tropisms as described herein allows identification of a virus candidate for disease specific targeting. This allows development of novel therapeutic agents by carrying out further steps of modifying the virus using the methods described herein, e.g. so that it contains a transgene. Accordingly, the invention also provides a virus candidate for disease specific targeting identified by or identifiable by the method of screening for cell tropisms as described herein. Accordingly, the invention provides a method of treatment of a disease that affects a cell type comprising administering an adenoviral vector as described herein which has been identified (or can be identified) as infecting that cell type by a method of screening for cell tropisms as described herein, wherein the vector has been modified to incorporate one or more transgenes useful for treating the disease and/or wherein the vector is oncolytic for the cell type. In some embodiments, the one or more transgenes comprise a therapeutic agent. In some embodiments, the one or more transgenes is the CRISPR/Cas9 system.

The invention also provides a method of targeting a cell by contacting the cell with an adenoviral vector as described herein, wherein the type of cell has been identified (or can be identified) as a type of cell that is infected by the adenoviral vector using a method of screening for cell tropisms as described herein. In some embodiments, the vector has been modified to incorporate one or more transgenes. In some embodiments, the vector is oncolytic for the cell type. Thus, the method of targeting described herein provides a means to deliver a transgene of interest to a cell.

Early Transcription Units

The early transcription units are E1, E2, E3 and E4. E1, E2 and E4 are majorly involved in the replication cycle of adenoviruses.

The E1 transcription unit comprises E1A and E1B, and is the main unit responsible for initiating replication after cellular infection. E1A activates transcription of a number of viral genes as well as host cell genes. The protein coding genes of E1B have various functions, for instance suppressing apoptosis. The E1 region can be deleted in the vectors of the invention to make them replication deficient and consequently safer for use in therapy. Deletion of the E1 region (and optionally also other regions of the viral genome) also provides space to accommodate transgenes.

The E2 transcription unit encodes the DNA polymerase (Pol), the terminal protein (TP), and the DNA-binding protein (DBP) which are involved in replication and amplification of adenoviral DNA.

Products of the E4 transcription unit are involved in transcription, apoptosis, cell cycle control, DNA repair, cell signalling and posttranslational modifications.

The E3 transcription unit exhibits immunomodulatory functions: it protects cells from killing mediated by cytotoxic T cells and death-inducing cytokines, and can prevent apoptosis. This region varies significantly between the different adenovirus serotypes and can contain a different number of protein-coding genes.

Table 7 lists the open reading frames (ORFs) in the each of the early transcription units, for each of the cloned adenoviral genomes.

When reference is made to deletion of the E1 region, this means that minimally all the ORFs listed in Table 7 as forming part of the E1 region are deleted, and preferably also any intervening sequence, e.g. non-coding sequence or any further coding sequence. Some flanking sequence may also be deleted (e.g. the transcription start site).

Similarly, when reference is made to deletion of the E3 region, this means that minimally all the ORFs listed in Table 7 as forming part of the E3 region are deleted, and preferably also any intervening sequence, e.g. non-coding sequence or any further coding sequence. Some flanking sequence may also be deleted (e.g. the transcription start site).

Where a vector includes the E1 region, this means that it comprises all of the ORFs listed in Table 7 as forming part of the E1 region, including any intervening sequences (coding or non-coding). The vector also includes any flanking sequence involved in expression of the E1 genes (e.g. starting from the upstream transcription start site). Analogous provisions apply to the E2, E3 and E4 regions.

TABLE 7

ORFs in E1, E2, E3 and E4 regions

| Adeno-virus | SEQ ID NOs | | | |
|---|---|---|---|---|
| | E1 ORFs | E2 ORFs | E3 ORFs | E4 ORFs |
| A12 | 260-262 | 245, 256-257 | 236-241 | 229-233 |
| A18 | 296-299 | 282, 292-293 | 273-278 | 265-270 |
| A31 | 332-333 | 319, 329 | 310-315 | 302-307 |
| B3 | 369-372 | 354, 365-366 | 343-350 | 336-340 |
| B7 | 407-410 | 392, 403-404 | 380-388 | 373-377 |
| B16 | 445-449 | 430, 441-442 | 418-425 | 411-415 |
| B21 | 484-487 | 469, 480-481 | 457-464 | 450-454 |
| B50 | 522-525 | 507, 518-519 | 495-502 | 488-492 |
| B11 | 557-563 | 544, 552, 554-556 | 533-540 | 526-530 |
| B14a | 593-599 | 579, 589-590 | 573-575 | 566-570 |
| B14b | 633-637 | 619, 629-630 | 608-615 | 601-605 |
| B34 | 670-673 | 657, 666-668 | 646-653 | 639-643 |
| B35 | 707-711 | 694, 702, 704-706 | 683-690 | 676-680 |
| C1 | 749-752 | 730, 732, 743-745 | 721-728 | 714-718 |
| C2 | 785-788 | 770, 780, 782 | 761-767 | 754-758 |
| C5 | 823-826 | 806, 808, 818, 820 | 797-804 | 790-794 |
| C6 | 861-864 | 858 | 835-838, 840-841 | 828-832 |

TABLE 7-continued

ORFs in E1, E2, E3 and E4 regions

| Adeno-virus | SEQ ID NOs | | | |
|---|---|---|---|---|
| | E1 ORFs | E2 ORFs | E3 ORFs | E4 ORFs |
| D8 | 891-894 | 877, 888 | 872-873 | 865-869 |
| D9 | 929-931 | 915, 926 | 903-910 | 896-900 |
| D10 | 965-967 | 951, 962 | 940-947 | 933-937 |
| D13 | 1004-1007 | 989, 1001 | 977-985 | 969-974 |
| D17 | 1041-1043 | 1026, 1038 | 1015-1021 | 1008-1012 |
| D20 | 1075-1077 | 1062, 1072 | 1051-1058 | 1044-1048 |
| D24 | 1111-1113 | 1097, 1108 | 1086-1093 | 1079-1083 |
| D25 | 1150-1153 | 1135, 1147 | 1122-1130 | 1114-1119 |
| D26 | 1188-1190 | 1174, 1185 | 1162-1169 | 1154-1159 |
| D27 | 1225-1227 | 1212, 1222 | 1199-1207 | 1192-1196 |
| D33 | 1263-1265 | 1249, 1260 | 1236-1244 | 1229-1233 |
| D37 | 1300-1302 | 1287, 1296, 1297 | 1275-1282 | 1266-1272 |
| D69 | 1337-1339 | 1322, 1334 | 1310-1317 | 1303-1307 |
| E4 | 1374-1375 | 1359, 1370-1371 | 1348-1355 | 1340-1345 |
| G52 | 1407-1410 | — | 1384-1388 | 1376-1380 |
| F41 | 1416-1418 | 1421, 1423, — | 1436-1440- | 1444-1447- |

Adenoviral Vectors

Adenoviral vectors may be replication-deficient (RD) or replication-competent (RC). Vectors have certain regions of the adenoviral genome deleted to provide space for foreign DNA (e.g. transgenes). Replication-deficient adenoviral vectors are formed by deletion of the E1 region (which comprises the DA and E1B essential early genes) in the adenoviral genome, which ensures complete inhibition of viral replication in cells. Amplification of replication-deficient adenoviral vectors containing DNA of non-viral origin is feasible if essential viral components are provided in the helper cell in trans. This can be accomplished by generation of stable cell lines which complement for the lacking genes (see below).

Replication-competent adenoviral vectors usually lack the E3 region, as the E3 genes are not essential for Ad replication in cell culture or in vivo. Further details regarding RD and RC vectors may be found in reference 25, which is incorporated herein by reference.

As noted above, adenoviral cell and tissue tropism is determined primarily by the fiber capsid protein, in particular the stalk and knob regions of this protein. Other viral capsid proteins may also contribute to cell entry.

Accordingly, in one embodiment, the invention provides an adenoviral vector comprising a fiber gene selected from SEQ ID NOs:130-131, 135, 138-140, 142, 145-146, 149, 151, 153, 155 and 158-160, or a sequence at least 70% identical thereto.

Preferably, the sequence is at least 80%, 85%, 90%, 95%, 96%, 97%, 98%, 99%, 99.5% or 99.9% identical to a sequence selected from SEQ ID NOs:130-131, 135, 138-140, 142, 145-146, 149, 151, 153, 155 and 158-160.

The vector may further comprise a penton gene selected from SEQ ID NOs: 161-175 and 177-192, or a sequence at least 70% identical thereto. Preferably, the sequence is at least 80%, 85%, 90%, 95%, 96%, 97%, 98%, 99%, 99.5% or 99.9% identical to a sequence selected from SEQ ID NOs: 161-175 and 177-192.

The vector may further comprise a hexon gene selected from SEQ ID NOs:193-207 and 209-224, or a sequence at least 70% identical thereto. Preferably, the sequence is at least 80%, 85%, 90%, 95%, 96%, 97%, 98%, 99%, 99.5% or 99.9% identical to a sequence selected from SEQ ID NOs: 193-207 and 209-224.

The fiber, penton and hexon genes are preferably all derived from the same viral serotype (see Table 4).

Hybrid vectors may be constructed, comprising a fiber gene selected from SEQ ID NOs: 130-131, 135, 138-140, 142, 145-146, 149, 151, 153, 155 and 158-160 or a sequence at least 70% identical thereto, but comprising further viral sequences (coding and/or non-coding) from a different adenoviral serotype. The further viral sequences are from another adenoviral serotype forming part of the new library disclosed herein (selected from SEQ ID NOs:1-15 and 17-32), and preferably are not from human adenovirus 5 (Accession No. M73260). Adenoviral non-coding and coding sequences that can be incorporated into different types of vectors of the invention are discussed in further detail below.

This embodiment of the invention may be combined with any of the viral vector types described herein, including first generation vectors, including vaccine vectors. The vector according to this embodiment may also be a helper vector.

First Generation Adenoviral Vectors

The E1 region and/or the E3 region is deleted in first generation vectors of the invention. Deletion of such regions (and optionally also other regions of the viral genome) provides space to accommodate transgenes. Deletion of the E1 region makes the vectors replication deficient and consequently safer for use in therapy. Since the E1 gene products are required for viral growth, they are provided in trans in specific cell lines to allow production and amplification of the vectors. Vectors in which only the E3 region is deleted are replication competent.

Therefore, in one embodiment, the invention provides an adenoviral vector comprising a sequence selected from SEQ ID NOs:1-3, 5-8, 10-12, 14-15, 17-25 and 27-32, or a sequence at least 50% identical thereto, that lacks the E1 region.

Preferably, the sequence is at least 60%, 70%, 80%, 85%, 90%, 95%, 96%, 97%, 98%, 99%, 99.5% or 99.9% identical to a sequence selected from SEQ ID NOs:1-3, 5-8, 10-12, 14-15, 17-25 and 27-32.

In another embodiment, the invention provides an adenoviral vector comprising a sequence selected from SEQ ID NOs:1-8, 10-12, 14-15 and 17-32, or a sequence at least 50% identical thereto, that lacks the E1 region and the E3 region.

Preferably, the sequence is at least 60%, 70%, 80%, 85%, 90%, 95%, 96%, 97%, 98%, 99%, 99.5% or 99.9% identical to a sequence selected from SEQ ID NOs:1-8, 10-12, 14-15 and 17-32.

In a further embodiment, the invention provides an adenoviral vector comprising a sequence selected from SEQ ID NOs:1-3, 5-12, 14-15 and 17-32, or a sequence at least 50% identical thereto, that lacks the E3 region.

Preferably, the sequence is at least 60%, 70%, 80%, 85%, 90%, 95%, 96%, 97%, 98%, 99%, 99.5% or 99.9% identical to a sequence selected from SEQ ID NOs:1-3, 5-12, 14-15 and 17-32.

Hybrid vectors with a fiber protein from a different serotype can be constructed, as described above. Accordingly, the first-generation vectors may have the fiber gene replaced with a fiber gene from a different adenoviral serotype, selected from SEQ ID NOs:129-143 and 145-160, or a sequence at least 70% identical thereto (preferably at least 80%, 85%, 90%, 95%, 96%, 97%, 98%, 99%, 99.5% or 99.9% identical).

E1-deleted vectors can accept DNA insertions of up to around 5.1 kb. Vectors lacking both the E1 and the E3 regions can accommodate up to around 8.2 kb of foreign DNA[19]. Accordingly, a transgene (or one or more transgenes) inserted into the first generation adenoviral vectors of the invention may be up to around 5.1 kb in size in total if E1 is deleted, or up to around 8.2 kb in size in total if E1 and E3 are deleted.

It may be beneficial to retain the E3 region in some cases, as the E3 gene products include proteins which facilitate release of virus particles from cells and reduce cytotoxic T cell responses against cells transduced with the vector.

The above vectors can be used, for example, as helper vectors, oncolytic vectors, or vaccine vectors. Helper vectors should be replication deficient. Oncolytic vectors are replication competent. Vaccine vectors may be replication deficient, but are preferably replication competent as this may lead to the induction of better immune responses.

High-Capacity Adenoviral Vectors

High-capacity adenoviral vectors lack all viral coding sequences. The benefit of such vectors is that they can accommodate much larger transgenes, or multiple transgenes, than the first generation vectors in which only some coding sequences are deleted.

The only required sequences from the viral genome are cis-acting elements located at both ends of the adenoviral DNA molecule, which should include the packaging signal ($\psi$) located at the 5' end of the genome, and the inverted terminal repeats (ITRs) at both ends of the adenoviral genome. For the commonly used adenovirus type 5 the ITR is 103 bp in length and the packaging/enhancer sequences span nucleotides 194-458 bp located at the left arm of the adenoviral genome. In general, 500 bp at the 5' end of the genome will comprise the 5' ITR and the packaging signal, and 150 bp at the 3' end of the genome will comprise the 3' ITR.

Since high-capacity adenoviral vectors lack all viral coding regions, they are constructed and propagated in conjunction with an adenoviral helper vector, which provides the necessary viral functions (early and late proteins necessary for replication) in trans (see below). The high-capacity vectors can be separated from the helper vectors, for example by ultracentrifugation on cesium chloride density gradients and/or anion exchange and size exclusion chromatography.

High-capacity adenoviral vectors can accommodate up to around 37 kb of foreign genetic material (e.g. one large transgene, or more than one transgene), and they are therefore useful for carrying large transgenes or multiple transgenes (e.g. 2, 3, 4, 5 or more transgenes) and/or other heterologous DNA sequences.

Therefore, in one embodiment, the invention provides an adenoviral vector comprising a sequence selected from the sequences contained within SEQ ID NO: 1-13 and 18-32 at the positions defined in Table 1, column 4 or a sequence at least 80% identical thereto, at the 5' end, and the positions defined in Table 1, column 5, or a sequence at least 80% identical thereto, at the 3' end.

Preferably, the sequences are at least 85%, 90%, 95%, 96%, 97%, 98%, 99%, 99.5% or 99.9% identical to the sequences contained within SEQ ID NO: 1-13 and 18-32 at the positions defined in Table 1, column 4, and the positions defined in Table 1, column 5.

In one embodiment, the invention provides an adenoviral vector comprising a sequence selected from SEQ ID NOs: 33-45 and 50-64, or a sequence at least 80% identical thereto, at the 5' end, and a sequence selected from SEQ ID NOs:97-109 and 114-128, or a sequence at least 80% identical thereto, at the 3' end.

Preferably, the sequences are at least 85%, 90%, 95%, 96%, 97%, 98%, 99%, 99.5% or 99.9% identical to SEQ ID NOs:33-45, 50-64, 97-109 and 114-128.

HCAdV Applications—CRISPR/Cas9

Advantageously, gene deleted high-capacity adenoviral vectors (HCAdVs) of the invention may offer the ability to delivery one or more large genes to a cell of interest. For example, in some embodiments, a gene-deleted high-capacity adenoviral vector has a packing capacity of at least 15 kb, e.g. at least 20, 25, 30, 35, 40 or 45 kb. For example, in some embodiments, the gene-deleted high-capacity adenoviral vector comprises at least 15 kb, e.g. at least 20, 25, 30, 35, 40 or 45 kb, of DNA which is non-adenoviral genome sequence. The high-capacity adenoviral vectors of the invention may be used to deliver the components of the CRISPR/Cas9 system. The advantage of using the high-capacity adenovirus vectors for this purpose is that a single viral vector can be used, optionally with multiple guide RNAs. They may also be used to deliver transcription activator-like effector nucleases (TALENs) or zinc-finger nucleases (ZFNs). A useful application of these vectors is in vivo gene correction to treat genetic diseases. After cutting of the affected target locus in the host genome and in the presence of a respective donor DNA (which can be delivered by an adenoviral vector or an adeno-associated viral (AAV) vector), the mutated gene can be repaired by homology-directed DNA repair. In addition, such vectors can be used to treat infectious disease, for example as an antiviral approach to cut and destroy viral genomes. The invention provides these uses accordingly.

The clustered regularly interspaced short palindromic repeats (CRISPR)/Cas9 system allows for straightforward in vivo genome editing. Nevertheless, viral delivery of all required components including Cas9 and one or more guide RNA (gRNA) expression units using one single viral vector has not been fully exploited. Gene deleted high-capacity adenoviral vectors (HCAdVs) can efficiently deliver all expression units of the complete CRISPR/Cas9 machinery, including multiple gRNAs, into a broad variety of target cells using a single viral vector. However, the complicated handling of large DNA constructs and the time consuming production procedure hampered the use of HCAdV to deliver the CRISPR/Cas9 machinery for genome editing approaches. The present inventors have provided a toolbox for HCAdV genome manipulation for the fast and simple introduction of the customized CRISPR/Cas9 machinery to provide new instruments to improve somatic genome editing approaches in mammalian cells.

The inventors generated a new CRISPR/Cas9 shuttle plasmid toolbox containing the Cas9 nuclease gene, either utilising a constitutive or an inducible promoter, and a gRNA expression unit enabling customisation of the CRISPR/Cas9 for a desired target sequence. This allows cloning or recombining of all CRISPR/Cas9 components into the HCAdV genome in one step. To use several gRNA expression units for multiplexing the CRISPR/Cas9 system, further gRNA expression units can be easily included. Insertion of the CRISPR/Cas9 machinery can be either performed by recombineering[20] or conventional cloning. Further details regarding the CRISPR/Cas9 system, including the Cas9 gene and design of gRNAs, can be found in reference 21 (incorporated herein by reference).

Therefore, in one embodiment, the invention provides a plasmid which shares at least two regions of sequence homology with an adenoviral sequence of interest and which comprises the Cas9 gene and a guide RNA expression unit. In some embodiments, the Cas9 gene is under control of a constitutive promoter. In some embodiments, the Cas9 gene is under control of an inducible promoter. The regions of sequence homology may be designed to allow the Cas9 gene to be inserted into a chosen location in the adenoviral sequence. For example, in some embodiments, the at least two regions of sequence homology are designed so that the Cas9 gene and the gRNA expression unit are inserted into the E3 region of the adenoviral sequence. In some embodiments, the plasmid is the pAdV-FTC plasmid. Such a plasmid may be used in the methods of inserting one or more transgenes described herein as the second nucleic acid molecule.

Therefore, in one embodiment, the invention provides an adenoviral vector comprising a sequence selected from the sequences contained within SEQ ID NO: 1-13 and 18-32 at the positions defined in Table 1, column 4 or a sequence at least 80% identical thereto, at the 5' end, and the positions defined in Table 1, column 5, or a sequence at least 80% identical thereto, at the 3' end, and further comprising a Cas9 gene and at least one guide RNA. Preferably, the degree of sequence identity is at least 85%, 90%, 95%, 96%, 97%, 98%, 99%, 99.5% or 99.9%.

In one embodiment, the invention provides an adenoviral vector comprising a sequence selected from SEQ ID NOs: 33-45 and 50-64, or a sequence at least 80% identical thereto, at the 5' end, and a sequence selected from SEQ ID NOs:97-109 and 114-128, or a sequence at least 80% identical thereto, at the 3' end, and further comprising a Cas9 gene and at least one guide RNA.

Preferably, the degree of sequence identity is at least 85%, 90%, 95%, 96%, 97%, 98%, 99%, 99.5% or 99.9%.

The vector may comprise more than one guide RNA, for example two, three, four, five, eight, 10, 15, 20, 25, 30, 40, 50 or more guide RNAs.

The Cas9 gene may be expressed under the control of a constitutive or an inducible promoter.

In one embodiment, the invention provides an adenoviral vector as described herein, further comprising a gene encoding a transcription activator-like effector nuclease (TALEN) or a zinc-finger nuclease.

In some embodiments, the adenoviral vectors disclosed herein comprise at least 1 kb of non-adenoviral sequence, e.g. at least 2, 5, 10, 15, 20, 25, 30, 35 or 40 kb non-adenoviral sequence. In some embodiments, the non-adenoviral sequence encodes one or more transgenes of interest. In some embodiments, the non-adenoviral sequence is not plasmid sequence.

HCAdV Applications—Transposons

The high-capacity adenoviral vectors of the invention may be utilised in conjunction with the Sleeping Beauty transposon system, or other transposon systems such as PiggyBAC[22], to facilitate stable modification of transduced target cells. Any cell type, including stem cells, can be modified by the adenovirus-Sleeping Beauty hybrid vector system[23].

Accordingly, in one embodiment, the invention provides an adenoviral vector comprising a sequence selected from the sequences contained within SEQ ID NO: 1-13 and 18-32 at the positions defined in Table 1, column 4 or a sequence at least 80% identical thereto, at the 5' end, and the positions defined in Table 1, column 5, or a sequence at least 80% identical thereto, at the 3' end, and further comprising a Sleeping Beauty transposase gene (SEQ ID NO:223) and a transgene flanked by the inverted repeats of the Sleeping Beauty transposon (SEQ ID NOs:224 and 225), or comprising a PIGGYBac transposase gene (SEQ ID NO:226) and a transgene flanked by the inverted repeats of the PIGGYBac transposon.

Preferably, the sequences are at least 85%, 90%, 95%, 96%, 97%, 98%, 99%, 99.5% or 99.9% identical to the sequences contained within SEQ ID NO: 1-13 and 18-32 at the positions defined in Table 1, column 4, and the positions defined in Table 1, column 5.

In one embodiment, the invention provides an adenoviral vector comprising a sequence selected from SEQ ID NOs: 33-45 and 50-64, or a sequence at least 80% identical thereto, at the 5' end, and a sequence selected from SEQ ID NOs:97-109 and 114-128, or a sequence at least 80% identical thereto, at the 3' end, and further comprising a Sleeping Beauty transposase gene (SEQ ID NO:223) and a transgene flanked by the inverted repeats of the Sleeping Beauty transposon (SEQ ID NOs:224 and 225), or comprising a PIGGYBac transposase gene (SEQ ID NO:226) and a transgene flanked by the inverted repeats of the PIGGYBac transposon.

Preferably, the sequences are at least 85%, 90%, 95%, 96%, 97%, 98%, 99%, 99.5% or 99.9% identical to SEQ ID NOs:33-45, 50-64, 97-109 and 114-128.

In preferred embodiments, the transposase is expressed under the control of an inducible promoter. It is particularly preferred that this should be a cell-specific promoter, permitting expression of the transgene only in target cells of interest.

The adenovirus-Sleeping Beauty or adenovirus-PiggyBac hybrid vectors of the invention can be used to stably integrate transgenes into stem cells, e.g. hematopoietic stem cells. The main advantage of this strategy is that it avoids the sophisticated ex vivo transduction procedure usually required to transform hematopoietic stem cells. Instead, these stem cells can be directly transduced in vivo after mobilisation form the bone marrow and subsequent systemic administration of the hybrid vectors. Transgenes that can be stably integrated into these stem cells include those encoding coagulation factor VIII, coagulation factor IX, von Willebrand factor, haemoglobin, and other genes involved in genetic disorders derived from HSCs.

Transgenes for Inclusion in Adenoviral Vectors

The adenoviral vectors of the invention may include any transgene (or more than one transgene). Transgenes with therapeutic utility are preferred.

Transgenes of particular interest in human gene therapy are listed below by way of example, but other transgenes may also be included in the adenoviral vectors of the invention.

Von Willebrand disease (VWD)—the large transgene encoding von Willebrand factor (vWF; Accession No. FLJ75522) cannot be delivered by e.g. adeno-associated virus vectors due to its size. The adenovirus vectors of the present invention can be used to achieve endothelial cell-specific vWF expression (endothelial cells are the natural producer cell type of vWF). For example, vectors based on HAdV D17, which have an endothelial cell tropism, can be used for endothelial cell-specific vWF expression.

Coagulation factor VIII (FVIII) deficiency/haemophilia A—the large transgene encoding FVIII (Accession No. NM_000132) can be delivered using the high-capacity adenoviral vectors of the invention. The transgene can be subsequently mobilised for somatic integration into the host genome using the high-capacity adenovirus/Sleeping Beauty hybrid vectors.

Beta-thalassemia—the haemoglobin gene (Accession No. NC_000023) can be included in the adenovirus vectors of the invention to treat the haemoglobin deficiency that causes beta-thalassemia.

Muscular dystrophy—Dystrophin gene (DMD) (Accession No. NC_000023).

Cystic fibrosis—cystic fibrosis (CF) gene (Accession No. NM_000492).

Adenoviral Helper Vectors

Adenoviral helper vectors are used in conjunction with the high-capacity adenoviral vectors of the invention to facilitate their construction and propagation. The helper adenovirus provides all or most of the required early and late proteins necessary for replication.

Typically, the helper vector has loxP sites or FRT sites flanking the packaging signal such that packaging of the helper vector is avoided, resulting in preferential packaging of the high-capacity adenoviral genome.

In one embodiment, the invention provides an adenoviral helper vector comprising a sequence selected from SEQ ID NOs:1-13 and 18-32, or a sequence at least 50% identical thereto, that lacks the E1 region and comprises loxP sites (SEQ ID NO:221) or FRT sites (SEQ ID NO:222), wherein the loxP or FRT sites are positioned such that the first is downstream of the part of the sequence corresponding the positions defined in Table 1, column 3, respectively, and the second is upstream of the position of the deleted E1 region and downstream of the part of the sequence corresponding to the positions defined in Table 1, column 4, respectively.

In one embodiment, the invention provides an adenoviral helper vector comprising a sequence selected from SEQ ID NOs:1-13 and 18-32, or a sequence at least 50% identical thereto, that lacks the E1 region and comprises loxP sites (SEQ ID NO:221) or FRT sites (SEQ ID NO:222), wherein the loxP or FRT sites are positioned such that the first is downstream of the part of the sequence corresponding to SEQ ID NOs:65-77 and 82-96, respectively, and the second is upstream of the position of the deleted E1 region and downstream of the part of the sequence corresponding to SEQ ID NOs:33-45 and 50-64, respectively.

Preferably, the sequence is at least 60%, 70%, 80%, 85%, 90%, 95%, 96%, 97%, 98%, 99%, 99.5% or 99.9% identical to a sequence selected from SEQ ID NOs:1-13 and 18-32.

Hybrid helper vectors may be constructed as described above for the first-generation vectors of the invention.

Adenoviral Vaccine Vectors

Adenoviral vectors can also be used as vaccine vectors to deliver and express transgenes from a pathogen to raise an immune response. Adenoviral vectors tend to induce strong humoral and especially strong T cell responses to the expressed antigen[25].

Adenoviral vaccine vectors can be replication-competent or replication-deficient. The immune response varies depending on the adenovirus serotype, and consequently the protection efficiency against the vaccine antigen may be improved using adenoviral vectors based on adenoviruses from the different serotypes forming part of the library disclosed herein[24].

Replication-competent adenovirus vectors have the E3 gene deleted and replaced by heterologous DNA. The antigen may be expressed as part of an antigen expression cassette (e.g. under the control of a constitutive or inducible promoter), or via a bicistronic IRES sequence or a P2A peptide in the context of an early or late adenovirus transcription unit. Preferably, an antigen expression cassette is inserted into the E3 region. This may be done, for example, using the strategy described in Example 1 for the GFP/luciferase tagged adenoviruses. Further information regarding adenovirus vectors for use in vaccination may be found in reference 25, which is incorporated herein by reference.

Accordingly, in one embodiment, the invention provides an adenoviral vaccine vector comprising a gene encoding and capable of expressing an antigen. The vaccine vector may be a first generation adenoviral vector as described above, or a high-capacity adenoviral vector as described above.

The antigen may be from any pathogen, but is preferably from human immunodeficiency virus (HIV), Ebolavirus, Zika virus, hepatitis B virus, hepatitis C virus, influenza virus, *Mycobacterium tuberculosis*, or *Plasmodium falciparum*.

Suitable HIV antigens include (but are not limited to) Gag, Pol and Nef[26]. Suitable Ebolavirus antigens include the EBOV glycoprotein[27]. Suitable Zika virus antigens include Zika virus glycoproteins. Suitable hepatitis B antigens include the surface antigen (HBsAg). Suitable hepatitis C antigens include N53-5B[28]. Suitable influenza virus antigens include neuraminidase (NA), hemagglutinin (HA), nucleoprotein (NP) and matrix protein (MP).

Producer Cell Lines

The adenovirus vectors and helper vectors of the invention may lack the E1 region. However, this region contains genes necessary for viral replication, and so E1-expressing cell lines are required in order to generate adenoviral particles for delivery of the vectors to cells.

Accordingly, in one embodiment, the invention provides a cell encoding, and capable of expressing, an adenoviral E1 region derived from SEQ ID NO:1-3, 5-8, 10-12, 14-15, 17-25 or 27-32, or a sequence at least 70% identical to said E1 region. Such cells are used for producing adenovirus vectors according to the invention.

Preferably, the sequence is at least 80%, 85%, 90%, 95%, 96%, 97%, 98%, 99%, 99.5% or 99.9% identical to the adenoviral E1 region derived from SEQ ID NO:1-3, 5-8, 10-12, 14-15, 17-25 or 27-32.

In some embodiments, the invention provides a eukaryotic cell that has been transfected with an adenovirus vector as described herein that has been released from the adenovirus plasmid by restriction enzyme digestion.

The cell may further be capable of expressing Cre recombinase (Accession No. P06956) or Flp recombinase (Accession No. P03870). This is useful when using a helper vector in which the packaging signal is flanked by loxP or FRT sites, respectively, to allow preferential packaging of the helper-dependent vector over the helper vector, as discussed above.

Preferred cell lines include HEK293, HeLa and A549, but other cells can also be used.

Oncolytic Adenoviral Vectors

Oncolytic adenoviruses can be used in cancer therapy. Selective replication of these viruses in cancer cells can lead to killing of infected cells by virus-mediated cytolysis, and spreading to neighbouring tumour cells to continue the oncolytic process.

Oncolytic adenoviral vectors should be replication competent. That is, the oncolytic adenovirus should still be able to assemble and release new virus particles to infect neighbouring cells. Therefore it should contain at least all essential genes (transcription units E1, E2, E4 and L1-L5). E1 and E2, which are mainly responsible for virus replication, can be mutated or partially deleted to enhance replication efficiencies or to render the recombinant virus tumour-specific.

In one embodiment, the invention provides an oncolytic adenoviral vector comprising an E1 region derived from SEQ ID NOs:1-8, 10-12, 14-15, 18-25 or 27-32, or a sequence at least 70% identical to said E1 region. Preferably, the sequence is at least 80%, 85%, 90%, 95%, 96%, 97%, 98%, 99%, 99.5% or 99.9% identical to said E1 region.

Preferably, the oncolytic vector further comprises:
a) an E2 region derived from SEQ ID NOs:1-8, 10-12, 14-15, 18-25 or 27-32, or a sequence at least 70% identical to said E2 region;
b) an E4 region derived from SEQ ID NOs:1-8, 10-12, 14-15, 18-25 or 27-32, or a sequence at least 70% identical to said E4 region;
c) an L1 region derived from SEQ ID NOs:1-8, 10-12, 14-15, 18-25 or 27-32, or a sequence at least 70% identical to said L1 region;
d) an L2 region derived from SEQ ID NOs:1-8, 10-12, 14-15, 18-25 or 27-32, or a sequence at least 70% identical to said L2 region;
e) an L3 region derived from SEQ ID NOs:1-8, 10-12, 14-15, 18-25 or 27-32, or a sequence at least 70% identical to said L3 region;
f) an L4 region derived from SEQ ID NOs:1-8, 10-12, 14-15, 18-25 or 27-32, or a sequence at least 70% identical to said L4 region; and
g) an L5 region derived from SEQ ID NOs:1-8, 10-12, 14-15, 18-25 or 27-32, or a sequence at least 70% identical to said L5 region.

Preferably, the degree of sequence identity is at least 80%, 85%, 90%, 95%, 96%, 97%, 98%, 99%, 99.5% or 99.9%, for each of the regions.

The E1 and/or E2 region of the oncolytic vector may be mutated or partially deleted to enhance replication efficiency and/or tumour specificity (e.g. specificity of replication in tumour cells). For example, for achieving tumour cell specificity, a deletion may be made in the early gene E1B that inactivates p53. Suitable deletions have been made in HAd5-based vectors (ONYX-015 and H101); however, any deletion in E1B that has the effect of inactivating p53 may be used. Such viruses are useful in p53-functional cells. Alternatively, or in addition, oncolytic adenoviruses may contain a 24 bp deletion in the CR2 region of the DA region (as in AdΔ24). This mutation helps to restrict replication to cancer cells with mutated pRb (retinoblastoma protein). Further details of these and other mutations to enhance replication specificity can be found in reference 29 and the references cited therein (which are incorporated herein by reference).

Part or all or the E3 region may also be mutated or deleted to enhance antitumour effects. For example, deletion of the E3B gene enhances antitumour effects in immunocompetent mice[30].

The serotype from which viral sequences are derived may also be chosen to maximise replication. For example, vectors based on the hAd6 sequences disclosed herein appear to have enhanced oncolytic activity relative to human adenovirus 5 (see Example 6). Without being bound by any particular theory, it is thought that this enhanced oncolytic activity may be the result of enhanced replication. Vectors with enhanced replication or enhanced oncolytic activity relative to human adenovirus 5 are particularly preferred. The use of vectors comprising the Ad6 sequence in embodiments which comprise oncolysis is therefore encompassed by the present invention.

Besides directly genetically modifying adenoviral genes as discussed above, the virus can be armed using genes which enhance tumour cell killing or replication. Enhancing replication and production of new progeny is highly desirable, as in many cases virus-induced cell killing is not efficient enough.

The oncolytic vectors of the invention may further comprise:
a) a gene that enhances replication;
b) an immune-modulatory transgene;

c) a suicide gene or an interfering nucleic acid that enhances cell killing;
d) a gene or interfering nucleic acid that renders cells more sensitive to apoptosis or therapy with other drugs;
e) a tumour- or tissue-selective promoter; and/or
f) a gene for modulation of the tumour microenvironment.

a) Genes that Enhance Replication

Replication can be enhanced by adding e.g. the P19 gene (Accession number: Q712F9) to oncolytic vectors of the invention[31].

b) Immune-Modulatory Transgenes

Immunostimulatory genes can recruit immune cells to tumours and activate them. Recruitment of the immune system helps to destroy the primary tumour as well as having the potential to act on and clear metastatic cells. Genes encoding cytokines such as monocyte chemotactic protein 3 (MCP3) or granulocyte-macrophage colony-stimulating factor (GM-CSF) can be included in the oncolytic vectors. Other cytokines also result in enhanced immune responses and antitumour toxicity, for example tumour necrosis factor alpha (TNFα) and interferon gamma (IFNγ). Various interleukins and heat shock proteins can also be used[33].

c) Suicide Genes and Interfering Nucleic Acids that Enhance Cell Killing

Genes which enhance cell killing allow greater efficacy, as viruses can more easily escape from infected cells and infect neighbouring tumour cells. "Suicide genes" that encode prodrug-converting enzymes that convert non-toxic prodrugs to toxic products, are particularly effective as the toxic products can lead to killing of neighbouring, non-infected cells. For example, the herpes simplex virus thymidine kinase gene (HSV-TK) can be used in combination with ganciclovir, and/or cytosine deaminase (CD) can be used in combination with 5' fluorocytosine[33].

d) Genes or Interfering Nucleic Acids that Render Cells More Sensitive to Apoptosis or Therapy with Other Drugs Genes that render cells more sensitive to apoptosis allow greater efficacy in killing of tumour cells. For example, human tumour suppressor genes such as p53, or viral genes which stimulate cell senescence such as the Ad death protein (E3-11.6K) may be incorporated into vectors of the invention. The Ad death protein also enhances viral spread. Other human genes that can be used include suppressor of cytokine signalling 3 (socs3), second mitochondria-derived activator of caspases (Smac), X-linked inhibitor of apoptosis protein (XIAP)-associated factor 1 (XAF1), antioxidant enzyme manganese superoxide dismutase (MnSOD), and TNF-related apoptosis-including ligand (TRAIL). Interfering nucleic acids against antiapoptotic proteins can also be used. For example, antisense RNAs against cellular checkpoint proteins (e.g. polo-like kinase 1 (plk1), checkpoint kinase 1 (chk1) and checkpoint kinase 2 (chk2)), or small interfering RNAs (siRNAs) against the oncogene K-ras have previously been used to enhance antitumour effects[33]. Some of these genes and interfering nucleic acids result in induced synergistic oncolytic effects when combined with chemotherapeutic agents such as 5-fluorouracil and cisplatin[33].

e) Tumour- or Tissue-Selective Promoters

Tumour or tissue-selective promoters allow further specificity of replication in tumour cells. For example, CN706 has a prostate-specific antigen promoter-driven E1 cassette, which allows selective, androgen-dependent replication in prostate cells[32].

f) Genes for Modulation of the Tumour Microenvironment

Tumours rely on processes such as angiogenesis and modulation of the extracellular matrix, and so disruption of these processes can have antitumour effects. Accordingly, the oncolytic vectors may carry transgenes that act on extracellular matrix components, such as tissue inhibitor of metalloproteinase 3 (TIMP3), or transgenes that inhibit angiogenesis, such as endostatin, Flt-1 (a VEGF inhibitor), or interfering RNAs targeted against angiogenesis-promoting factors such as VEGF.

The above transgenes may be placed under the control of endogenous viral gene control elements, or may be under the control of exogenous promoters. Exogenous promoters may be constitutive or inducible. Further details of suitable transgenes and promoters as discussed above can be found in references 29 and 33 and the references cited therein (which are incorporated by reference herein).

As noted above, the fiber gene region is primarily responsible for cell tropism. If the target tumour cells express a receptor to which a fiber protein from the adenoviral library binds, an oncolytic vector can be based on this adenoviral serotype, or a hybrid oncolytic vector may be constructed comprising only the fiber gene (or the shaft and knob regions thereof) from said adenoviral serotype, as described above for the first-generation vectors of the invention.

Pharmaceutical Compositions

The invention also provides pharmaceutical compositions comprising the adenoviral vectors of the invention, including vectors for use in gene therapy, vaccine vectors and oncolytic vectors. The pharmaceutical compositions comprise the vector of the invention and a pharmaceutically-acceptable carrier.

The pharmaceutical compositions of the invention may comprise further excipients.

For example, a pharmaceutical composition comprising an oncolytic adenoviral vector of the invention may comprise a polymer or polyethylene glycol coating for the oncolytic vector. This may aid immune evasion and increase delivery to the tumour[34,35].

Compositions of the invention may comprise further therapeutic agents in addition to the adenoviral vector. For example, compositions comprising an oncolytic vector may comprise one or more further chemotherapeutic agents (e.g. 5-fluorouracil and cisplatin), particularly if the oncolytic vector increases susceptibility to therapy with other drugs.

Methods of Treatment/Use in Therapy

The adenoviral vectors or the oncolytic adenoviruses of the invention may be used in therapy. The invention also provides a method of treatment comprising administering an adenoviral vector of the invention to a patient.

For example, adenoviral vectors of the invention may be used in gene therapy. Such vectors include a transgene, for example the transgenes discussed above for the treatment of von Willebrand disease, haemophilia A, beta thalassemia, muscular dystrophy and cystic fibrosis. However, the invention is not limited to treatment of these disorders, and in principle, the vectors of the invention can be used to treat any genetic disorder in which replacement of a mutant allele with a non-mutant copy could restore physiological function. Vectors for use in gene therapy include the first generation adenoviral vectors and the high-capacity adenoviral vectors described above. Where stable integration of transgenes would be beneficial, the adenovirus-Sleeping Beauty hybrid vectors of the invention can be used. The CRISPR/Cas9 high-capacity vectors can be used to facilitate in vivo gene correction to treat genetic diseases, as discussed above.

In addition, the CRISPR/Cas9 vectors of the invention can be used to treat infectious diseases, for example as an antiviral approach to cut and destroy viral genomes.

Adenoviral vaccine vectors of the invention can be used as prophylactic and/or therapeutic vaccines. Vaccine vectors can be used to protect against various diseases, for example including HIV, Ebola, Zika virus disease, hepatitis B, hepatitis C, influenza, tuberculosis or malaria.

Oncolytic vectors of the invention can be used to treat conditions involving the formation of benign and/or malignant tumours, including cancer. For example, the oncolytic vectors can be used to treat carcinoma (e.g. squamous cell or nasopharyngeal), colorectal cancer, hepatocellular carcinoma, lung cancer, mesothelioma, prostate cancer, breast cancer, ovarian cancer, bladder cancer, glioma etc.

The vectors of the invention may be administered locally or systemically. Systemic administration may include intravenous, intraarterial, intraperitoneal, intramuscular, intramuscular or subcutaneous administration. The vectors may be administered mucosally (e.g. orally or nasally). Local administration can include e.g. local delivery to target tissues for gene therapy (e.g. intrapleurally), or intratumoral or intracavitary delivery for oncolytic adenoviruses.

Vectors for use in therapy may be administered in conjunction with other therapeutic agents, either as part of the same composition, or as separate compositions administered together or sequentially. For example, treatment with an oncolytic vector may be administered in conjunction with other chemotherapeutic agents (e.g. 5-fluorouracil and cisplatin), or may be used in conjunction with e.g. radiotherapy.

Methods of diagnosis are also provided by the invention. Advantageously, a method for determining whether an adenovirus is present in a sample, as described herein, may be used for determining whether a disease is being caused by an adenoviral infection. Thus, the invention further provides a method for diagnosing a disease, e.g. an infection, as being caused by an adenovirus, comprising carrying out a method as described above, wherein the sample is a clinical sample from the patient (e.g. blood, saliva, urine or serum) or genomic DNA derived from the sample. In some embodiments the patient is selected from a human or non-human mammal, for example, horse, dog, cat, cow, goat, sheep, rabbit, mouse, rat or guinea pig. In some embodiments, the patient is a human. The invention further provides a method for determining the identity of an adenovirus in a patient sample by carrying out a method as described above. In some embodiments, the disease is selected from a disease of the respiratory tract, eye, intestine, urinary tract and nervous system. In some embodiments, the disease of the respiratory tract is a respiratory infection, for example, bronchiolitis, croup, or viral pneumonia. In some embodiments, the disease of the intestine is gastroenteritis or diarrhea. In some embodiments, the disease of the eye is conjunctivitis, pharyngoconjunctival fever, or keratoconjunctivitis. In some embodiments, the disease of the urinary tract is a urinary tract infection or hemorrhagic cystitis. In some embodiments, the disease is meningitis or encephalitis. In some embodiments the disease is febrile respiratory disease.

Methods of Generating Adenoviral Vectors

The invention provides a method of generating an adenoviral vector or helper vector as defined above. This includes methods of producing the vaccine vectors or oncolytic vectors as defined above.

In one embodiment, a method of generating an adenoviral vector comprises cloning an adenoviral sequence using linear to linear homologous recombination (LLHR). In one embodiment, the invention provides a method for cloning an adenoviral sequence, comprising:
  a) providing a sample comprising a first linear nucleic acid molecule which is an adenoviral genome;
  b) providing a linearized plasmid which shares at least two regions of sequence homology with the first nucleic acid molecule; and
  c) bringing the first nucleic acid molecule and the linearized plasmid into contact in the presence of a 5' to 3' exonuclease and an annealing protein such that the first linear nucleic acid and the linearized plasmid recombine to form a circular plasmid containing an adenoviral sequence.

In some embodiments, the adenoviral sequence is an adenoviral sequence as disclosed herein. In one embodiment the first linear nucleic acid molecule comprising an adenoviral sequence is present in a biological fluid obtained from a human or other non-human mammal. In some embodiments, the sample is blood, serum, spinal fluid, saliva and/or urine. In some embodiments, the sample is a mixture. In some embodiments, the sample is a clinical sample. This mixture may, in some embodiments, comprise adenoviral genomic DNA and eukaryotic genomic DNA, for example human genomic DNA. Advantageously the method of the present invention allows adenoviruses to be cloned directly from a biological sample without requiring a step of purifying the DNA before carrying out the cloning step. For example, instead of using a purified adenovirus genome, a DNA mixture isolated from cell/virus lysate can be used. In some embodiments, the method further comprises a step of amplifying the adenovirus in a cell line before lysing the cells. Thus, in some embodiments, the first linear nucleic acid molecule is present in a cell/virus lysate or is present in a DNA mixture isolated from cell/virus lysate. In some embodiments, the method involves co-electroporating the first linear nuclear molecule present in a mixture isolated from cell/virus lysate into a host cell together with the plasmid of step b) such that homologous recombination can occur. In some embodiments, the method comprises a step of phenol-chloroform extraction to isolate the adenoviral DNA from the sample. In some embodiments, the phenol-chloroform extraction involves taking the interphase protein-DNA complexes. In some embodiments, the mixture comprising adenoviral DNA is treated with proteinase K. In some embodiments, viral genomic DNA is extracted, e.g. from purified particles, by the addition of proteinase K, subsequent phenol-chloroform extraction, and ethanol precipitation.

In some embodiments, less than 2 ug (e.g. less than 1.75 ug, less than 1.5 ug, less than 1.25 ug) viral genomic DNA is used in the cloning method. In some embodiments, more than 200 ng (e.g. more than 300 ng, 500 ng, 700 ng, 800 ng, 900 ng) viral genomic DNA is used in the cloning method. In some embodiments, the amount of plasmid vector used in the cloning method is about the same as the amount of viral genomic DNA. For example, in some embodiments, about 1 ug viral genomic DNA is used in the cloning method together with about 1 ug plasmid vector. As shown in FIG. 2, very good efficiencies of homologous recombination are obtained using these amounts.

In embodiments in which it is desired to clone an adenovirus of unknown sequence, the method may comprise amplifying the adenovirus in a cell line, lysing the cells and purifying the virus from the crude cell lysate, e.g. by CsCl gradient, followed by viral genome isolation and sequence verification. Once the sequence of the ITR regions has been obtained, the method of cloning described herein can be used to clone the full length adenovirus. However, as there is often a degree of sequence homology between the ITR regions of different adenoviruses, it is possible to use a plasmid that has been designed to have sequence homology to the ITRs of one adenovirus to clone a different adenovirus, and the present invention also encompasses such embodiments.

The direct cloning method described herein advantageously provides a more efficient and quicker method for cloning full length adenoviral genomes than was previously available. Previously, most adenoviral cloning techniques involved modularly cloning regions of adenoviral genes and stitching them together in a BAC vector. Other studies which used homologous recombination based techniques to clone adenoviral genomes into plasmids used highly inefficient techniques which required long homology arms and pure concentrated forms of adenoviral DNA. For example, Renault et al. (Virol. Methods 2002) uses *E. coli* Top10F', which is an *E. coli* strain that utilizes endogenous recA minus recombination, which is very inefficient.

Preferably, the linearized plasmid is designed so that it comprises a region of sequence homology with the 5' ITR of the adenoviral sequence in the first linear nucleic acid molecule and a region of sequence homology with the 3' ITR of the adenoviral sequence in the first linear nucleic acid molecule. In some embodiments, the region of homology is about 50 nt in length, for example, 50 nt, 50-55 nt, 50-60 nt, 50-70 nt, 45-50 nt, 40-50 nt, 30-50 nt, 45-55 nt, 40-60 nt, 30-70 nt or 40-80 nt in length. The skilled person will understand how to design the regions of sequence homology with a sufficient amount of sequence homology for homologous recombination to take place. In some embodiments, the region of sequence homology is 100% identical with the respective region of the adenoviral sequence. In some embodiments, there is a lesser degree of sequence identity (e.g. more than 90%, more than 95%, more than 98%), but there is sufficient sequence homology for homologous recombination to occur. This enables a plasmid vector designed to clone a first adenovirus to be used to clone a second adenovirus whose ITR regions share sufficient sequence homology with the first adenovirus. In some embodiments, the region of homology is only to a part of the ITR sequence rather than to the full length ITR sequence. In some embodiments, the region of homology is to the whole length of the ITR sequence. The 5' ITR and 3' ITR sequences are at the 5' and 3' ITR of the adenoviral genome and so designing the linearized plasmid so that these are the regions to be recombined ensures that the full length genome is cloned into the plasmid backbone. It would be straightforward for the skilled person to obtain the 5' and 3' ITR sequences from an adenoviral genome sequence, for example, from an adenoviral genome sequence as disclosed herein. In some embodiments, the 5' and 3' ITR sequences are from an adenoviral genome sequence as presented in Table 1, columns 3 and 5 respectively.

Accordingly, in some embodiments, the first linear nucleic acid molecule comprises a full length adenoviral genome sequence. In some embodiments, such a sequence will be present in the sample because of the presence of adenovirus in the sample. Preferably, the adenoviral sequence is the full length adenoviral genome sequence contained within any one of SEQ ID Nos 1-32 and/or 1411, for example, contained within any one of SEQ ID Nos 1-15, 17-32 and/or 1411 or contained within any one of SEQ ID NOs: 1-3, 5-8, 10-12, 14-15, 17-25 and 27-32 and/or 1411, or contained within any one of SEQ ID NOs: 1-3, 5-8, 10-12, 14-15, 17-25 and 27-32, or a sequence at least 50% identical thereto.

In preferred embodiments, the circular plasmid formed in step c) comprises a full length adenoviral genome sequence. However, in some embodiments, the adenoviral genome sequence cloned into the circular plasmid in step c) is missing one or more nucleotides at its 5' and/or 3' ends because one or both regions of sequence homology did not extend all the way to the 5' and/or 3' terminus, respectively, of the ITR sequence. For example, in some embodiments, the adenoviral genome sequence is missing less than 3, 5, 10, 15, 20, 25, 30, 35, 40, 50, 75, 100, 125 or 135 nucleotides from its 5' and/or 3' ends.

Accordingly, in a preferred embodiment there is provided a method for cloning an adenoviral genome sequence, comprising:
  a) providing a sample comprising a first linear nucleic acid molecule which is an adenovirus, wherein the sample has not been subjected to a step of DNA purification;
  b) providing a linearized plasmid which shares at least two regions of sequence homology with the first nucleic acid molecule, wherein the first and second regions of homology are to the 5' ITR and 3' ITR of the adenovirus of part a); and
  c) bringing the first nucleic acid molecule and the linearized plasmid into contact in the presence of a 5' to 3' exonuclease and an annealing protein such that the first linear nucleic acid and the linearized plasmid recombine to form a circular plasmid containing the adenoviral genome sequence.

Any suitable linearized plasmid may be used. In some embodiments, the linearized plasmid comprises homology arms (HA) for directed cloning containing the 5' and 3' ITR sequences, one or more selection markers and an origin of replication. In some embodiments, the linearized plasmid comprises homology arms (HA) for directed cloning containing the 5' and 3' ITR sequences, one or more selection markers (e.g. the chloramphenicol resistance gene) and an origin of replication (e.g. the p15a origin). In some embodiments, the linearized plasmid comprises homology arms (HA) for directed cloning containing the 5' and 3' ITR sequences, one or more selection markers (for example, ccdB10 and ampicillin for advanced positive and counter selection), an origin of replication (e.g. p15A) and an antibiotic resistance gene (e.g. the chloramphenicol resistance gene). In some embodiments, the linearized plasmid is selected from a p15A origin-based vector, a pBR322 origin-based vector, a fosmid, a pUC origin-based vector or a ColE1 origin-based vector. Medium copy plasmids are preferred, for example, p15A, pBR322, pR6K, pRK2, pBBR1 and Inc-based plasmids, in particular p15A origin-based vectors. In some embodiments, the medium copy plasmid is p15A-cm-adHA, as described herein. In some embodiments, the plasmid is present in about 10 copies in each cell, for example 10 copies, 9-11, 8-12, 8-11 or 6-12 copies. Preferably, the plasmid used for cloning the adenovirus genome sequence is not a BAC. In some embodiments, the plasmid is a shuttle vector. In some embodiments the plasmid is less than 4 kb in length, for example, less than 3.5 kb, 3 kb, 2.5 kb, 2 kb, 1.5 kb or 1 kb in length.

Cloning the adenoviral genome into a medium copy plasmid provides a number of advantages compared to prior art methods which involved cloning adenoviral sequences into low copy BACs. For example, the present adenoviral plasmids allow a higher concentration of adenoviral vector to be obtained and increase the efficiency of transfection of the released adenovirus vectors into cells. The plasmid backbones described herein are more stable than the prior art backbones and make it possible to clone complete adenovirus genomes in a high-throughput manner without introducing recombinations or mutations into the cloned viral genome. The increased efficiency of the present method means the number of clones that need to be screened to find a correct recombinant is greatly reduced compared to the prior art methods which often required screening of around 400 clones. Advantageously, the cloning methods described herein make it possible to create a library of adenoviral genome sequences and adenoviral vectors, which was simply not feasible using the previous techniques.

Using a medium copy plasmid, such as a p15A origin plasmid, has a number of advantages compared to BACs. For example, medium copy plasmids such as p15A can be more stable than BACs. As another example, the medium copy plasmid makes the first cloning step easier become the homology arms can be ordered as oligonucleotides and attached to the plasmid by PCR in one or two steps, whereas each homology arm must be cloned into the BAC individually to generate a dedicated plasmid that then must be linearized. In addition, medium copy plasmids such as p15A may result in at least 10-time increased plasmid yields isolated from *E. coli* bacteria compared to that obtained using a BAC. Increased plasmid yields after plasmid purification compared to BAC purification procedures makes the first step of virus production (=transfection of DNA into the producer cell line) more feasible, because a sufficient amount is needed. In general the increased stability and efficiency enables high-throughput work which is in sharp contrast to conventional methods used for adenovirus genome cloning.

In some embodiments, the plasmid of step b) is linearized prior to electroporating it into a host cell in which homologous recombination occurs. In other embodiments, the plasmid of step b) is linearized in vivo, for example, using a rare site sequence-specific cutting enzyme, for example as described in reference 20.

Any suitable 5' to 3' exonuclease and annealing protein may be used. Preferably, the 5' to 3' exonuclease is full-length RecE (SEQ ID NO:1412) as described in reference 20 (incorporated herein by reference), or a protein with at least 70% sequence identity to the full-length form (preferably at least 80%, 85%, 90%, 95%, 96%, 97%, 98%, 99%, 99.5% or 99.9%) which retains the 5' to 3' exonuclease activity. The annealing protein is preferably RecT.

In some embodiments, the method comprises co-electroporating the first linear nucleic acid molecule and the linearized plasmid into a host cell that expresses full length RecE and RecT. In some embodiments, the method is carried out in a host cell in which full-length RecE is expressed under the control of an inducible promoter. In some embodiments, the host cell is an *E. coli* cell, for example, *E. coli* strain GBRed. Examples of suitable host cells are well known in the art, and are described in detail in reference 20. In some embodiments, the host cell expresses RecA and/or Red gamma.

Methods of direct cloning utilising full length RecE and RecT are described in detail in reference 20, which is hereby incorporated by reference in its entirety. Previous attempts to clone Herpes viruses using direct cloning have failed and so it is surprising that direct cloning works with adenoviruses.

In some embodiments, following the step of cloning the adenoviral genome, a step of sequencing is carried out to determine the sequence of the adenovirus.

In some embodiments, following the step of cloning the adenoviral genome, the method further comprises checking the integrity of the cloned adenoviral genome, for example, using diagnostic restriction enzyme digest and/or next generation sequencing.

In another aspect, the invention provides a cloning method as described herein to clone a viral genome sequence, preferably, a double stranded DNA viral genome sequence. In some embodiments, the virus is not an adenovirus. In some embodiments, the virus has a genome which is less than 70 kb in length, e.g. less than 65 kb, 60 kb, 55 kb, 50 kb, 45 kb, 40 kb or 35 kb in length. In some embodiments, the virus has a genome which is more than 10 kb in length, for example, more than 12 kb, 15 kb, 20 kb, 25 kb or 30 kb in length. For example, in some embodiments, the virus is between 10-70 kb in length, e.g. 15-70 kb, 15-60 kb, 20-60 kb, 20-55 kb, 20-45 kb, 25-55 kb, 25-45 kb or 35-45 kb in length. Similarly, the other methods and vectors may be used for other types of viruses. The skilled person would understand how to adapt the methodology and products described herein for different types of viruses.

The invention further provides a plasmid vector comprising a full length adenoviral genome sequence. Preferably, the plasmid has been obtained by or is obtainable by a method as described herein. Accordingly, the description provided of the adenoviral sequences and the plasmid vectors in the methodology described herein can be extrapolated to this aspect of the invention which is the plasmid vectors comprising the cloned adenoviral sequences. In some embodiments, the plasmid comprises a full length adenoviral genome sequence as described herein. For example, in some embodiments, the plasmid comprises the full length adenoviral genome sequence contained within any one of SEQ ID NOs 1-32 or 1411, or a sequence at least 70% identical thereto (preferably at least 80%, 85%, 90%, 95%, 96%, 97%, 98%, 99%, 99.5% or 99.9%). In some embodiments, the plasmid comprises the genome sequence contained within any one of SEQ ID NOs: 1-3, 5-8, 10-12, 14-15, 17-25, 27-32 and 1411, or a sequence at least 70% identical thereto (preferably at least 80%, 85%, 90%, 95%, 96%, 97%, 98%, 99%, 99.5% or 99.9%). In some embodiments, the plasmid comprises an adenoviral genome that has not previously been sequenced.

In some embodiments, the plasmid which contains the adenoviral sequence is a medium copy plasmid which comprises an origin of replication and a selectable marker such as an antibiotic resistance gene. In some embodiments, the plasmid comprises the p15A origin. In some embodiments, the plasmid is a medium copy plasmid which comprises an origin of replication, a selection marker and a full length adenoviral genome sequence, wherein the plasmid additionally comprises one or more restriction sites immediately upstream and immediately downstream of the adenoviral genome sequence, such that the adenoviral genome vector can be released from the plasmid vector. As mentioned above, in an alternative aspect of the invention, the plasmid comprises a full length viral genome sequence, which in some embodiments is not an adenoviral sequence. For example, the full length viral genome sequence may be from polyomaviruses or papillomaviruses.

The invention further provides a library of cloned adenoviral genomes. Preferably, the adenoviral genomes are full length adenoviral genomes. Thus, the invention provides a library of two or more (e.g. 2, 3, 4, 5, 6, 7, 8, 9, 10, 15, 20 or more) plasmid vectors each comprising a full length adenoviral genome sequence. Preferably, the two or more plasmid vectors have been obtained by or are obtainable by a cloning method as described herein. In some embodiments, the library comprises sequences of at least two (e.g. 2, 3, 4, 5, 6, 7, 8, 9, 10, 15, 20) different adenoviruses. For example, in some embodiments, there is a provided a library comprising two or more of the plasmid vectors comprising a full length adenoviral genome sequence that are described herein. In some embodiments, the cloned adenoviruses in the library are tagged with a reporter gene.

In another aspect, there is provided a plasmid that is suitable for use in step b) of the cloning method. The plasmid may be provided in circular form or in linearized form. For example, in some embodiments, the invention provides a plasmid comprising an origin of replication, a selection marker, and two regions of homology with the ITR regions of an adenoviral genome sequence, wherein one region has homology to the 5'ITR and a second region has homology to the 3'ITR. The descriptions of the plasmids for use in the cloning method of the invention can be extrapolated to this aspect of the invention. For example, in some embodiments, the plasmid is a medium copy plasmid such as a p15A, pBR322, pR6K, pRK2, pBBR1 or an Inc-based plasmid. In some embodiments the plasmid of this aspect of the invention will contain less than 1000 nt of adenoviral sequence, for example, less than 900, 800, 700, 600, 500, 400, 300, 250, 200, 150, 100, 50, 25, 15 or 10 nt.

The invention further provides a method for determining whether an adenovirus is present in a sample, comprising contacting the sample, or genomic DNA derived from the sample, with a linearized plasmid as described herein which comprises at least two regions of sequence homology with an adenoviral sequence in the presence of a 5' to 3' exonuclease and an annealing protein such that if an adenoviral genome sequence is present in the sample, it will recombine with the linear plasmid to form a circular plasmid containing an adenoviral sequence, and further comprising a step of determining whether a circular plasmid containing an adenoviral sequence has been formed. Advantageously, such a method may be carried out using a method for cloning an adenoviral sequence as described herein. In some embodiments, the linearized plasmid shares a region of sequence homology with the 5' ITR of an adenoviral sequence and shares a region of sequence homology with the 3' ITR of the adenoviral sequence. In some embodiments, the method further comprises the step of determining the identity of the cloned adenoviral sequence, for example, by sequencing all or part of the cloned adenoviral sequence and/or analysing the cloned adenoviral sequence using restriction enzyme digestion.

In some embodiments, the method comprises contacting a sample with a library of linearized plasmids comprising homology regions which have been designed to target different adenoviruses. In some embodiments, the method comprises contacting the sample with all the members of the library simultaneously. In some embodiments, the method comprises carrying out multiple experiments using individual members of the library. Thus, the invention further provides a library of plasmids that are suitable for use in step b) of a method for cloning as described herein, wherein the individual members of the library share regions of sequence homology with the 5' ITR and 3' ITR of different adenoviruses. In some embodiments, the library has at least 2, 3, 4, 5, 10, 15, 20, 25 or 30 members.

The invention also provides an adenoviral vector that has been released in linear form from the circular plasmid containing the adenoviral genome sequence, e.g. by restriction digestion, as described herein.

The method of generating a vector generally uses linear to circular homologous recombination (LCHR) to delete one or more regions of the adenoviral genome as discussed above. Accordingly, in one embodiment, the invention provides a method of generating an adenoviral vector or helper vector, comprising:

a) providing a first circular nucleic acid molecule comprising an adenoviral sequence selected from SEQ ID NOs: 1-32 and/or 1411, for example comprising a full adenoviral genome sequence selected from within any one of SEQ ID NOs 1-32 and 1411, or selected from within any one of SEQ ID NOs: 1-15 and 17-32 and 1411, or selected from within any one of SEQ ID NOs: 1-3, 5-8, 10-12, 14-15, 17-25 and 27-32, or a sequence at least 70% identical thereto (preferably at least 80%, 85%, 90%, 95%, 96%, 97%, 98%, 99%, 99.5% or 99.9%);

b) providing a second linear nucleic acid molecule which shares at least one region of sequence homology with the first nucleic acid molecule; and c) bringing the first and second nucleic acid molecules into contact in the presence of a 5' to 3' exonuclease and an annealing protein such that a deletion, mutation and/or insertion is introduced in the first nucleic acid molecule.

Preferably the first circular nucleic acid molecule described in step a) has been generated using the LLHR direct cloning method described above. Accordingly, the description of the adenoviral sequence and the plasmid vector described for the cloning method can be extrapolated to this aspect of the invention. Thus, there is also provided a plasmid vector as described herein which comprises the modified adenoviral genome sequence obtained by or obtainable by this method of the invention. In some embodiments, the plasmid vector comprises the sequence of an adenoviral vector as described herein.

The adenoviral vector can be released in linear form from the first circular nucleic acid molecule e.g. by restriction digestion. To release the genome by restriction digestion, the circular nucleic acid molecule will comprise restriction sites both 5' and 3' of the adenoviral sequence. Thus, in some embodiments, the linearized plasmid used in the cloning method comprises restriction sites 5' and 3' of the two regions of sequence homology (i.e. so that the resulting circular nucleic acid molecule comprising the cloned adenoviral sequence comprises the restriction sites 5' and 3' of the adenoviral sequence). Accordingly, in some embodiments, the released adenoviral vector does not comprise any plasmid sequence. In some embodiments, the released adenoviral vector comprises less than 1000 nt plasmid sequence at the 5' and/or 3' end, for example, less than 900, 800, 700, 600, 500, 400, 300, 250, 200, 150, 100, 50, 25, 15 or 10 nt.

Suitable deletions are discussed above in relation to the vectors (for example, the E1 region and/or the E3 region, and/or other early gene regions). For the high-capacity vectors, all coding sequences are deleted. For oncolytic vectors, non-essential sequences (e.g. E3 sequences) may be deleted. Alternatively, mutations may be made using the second linear nucleic acid, for example in the E1 and/or E2 region. Insertions may also be made, for example to insert a transgene or other non-adenoviral DNA, for example as discussed above. Usually, if DNA is inserted, at least some non-essential regions of the adenoviral genome are deleted to create coding capacity for the inserted DNA.

For a deletion or mutation, the linear nucleic acid may be less than 180 nucleotides in length (for example, 150 nucleotides or less, 130 nucleotides or less, 110 nucleotides or less, 100 nucleotides or less, 80 nucleotides or less, 60 nucleotides or less or 55 nucleotides or less).

In some embodiments, the second linear nucleic acid molecule shares at least two regions of sequence homology with the first nucleic acid molecule, where the regions of sequence homology have been designed to remove the intervening sequence that is present in the adenoviral sequence. For example, the sequence homology may be to either side of the E3 region to delete the entire E3 region.

Alternatively, the second nucleic acid molecule may be longer and comprise heterologous (non-adenoviral) DNA e.g. comprising one or more transgenes, between two regions of homology ("homology arms"). This leads to replacement of the deleted sequences between the homology arms in the first nucleic acid molecule with the heterologous DNA between the homology arms in the second nucleic acid molecule. Such methods are usually carried out in conjunction with a method of inserting one or more transgenes into a vector of the invention, as described below.

The first circular nucleic acid molecule may be e.g. a bacterial artificial chromosome (BAC), a p15A origin-based vector, a pBR322 origin-based vector, a fosmid, a pUC origin-based vector or a ColE1 origin-based vector. However, medium copy plasmids are preferred, for example, p15A, pBR322, pR6K, pRK2, pBBR1 and Inc-based plasmids, in particular p15A origin-based vectors.

Suitable 5' to 3' exonucleases include RecE[20] and Red alpha[36]. These exonucleases are used in conjunction with the annealing proteins RecT and Red beta, respectively. The RecE may be either full-length (SEQ ID NO:1412) or a truncated form (e.g. RecE588 or RecE602), as described in reference 20 (incorporated herein by reference), or a protein with at least 70% sequence identity to the full-length or truncated form (preferably at least 80%, 85%, 90%, 95%, 96%, 97%, 98%, 99%, 99.5% or 99.9%). The Red alpha/Red beta system is preferred. If RecE is used, truncated RecE is preferred.

In some alternative embodiments of generating a vector using linear to circular homologous recombination (LCHR) to delete one or more regions of the adenoviral genome, the first nucleic acid molecule described above which comprises the adenoviral sequence is linear (e.g. a linearized form of the circular nucleic acid molecule generated using the LLHR cloning method described herein, wherein the first nucleic acid is linearized either in vivo in the recombination-competent host cell, or is linearized in vitro) and the second nucleic acid is provided in circular form. The various embodiments described herein can be adapted to this alternative embodiment.

In some embodiments, the method of cloning using LLHR and the method of deleting one or more regions of the adenoviral genome using LCHR, as described above, are carried out in the same host cell. In some embodiments, the host cell expresses full length RecE under the control of an inducible promoter and either truncated RecE and/or Red alpha under the control of one or more different inducible promoters. In addition, in such embodiments, the host cell also expresses the corresponding annealing proteins RecT and Red beta, respectively. Advantageously, such a host cell allows independent temporal expression of the full length RecE/RecT system and the Red alpha/Red beta or truncated RecE/RecT system, such that the required recombination proteins can be activated at the point in time that they are required.

Methods of Generating Cells

The invention also provides a method of generating a cell as defined above. The method comprises transforming a cell with DNA encoding, and capable of expressing, at least an adenoviral E1 region selected from SEQ ID NOs:1-3, 5-8, 10-12, 14-15, 17-25 or 27-32, or a sequence at least 70% identical thereto (preferably at least 80%, 85%, 90%, 95%, 96%, 97%, 98%, 99%, 99.5% or 99.9%). Typically, the DNA encoding the E1 region also encodes a selectable marker (for example neomycin, puromycin, hygromycin etc.). The selectable marker allows detection of cells into which the DNA carrying the E1 region has integrated stably.

Means for expressing the E1 region and the selectable marker include e.g. an IRES or a promoter.

The method may also comprise transforming a cell with DNA encoding, and capable of expressing, Cre recombinase (Accession No. P06956) or Flp recombinase (Accession No. P03870). These cell lines are used when a helper vector is required.

Methods of Inserting Transgenes

The invention provides a method of inserting one or more transgenes into an adenoviral vector or helper vector according to the invention (including e.g. oncolytic or vaccine vectors). This method may be performed in conjunction with the method of generating an adenoviral vector as set out above.

In one embodiment, the invention provides a method of inserting one or more transgenes into an adenoviral vector or helper vector, comprising:

a) providing a first circular nucleic acid molecule comprising an adenoviral sequence selected from SEQ ID NOs:1-15 and 17-32, or for example comprising a full adenoviral genome sequence selected from within any one of SEQ ID NOs 1-32 and 1411, or selected from within any one of SEQ ID NOs: 1-15 and 17-32 and 1411, or selected from within any one of SEQ ID NOs: 1-3, 5-8, 10-12, 14-15, 17-25 and 27-32, or a sequence at least 50% identical thereto (preferably at least 60%, 70%, 80%, 85%, 90%, 95%, 96%, 97%, 98%, 99%, 99.5% or 99.9%);

b) providing a second linear nucleic acid molecule which shares at least two regions of sequence homology with the first nucleic acid molecule; and c) bringing the first and second nucleic acid molecules into contact in the presence of a 5' to 3' exonuclease and an annealing protein such that sequences between the regions of homology in the second nucleic acid molecule are introduced into the first nucleic acid molecule.

Preferably the first circular nucleic acid molecule described in step a) has been generated using the LLHR direct cloning method described above. Accordingly, the description of the adenoviral sequence and the plasmid vector described for the cloning method can be extrapolated to this aspect of the invention. Thus, there is also provided a plasmid vector as described herein which comprises the modified adenoviral genome sequence obtained by or obtainable by this method of the invention.

For vector production the adenoviral vector can be released in linear form from the first circular nucleic acid molecule e.g. by restriction digestion. To release the genome by restriction digestion, the circular nucleic acid molecule will comprise restriction sites both 5' and 3' of the adenoviral sequence.

The method may also involve a deletion of part of the adenoviral sequence, as discussed above.

The second linear nucleic acid molecule may comprise the transgene(s) of interest, such that the transgene(s) is/are inserted into the first nucleic acid molecule in one step. Alternatively, the method may be a two- or multi-step process in which the second linear nucleic acid molecule comprises e.g. a selectable marker, which is inserted into the first circular nucleic acid molecule in a first step. A second step is then carried out comprising (a) to (c) above, but with a third linear nucleic acid molecule in place of the second linear nucleic acid molecule. The third linear nucleic acid molecule carries the transgene(s) of interest, and comprises at least two regions of sequence homology with the intermediate circular nucleic acid molecule (which corresponds to the first circular nucleic acid molecule comprising sequence inserted from the second linear nucleic acid molecule).

In some embodiments, the at least two homology regions on the second linear nucleic acid molecule are designed to target the transgene to the E3 region of the adenoviral genome sequence. In some embodiments, inserting the transgene simultaneously results in deletion of sequence within the adenoviral genome sequence, e.g. the E3 region. In some embodiments, the transgene is inserted into a region corresponding to a deleted sequence in the adenoviral sequence, e.g. the deleted E3 region. In some embodiments, the transgene is inserted in the adenoviral sequence without deleting any adenoviral sequence.

Advantageously, the use of a method of inserting a transgene allows tagged adenoviral vectors to be generated. In some embodiments, the second linear nucleic acid molecule is designed to comprise homology regions to a region that is conserved between adenoviral sequences, e.g. a conserved region in the E3 region, such that different adenoviral genomes can be tagged in a high-throughput manner using identical plasmid vectors.

Suitable 5' to 3' exonucleases and annealing proteins include those described above for methods of generating the adenoviral vectors of the invention.

In some alternative embodiments of inserting one or more transgenes, the first nucleic acid molecule described above which comprises the adenoviral sequence is linear (e.g. a linearized form of the circular nucleic acid molecule generated using the LLHR cloning method described herein, wherein the first nucleic acid is linearized either in vivo in the recombination-competent host cell, or is linearized in vitro) and the second nucleic acid is provided in circular form. The various embodiments described herein can be adapted to this alternative embodiment.

Methods for Obtaining Packaged Vectors or Oncolytic Viruses

The adenoviral vector can be released in linear form from a circular nucleic acid molecule as described above, and the DNA vector purified using standard procedures. The linear DNA can be transfected into target cells for vector amplification. If the vector is replication-deficient, the cell line will be a "producer cell line" as described above, which complements for one or more essential genes missing from the adenoviral vector. If the vector is helper-dependent, then the helper vector is also transfected into the producer cell line.

Packaged vectors or oncolytic viruses can be obtained from the cells, for example by cell lysis and particle purification using standard procedures.

Helper viruses can be separated from packaged high-capacity vectors, for example by ultracentrifugation on cesium chloride density gradients and/or anion exchange and size exclusion chromatography.

Methods for Screening Potential New Drug Targets for Anti-Adenoviral Therapeutic Strategies The adenoviral library disclosed herein can also be used to screen for potential new drug targets for anti-adenoviral therapeutic strategies. Currently, there are no anti-adenoviral drugs available, and until now a system for drug screening against many different serotypes has not been available due to the lack of cloned adenoviral genomes. For this purpose, adenoviral genome sequences comprising reporter genes are constructed, based on the adenoviral library disclosed herein.

Therefore, the invention provides an adenoviral sequence selected from SEQ ID NOs:1-3, 5-12, 14-15 and 17-32, comprising one or more reporter genes and means for their expression, replacing part or all of the E3 region.

Suitable reporter genes include a gene encoding a fluorescent protein, for example green fluorescent protein (GFP), and/or a luciferase gene. Multiple reporter genes can be inserted so that different assays can be conducted. These reporter genes thereby allow the identification of the tropism of the adenovirus as they can be used to establish the level of infectivity of that adenovirus in cell lines derived from different tissues.

Vectors comprising such sequences are also provided. Preferably, the vector carrying the above sequence is a medium copy plasmid, for example, a p15A, pBR322, pR6K, pRK2, pBBR1 or an Inc-based plasmid. Plasmids with a p15A origin are particularly preferred.

In one embodiment, the invention provides a method of screening for potential anti-adenoviral drugs, comprising:
 a) infecting a cell with a vector comprising one or more reporter genes and means for their expression, as described above, in the presence and in the absence of a drug of interest;
 b) detecting the expression level of the reporter gene product in the presence and in the absence of the drug; and
 c) comparing the expression level of the reporter gene product in the presence and in the absence of the drug.

The relative expression levels of the reporter gene product(s) in the presence versus the absence of the drug give an indication of whether the drug reduces adenovirus infectivity (i.e. has anti-adenoviral activity). If the expression level is reduced in the presence of the drug, relative to the absence of the drug, it indicates lower infectivity in the presence of the drug, and therefore likely anti-adenoviral activity of the tested drug.

The above method can be used for high-throughput drug screening.

In some embodiments of the various aspects disclosed herein, the adenoviral sequence is not a sequence derived from at least one of (e.g. of 1, 2, 3, 4 or all 5 of) the adenoviruses selected from the group consisting of B3, B11, B35, C5 and D26. For example, in some embodiments of the various aspects disclosed herein, the adenoviral sequence is not a sequence derived from at least one of (e.g. of 1, 2 or all 3 of) the adenoviruses selected from the group consisting of B11, B35 and C5. For example, in some embodiments of the various aspects disclosed herein, the adenoviral sequence is not a sequence derived from at least one of (e.g. of 1, 2 or all 3 of) the adenoviruses selected from the group consisting of B3, B35 and C5. For example, in some embodiments of the various aspects disclosed herein, the adenoviral sequence is not a sequence derived from the C5 adenovirus. However, in some embodiments of the various aspects of the invention, the invention does extend to adenoviral sequences derived from at least one of (e.g. of 1, 2, 3, 4 or all 5 of) the adenoviruses selected from the group consisting of B3, B11, B35, C5 and D26.

b) Genome isolation of different Ad types visualized on an agarose gel.

Figure 2:
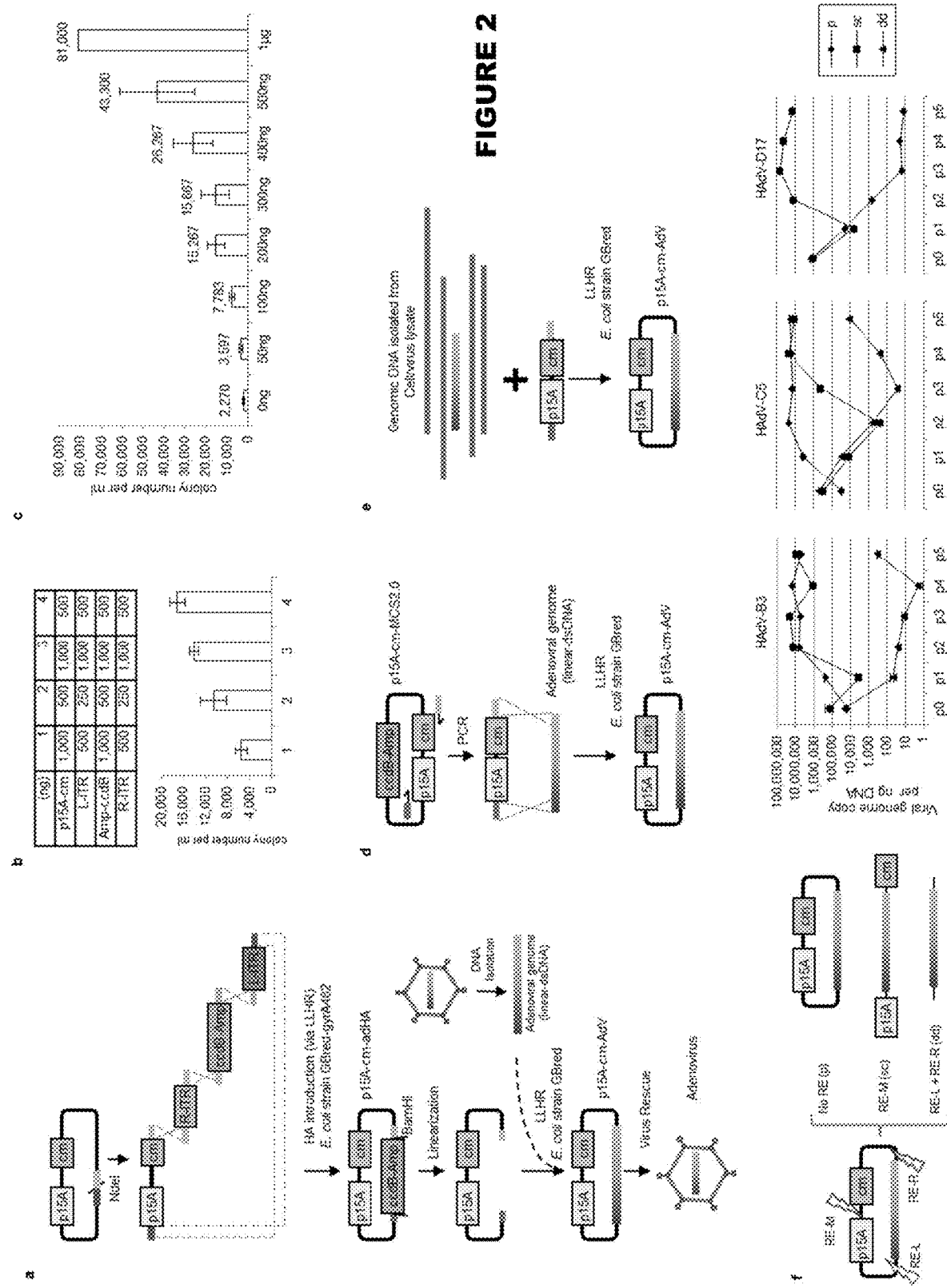

FIG. 2—Direct cloning (HTC) of Ad genomes by LLHR
a) Prototypal strategy to direct clone Ad genomes by LLHR. The shuttle vector p15A-cm-adHA was constructed by co-electroporation of four DNA fragments sharing terminal homologous arms (HAs) into the RecET expressing *E. coli* strain GBred-gyrA462, which has an R462C mutation in the GyrA subunit of DNA Gyrase that confers resistance to CcdB expression. The final vector p15A-cm-AdV was generated via a second LLHR step in RecET expressing *E. coli* strain GBred by co-electroporation of the linearised shuttle vector and the linear double-stranded adenoviral DNA (linear-dsDNA). NdeI and BamHI restriction digestion was used to linearize the circle plasmids.

b) Recombineering efficiency for shuttle vector construction using different amounts of PCR products in four experimental settings.

c) Recombineering efficiencies of viral genome cloning using various amounts of viral genomic DNA (0 to 1 µg) and 1 µg of the linearized shuttle vector. Error bars, s.d.; n=3.

d) Single-PCR based Ad genome cloning. The vector backbone p15A-cm was generated by a single PCR from a modified plasmid p15A-cm-MCs2.0. ~50 bp homology arms (HAs) were incorporated into individual Ad genomes via primer design.

e) Direct Ad genome cloning from cell/virus lysate. Instead of purified Ad genome, a DNA mixture isolated from cell/virus lysate, or a clinical sample, was co-electroporated.

f) Left panel: Strategy to rescue engineered Ads. Different molecular forms based on restriction enzyme (RE) digest for different virus rescue strategies are shown. Right panel: Influence of the genome-releasing status on virus rescue efficiency after DNA transfection into permissive cells. Y-axis indicates viral genome copy numbers isolated from cell/virus lysates collected after each passage. X-axis is the passage number after transfection. dd, completed exposed adenoviral genome released by double-digest; sc, linearized adenoviral genome released by single-cutter; p, circular plasmid. Amp, ampicillin; cm, chloramphenicol; ccdB, counter-selection marker.

Figure 3:
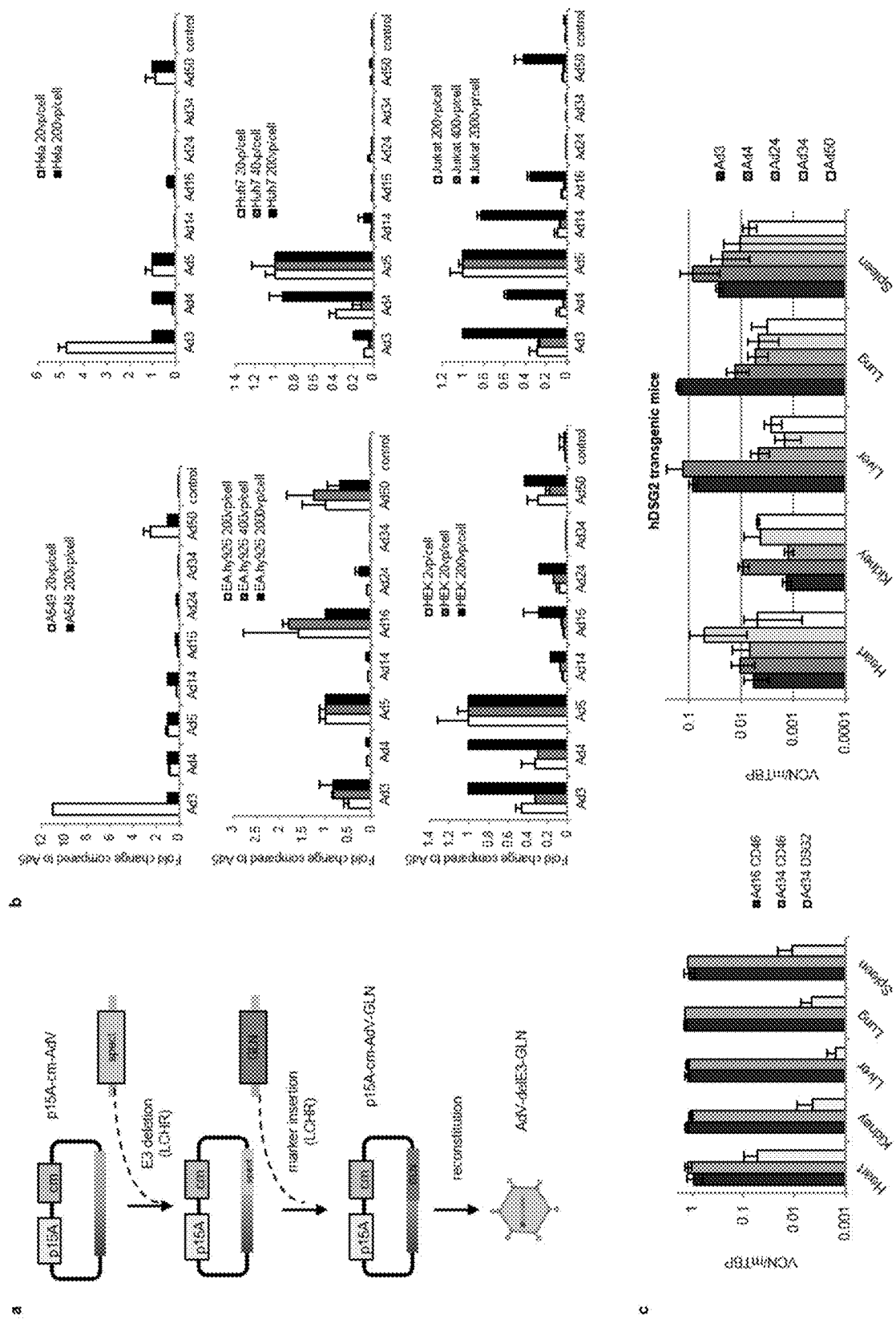

FIG. 3—Ad genome tagging and in vitro/in vivo characterisation
a) Strategy for high-throughput ad genome tagging by linear-circular homologous recombination (LCHR). The E3 region was first deleted by integration of the spect-cassette, which was then replaced by the multicistronic/triple-expression cassette (GLN).

b) In vitro characterisation of tagged Ad. Transgene expression efficiency of different Ad types was compared to the common used Ad5, and indicated as fold-change. Luciferase expression was measured by addition of furimazine substrate and indicated by luminescence units (RLU).

c) Bio-distribution study of tagged Ad in transgenic mice.

Figure 4:
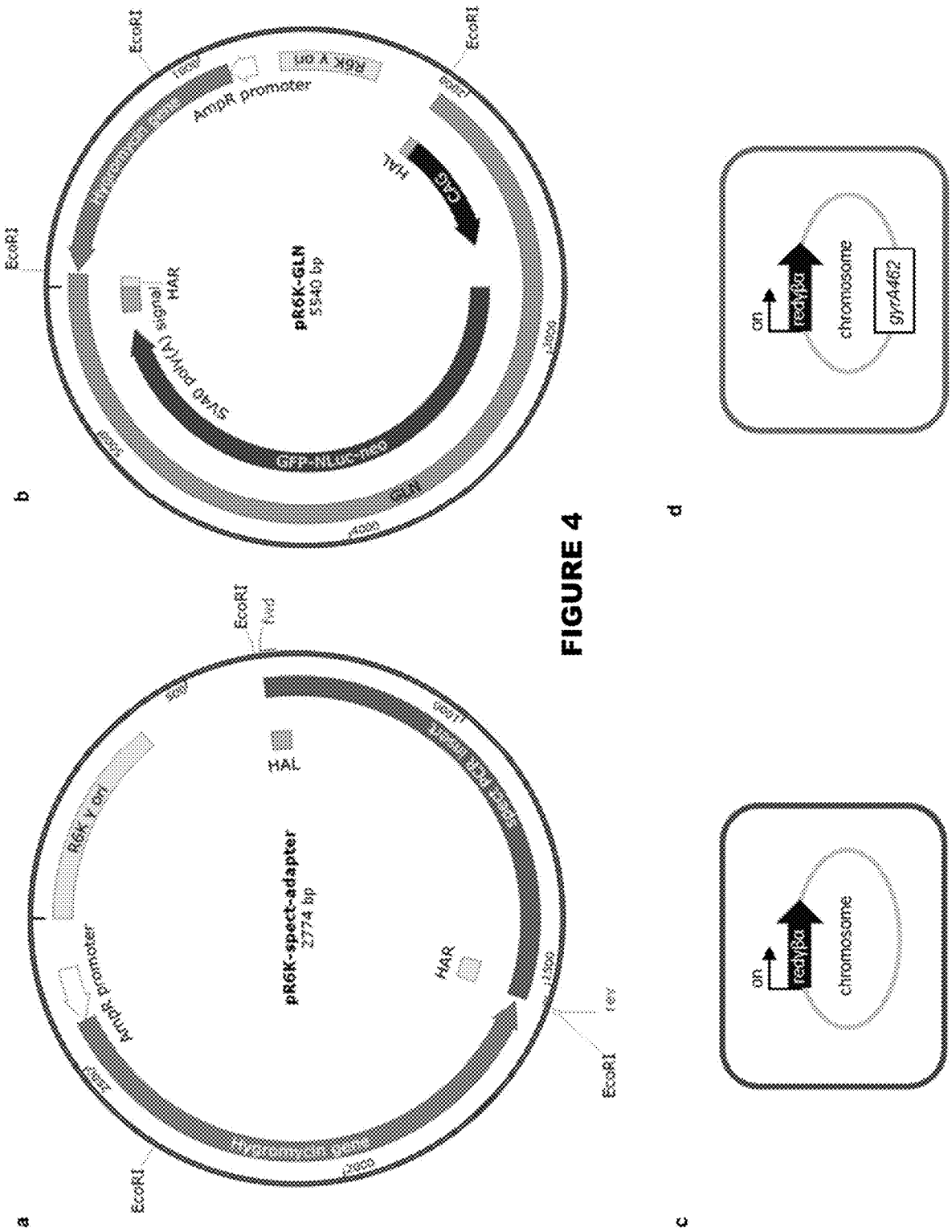

FIG. 4—Recombineering toolkit for Ad genome tagging including plasmid maps and sequences of pR6K-spect-adapter and pR6K-GLN
a) pR6K-spect-adapter serves as a PCR template to amplify selection marker spectinomycin adenyltransferase (spect), which is flanked by the same homologous arm (HAR and HAL) as the reporter cassette GLN (shown in b). EcoRI restriction enzyme digest releases the PCR template. The R6K backbone is used to avoid plasmid contamination.

b) pR6K-GLN provides the reporter gene cassette GLN which is released by EcoRI restriction enzyme digest. *E. coli* strain GB05-Red harbouring an arabinose inducible gbaA operon (redγ, redβ, redid and recA) at the ybcC locus2 mediates highly efficient LCHR. *E. coli* strain GBred-gyrA462 is generated from GB05-Red with the Arg462-coding codon CGT been changed into Cys-coding codon TGC, allowing resistance to CcdB expression[37]. All plasmid maps used in this study are created with SnapGene software.

Figure 5:
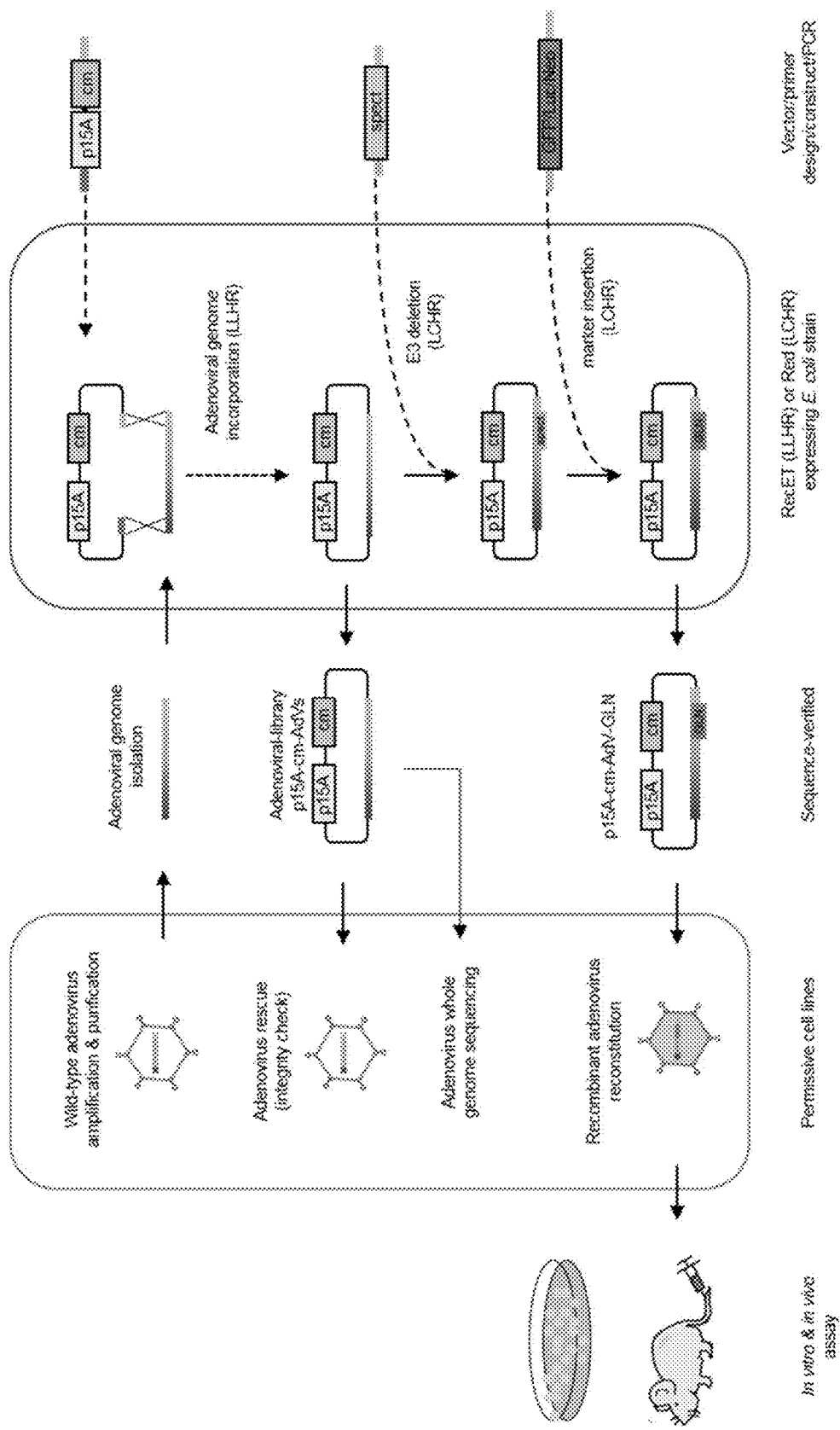

FIG. 5—Summary of the complete pipeline to study natural Ad diversity and to generate an engineered Ad library including tagging of viral genomes The process begins with wild-type adenovirus amplification in respective permissive cell lines (e.g. HeLa, HEK, A549). After virion purification the adenovirus genomic DNA is isolated and verified by sequencing and restriction enzyme digest. According to the sequence identification the shuttle vector p15A-cm-adHA is computationally designed, and constructed by co-electroporation of four DNA fragments containing homologous arms (HA) to each other into the RecET expressed *E. coli* strain, where LLHR takes place. In the next step, the adenoviral genome is incorporated into the linearised shuttle vector containing HA to each ITR end via LLHR. Sequence-verified plasmids harbouring adenoviral genomes are collected together building up an engineered adenoviral library. To prove integrity of the cloned adenovirus genomes rescue experiments were performed. Marker gene GFP/LUC tagging was mediated by linear-circular homologous recombination (LCHR). The E3 region was first deleted by integration of the ccdB-Amp cassette, which was then replaced by a P2A peptide-mediated bicistronic-expression cassette expressing a Turbo Green fluorescent protein and a NanoLuc luciferase (tGFP-Nluc) to generate p15A-cm-AdV-tGFP-Nluc. The tagged adenovirus AdV-delE3-tGFP-Nluc can be reconstituted in its permissive cell line and further evaluated in vivo.

Figure 6:
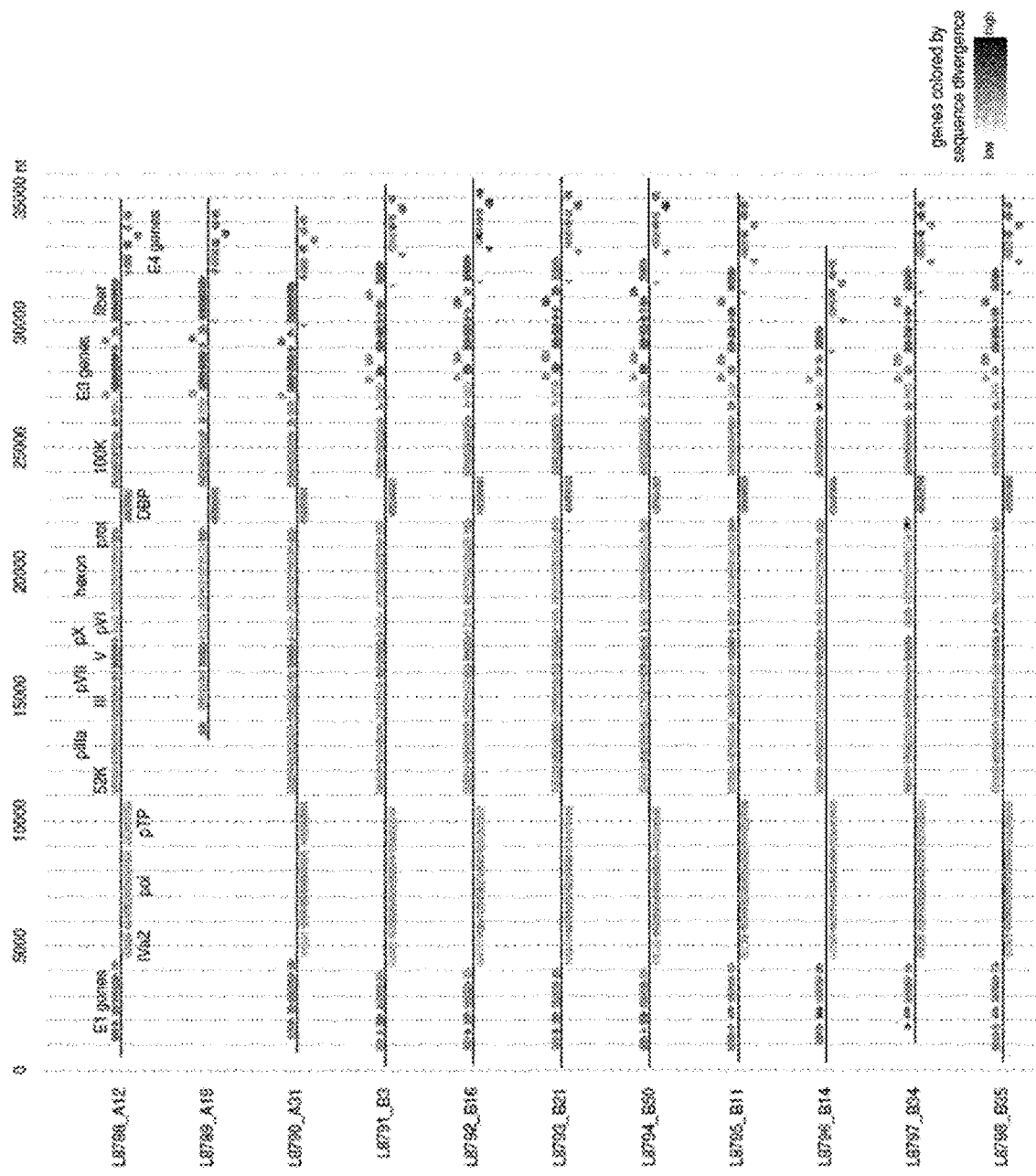
Figure 6:
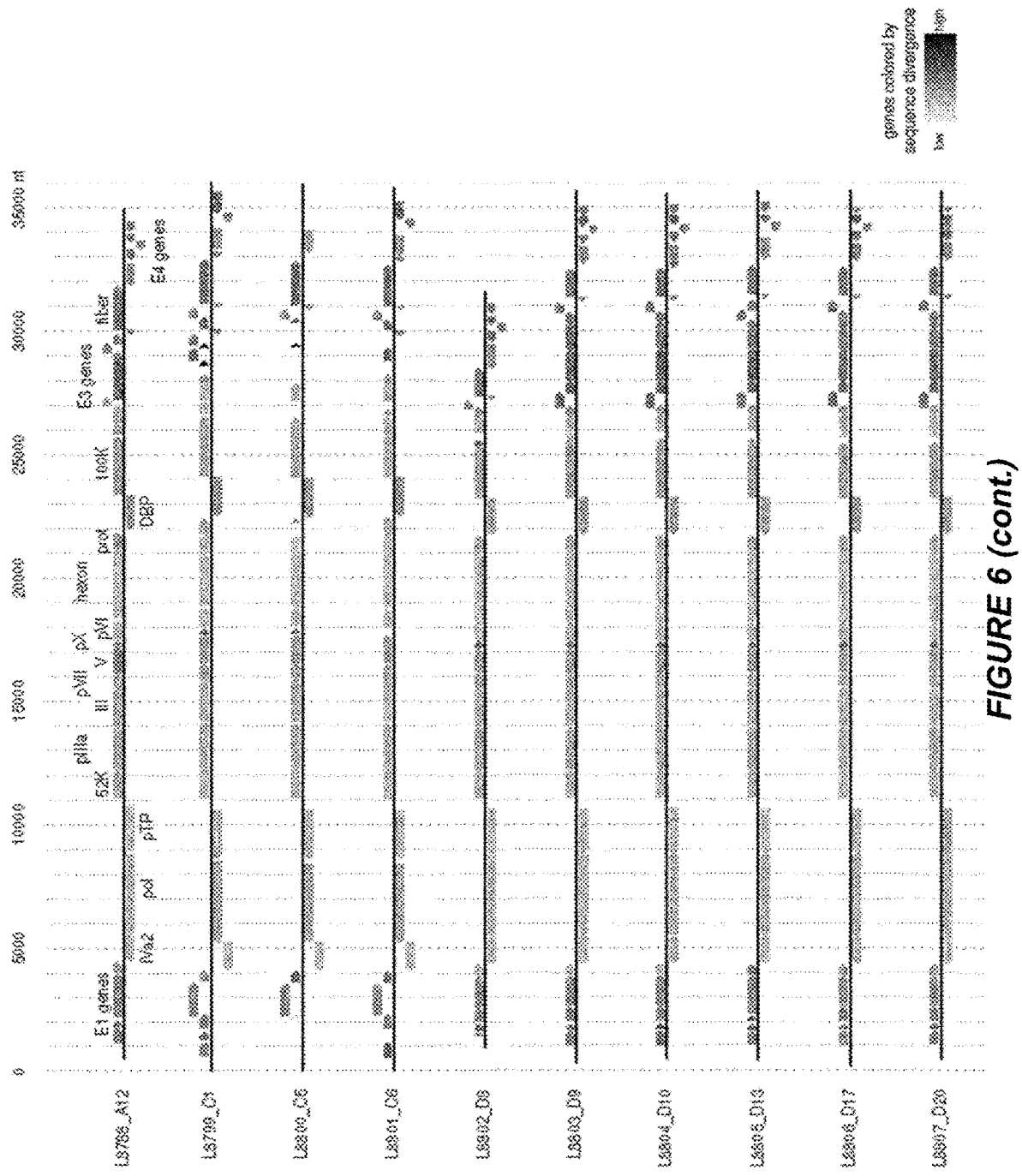
Figure 6:
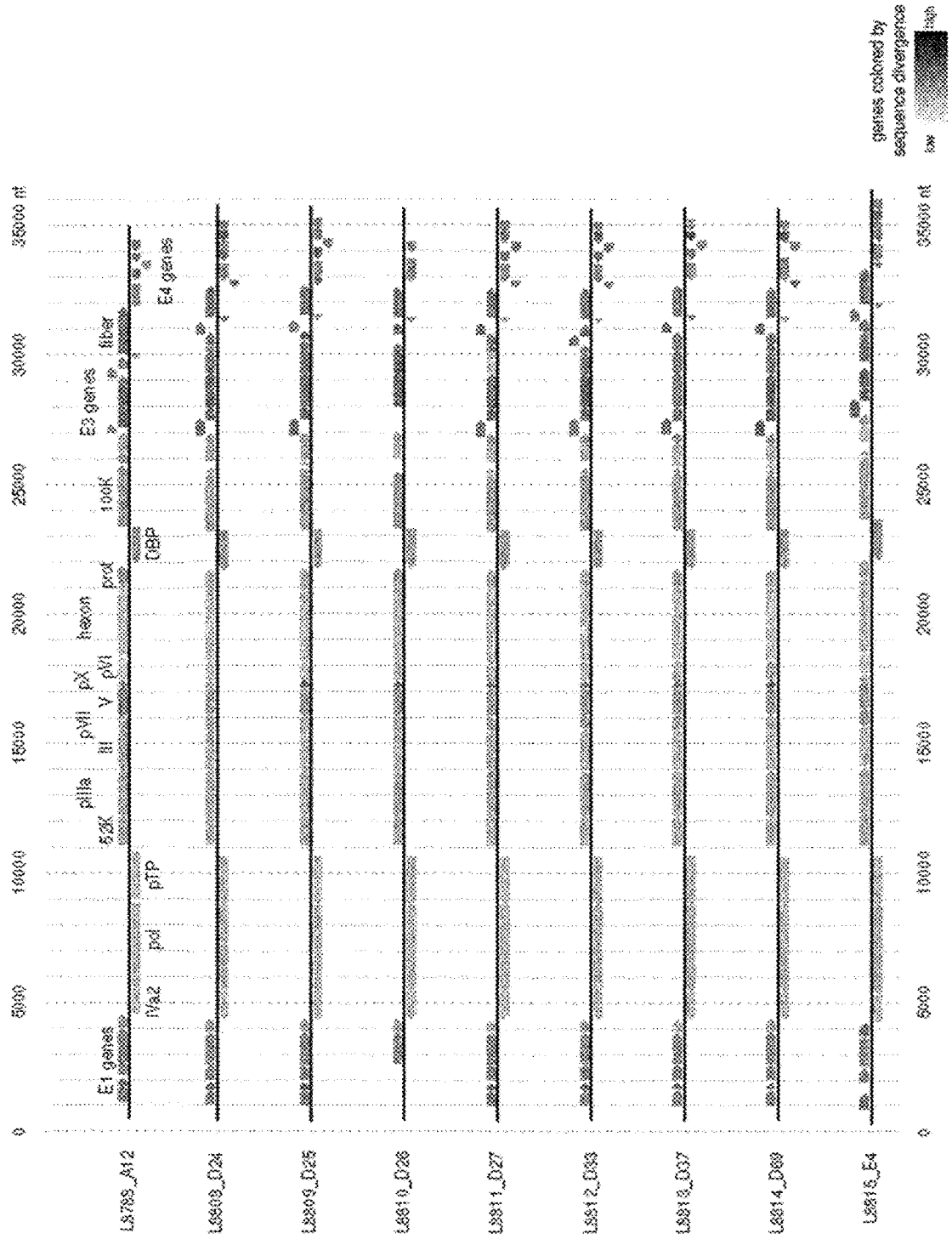

FIG. 6—Genome organisation of cloned adenoviruses

Figure 7:
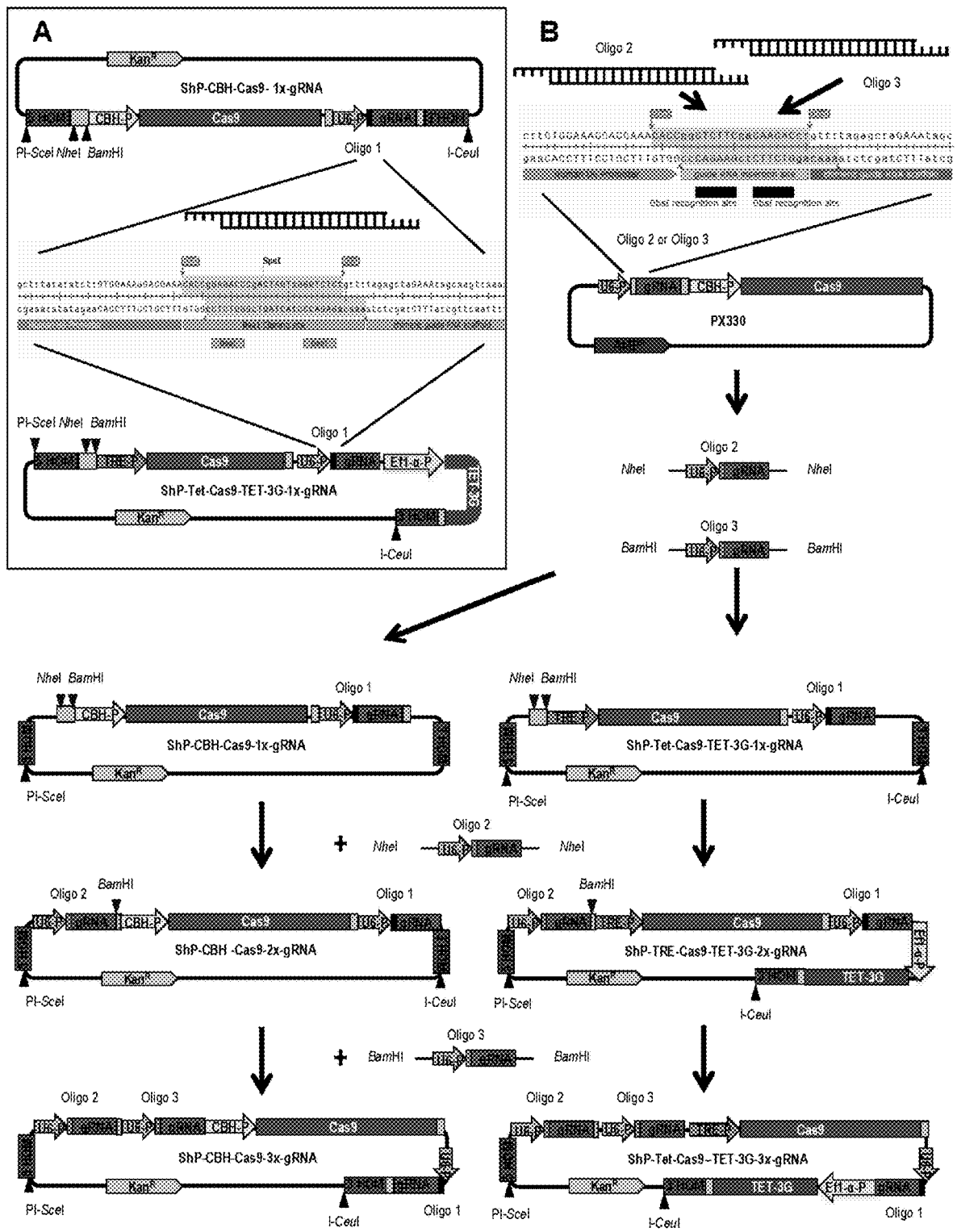

FIG. 7—HCAdV-CRISPR/Cas9 pipeline (1)

Cloning of three guide RNAs and the Cas9 coding sequence expressed under the control of a constitutive or an inducible promotor into the shuttle vector. Partial sequences used in cloning are shown in (A) (SEQ ID NOs: 1448 and 1449) and (B) (SEQ ID NOs: 1450 and 1451).

Figure 8:
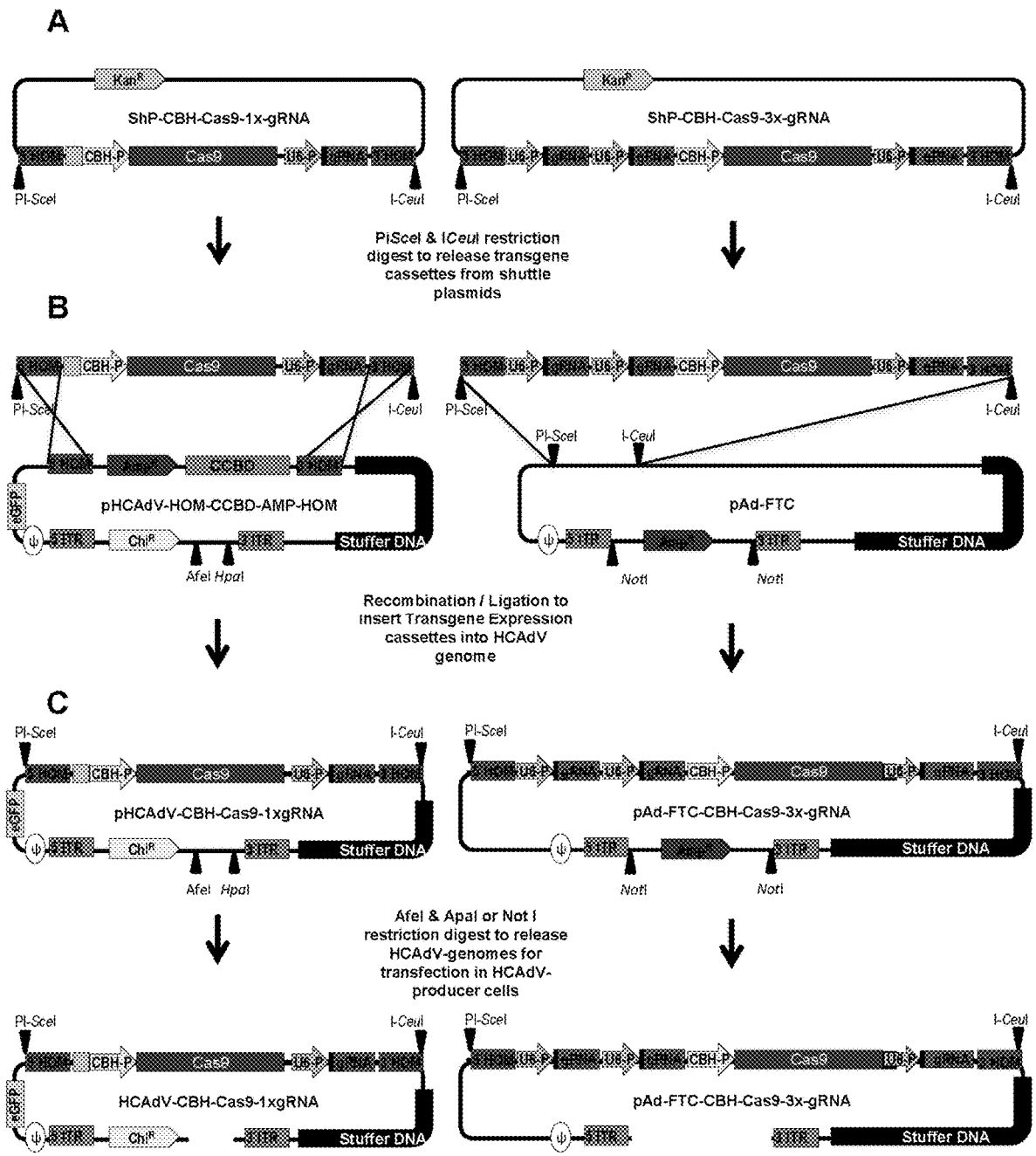

FIG. 8—HCAdV-CRISPR/Cas9 pipeline (2)

Cloning of three guide RNAs and the Cas9 coding sequence expressed under the control of a constitutive or an inducible promotor into the high-capacity adenoviral vector.

Figure 9:
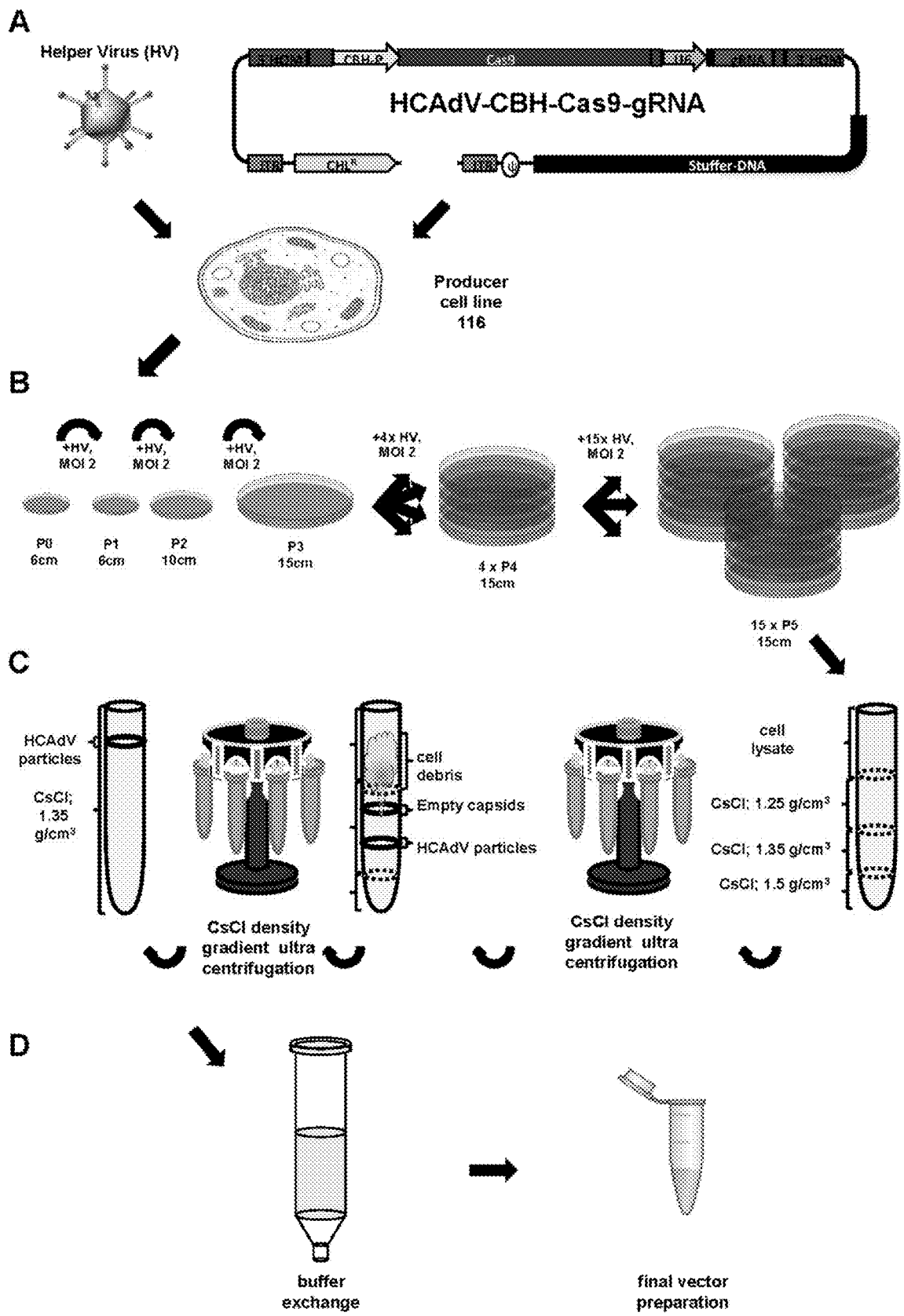

FIG. 9—HCAdV-CRISPR/Cas9 pipeline (3)

Production of high-capacity adenoviral vectors containing the CRISPR/Cas9 machinery.

Figure 10:
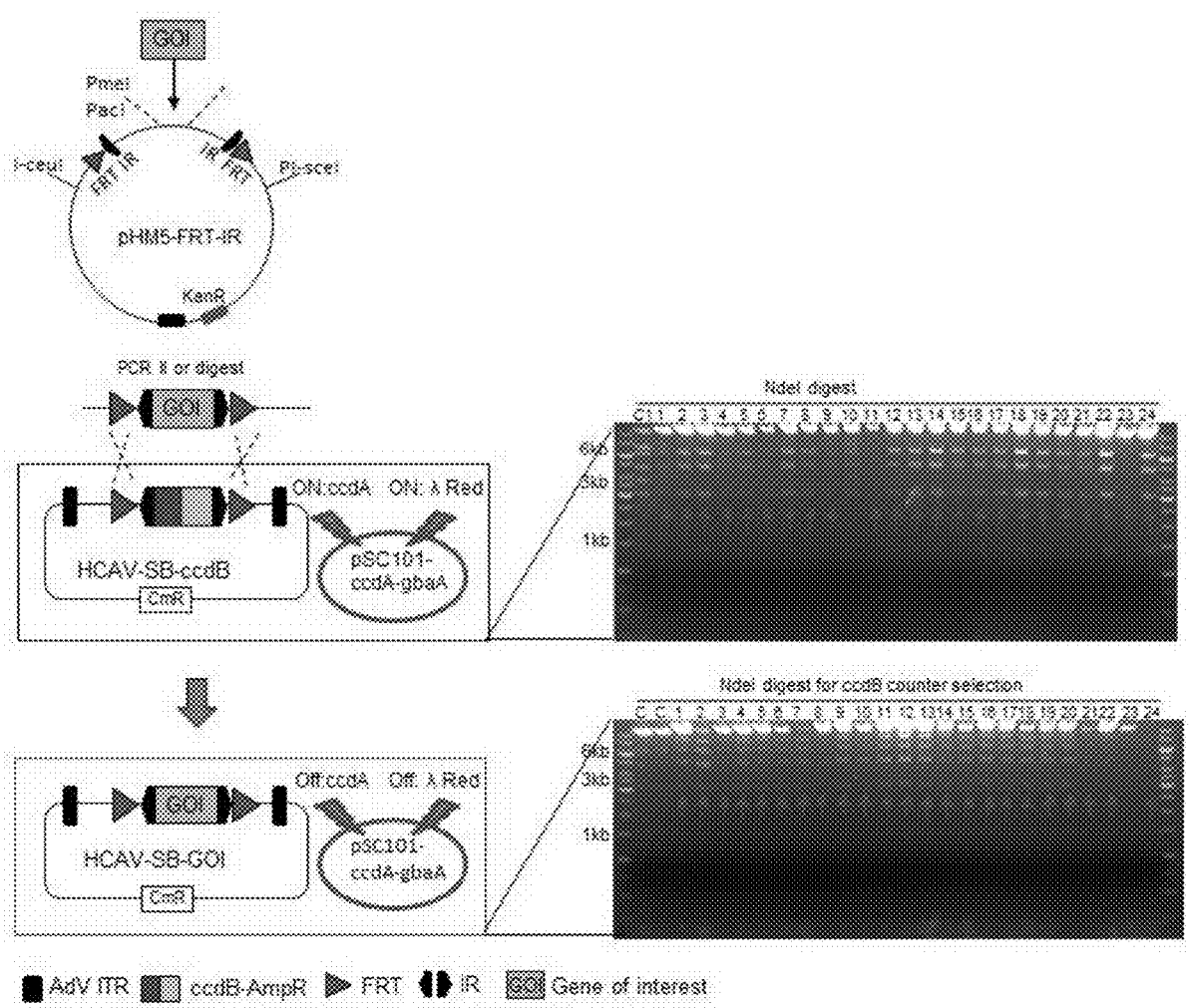

FIG. 10—Recombineering pipeline for construction of adenovirus-Sleeping Beauty transposon hybrid vectors After cloning the gene of interest into the shuttle vector pHM5-FRT-IR it can be transferred to the high-capacity adenoviral vector by recombineering.

Figure 11:
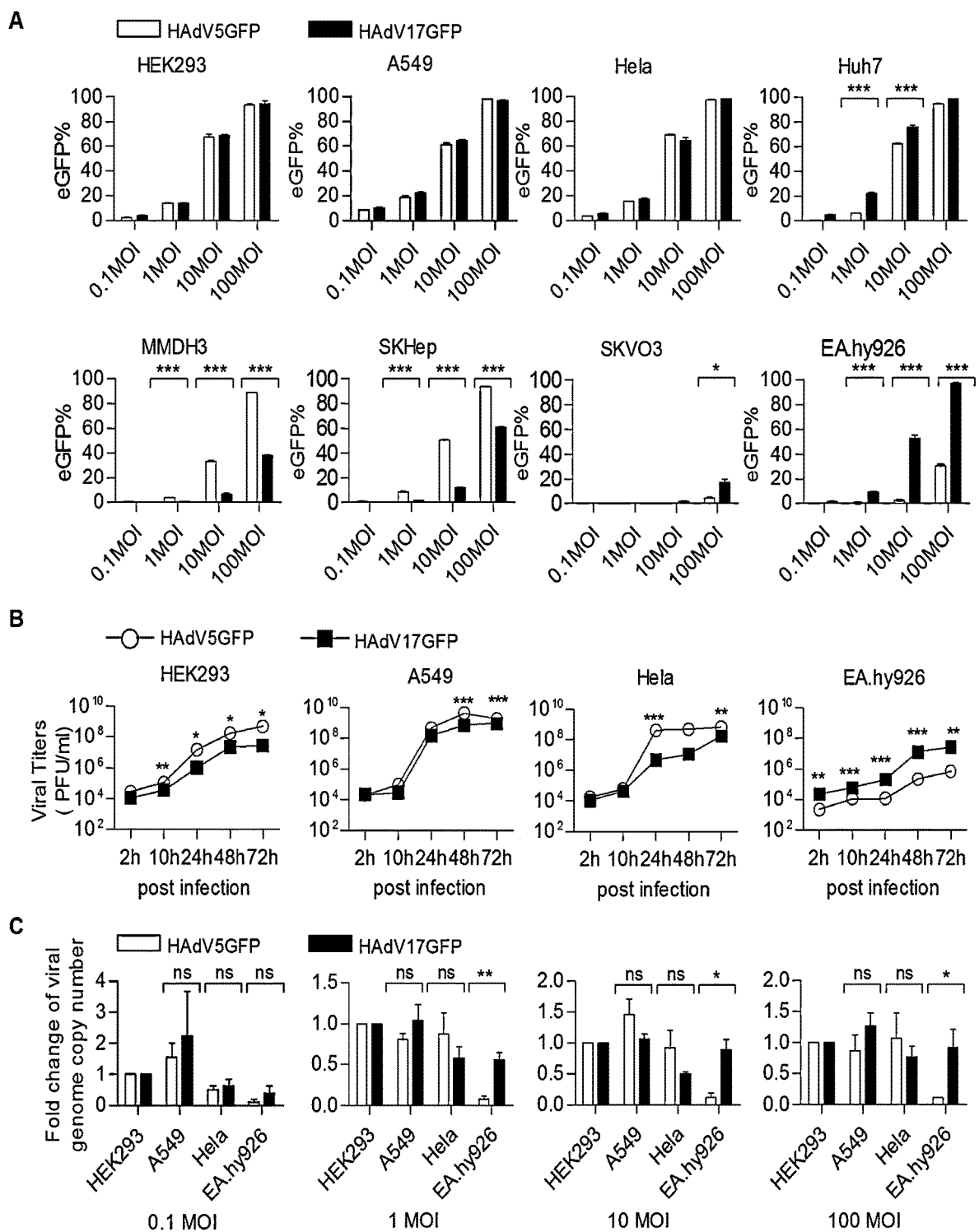

FIG. 11—HAdV17 has tropism for endothelial cells in vitro

A. Cell line screening in vitro. HEK293, A549, Hela, Huh7, Jurkat, MMDH3, SKHep, SKOV3 and EA.hy926 cells were seeded in 24 well plates the day before infection. When 90% confluent, cells were transduced with HAdV5GFP and HAdV17GFP at various multiplicities of infection (0.1, 1, 10 or 100 per cell) for 2 h. GFP expression was analysed 24 h post-infection by FACS. Uninfected cells (negative controls) were used to set the background gate at approximately 1%. Percentages of GFP-positive cells are given.

B. Growth curve comparison between wild type HAdV17 and HAdV5. HEK293, A549, Hela and EA.hy926 were seeded in 24 well plates the day before infection. When 80% confluent, cells were transduced with wild type HAdV5 and HAdV17 at a multiplicity of infection (MOI) of 10. Cells were harvested at various time points (2, 10, 24, 48, 72 hours), and quantitative PCR was performed after cellular DNA isolation to detect assay for virus replication.

C. Virus internalization analysis by quantitative PCR. HEK293, A549, Hela and EA.hy926 were infected at MOIs of 0.1, 1, 10, 100 of HAdV5GFP and HAdV17GFP in 24 well plates for 2 h. Afterwards cells were treated with 5% trypsin for 3 min, centrifuged at 500 g for 3 min and washed twice with DPBS to ensure that only internalised viral particles were analysed. Total cellular DNA (including the adenoviral DNA) was extracted, and quantitative real-time PCR was performed to detect viral genome. Data points represent mean standard error based on three independent experiments (n=3).

FIG. 12—Transduction of primary human umbilical vein cells (HUVEC)

Transduction of primary human umbilical vein cells (HUVEC). Primary HUVECs were transduced with HAdV5GFP and HAdV17GFP at various multiplicities of infection (0.1, 1, 10 or 100 per cell) for 2 hours. (A) GFP-positive cell numbers and (B) mean fluorescent intensity were analysed 24 h post-infection by FACS. Uninfected cells (negative controls) were used to set the background gate at approximately 1%. (C) Histograms show the surface markers hCAR on HEK293, HeLa, EA.hy926 and HUVEC by flow cytometry. (D) Quantitation of mean fluorescent intensity of CAR expression on cell surfaces. HeLa, EA.hy926 and HUVEC cells were stained with an anti-CAR antibody labelled with FITC and measured by flow cytometry. As negative controls each cell line was also incubated without supplementation of the primary antibody. Data points represent mean standard error (n=3).

Figure 13:
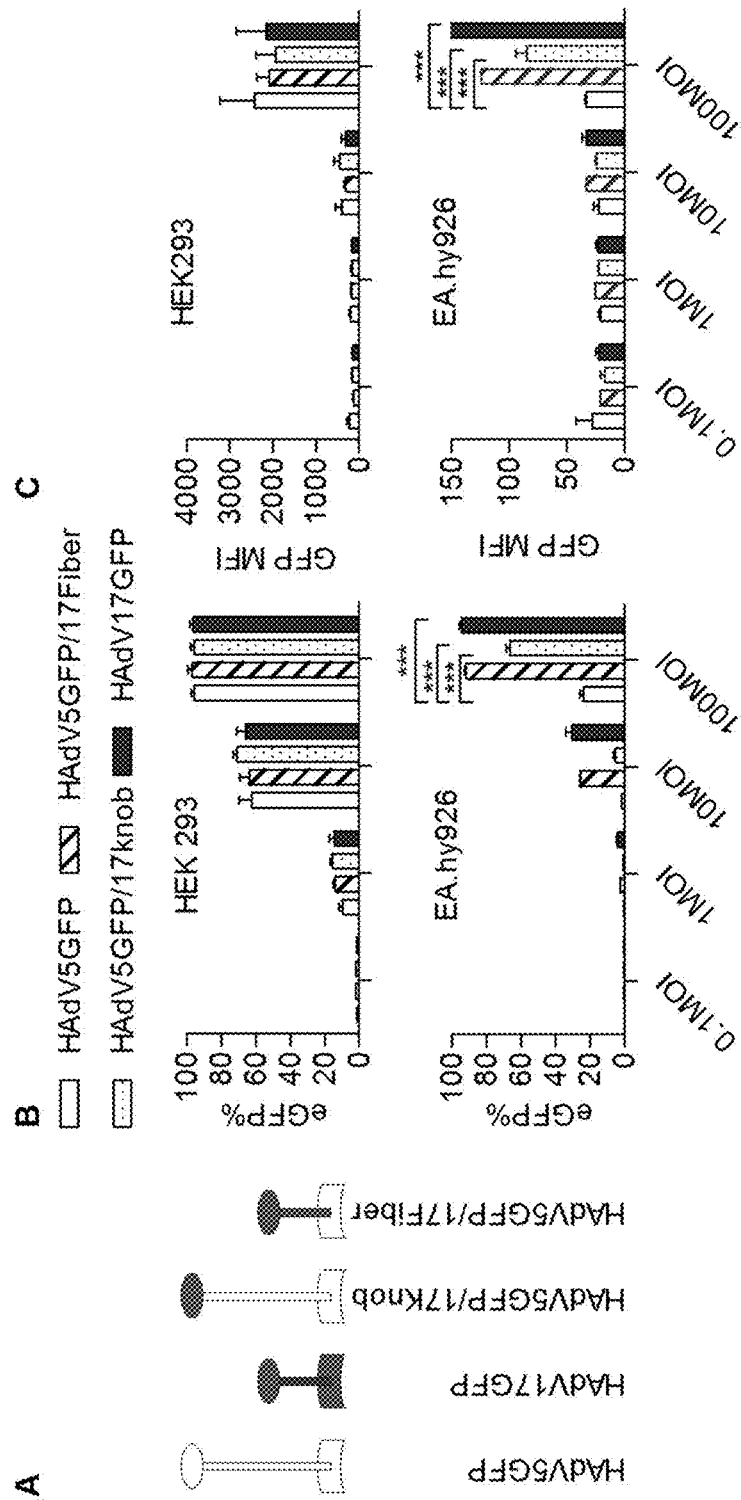

FIG. 13—Validation of endothelium tropism that is dependent on interaction between CD46 and HAdV17 fiber by gain of function study (A) Schematic representation of chimeric fiber proteins incorporated into HAdV5 capsid and structure of chimeric fiber genes (knob, shaft and tail). White depicts the fiber derived from HAdV5GFP and black depicts the fiber derived from HAdV17GFP. HAdV5GFP/17knob contained the shaft and tail from HAdV5 and knob from HAdV17. HAdV5GFP/17 fiber contained the tail from HAdV5 and both shaft and knob from HAdV17. (B) HEK293 and EA.hy926 cells were seeded in 24 well plates the day before infection. When 90% confluent, cells were transduced with HAdV5GFP, HAdV5GFP/17fiber, HAdV5GFP/17Knob and HAdV17GFP at various multiplicities of infection of (0.1, 1, 10 or 100 per cell) for 2 h. GFP expression was analysed 24 h post-infection by FACS. Uninfected cells (negative controls) were used to set the background gate at approximately 1%. Percentages indicate percentage of GFP-positive cells. MFI=mean fluorescent intensity. Data points represent mean standard error (n=3).

Figure 14:
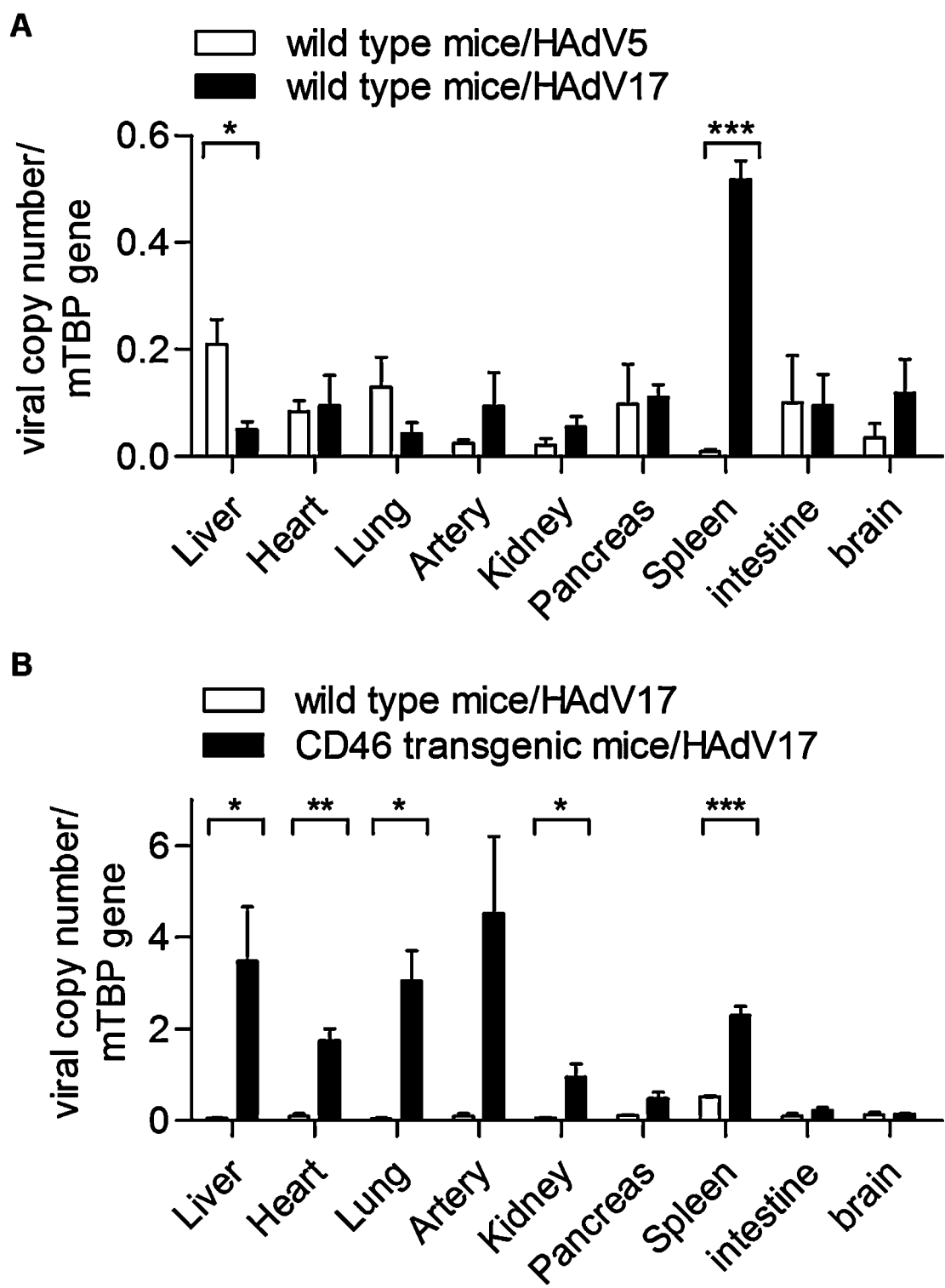

FIG. 14—in vivo biodistribution of HAdV17GFP vectors

Viral genomes were detected by real-time quantitative PCR in various organs (liver, heart, lung, artery, kidney, pancreas, spleen, intestine and brain) harvested 72 hrs after systemic administration of $2\times10^9$ transducing units per mouse of HAdV17GFP into both CD46 transgenic mice and wild-type mice. HAdV5GFP was administered to wild-type mice as a control (n=3 mice per group).

Figure 15:
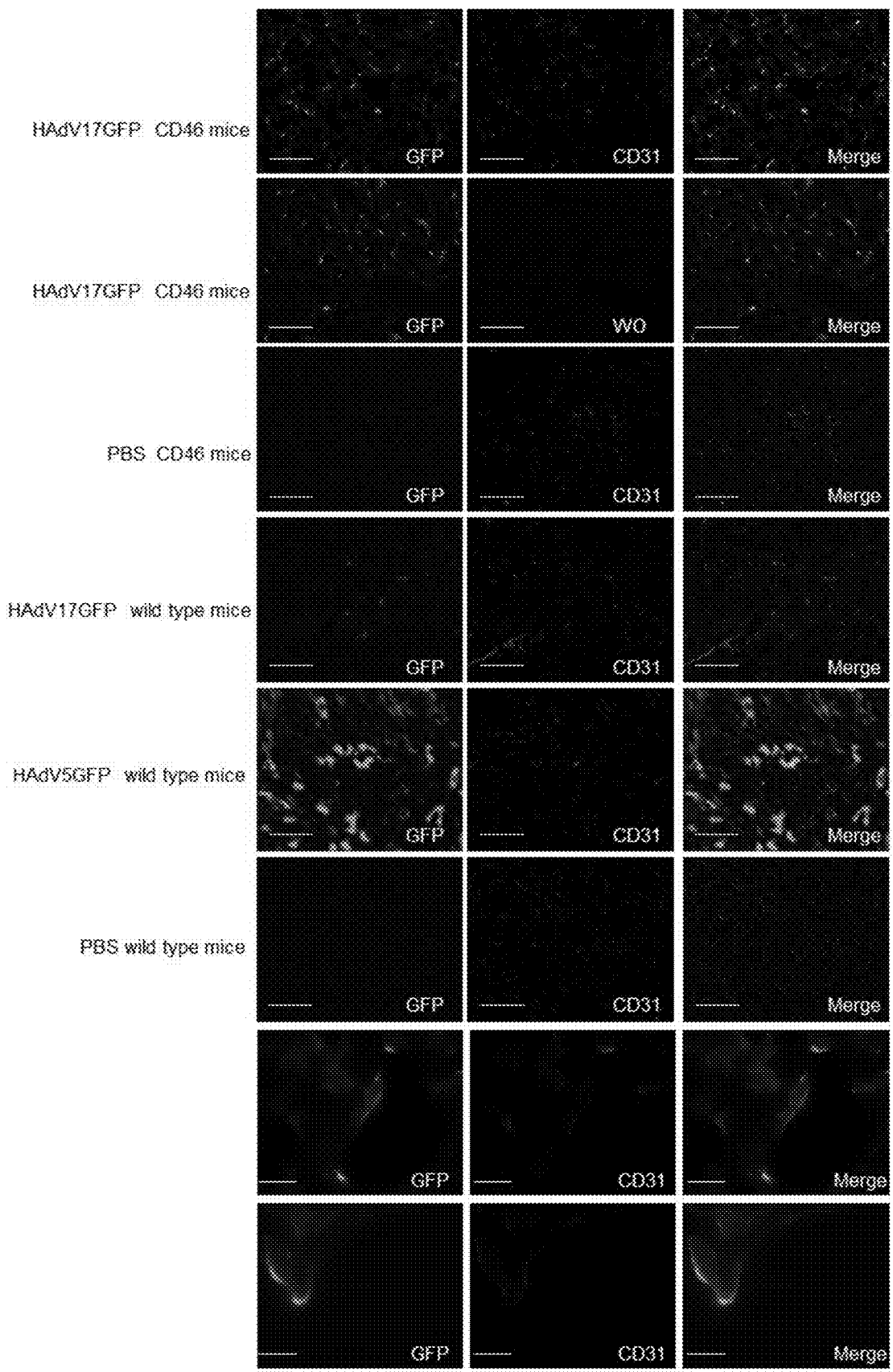

FIG. 15—Immunofluorescence analysis of liver sections

Mice were sacrificed at 3 days after vector injection, and livers were excised for histology. (A) The top panel shows colocalisation of viral transgene (GFP) expression (green) with endothelial markers (CD31, red) from CD46 transgenic mice injected with HAdV17GFP. Single stained and merged images at 20× magnification are presented. The scale bar of images is 100 μm.

The $4^{th}$ panel from the top is from wild type mice injected with HAdV17GFP. The $5^{th}$ panel from the top is from wild type mice injected with HAdV5GFP. PBS treated transgenic mice ($3^{rd}$ panel from the top) and PBS treated wild type mice ($6^{th}$ panel from the top) are controls. The $2^{nd}$ panel from the top is from CD46 transgenic mice injected with HAdV17GFP without CD31 primary antibody treatment. (B) The $7^{th}$ and $8^{1h}$ panels from the top are views at a higher magnification (60×) of the first panel. Images are representative of multiple fields of view. The scale bar of images is 25 μm.

Figure 16:
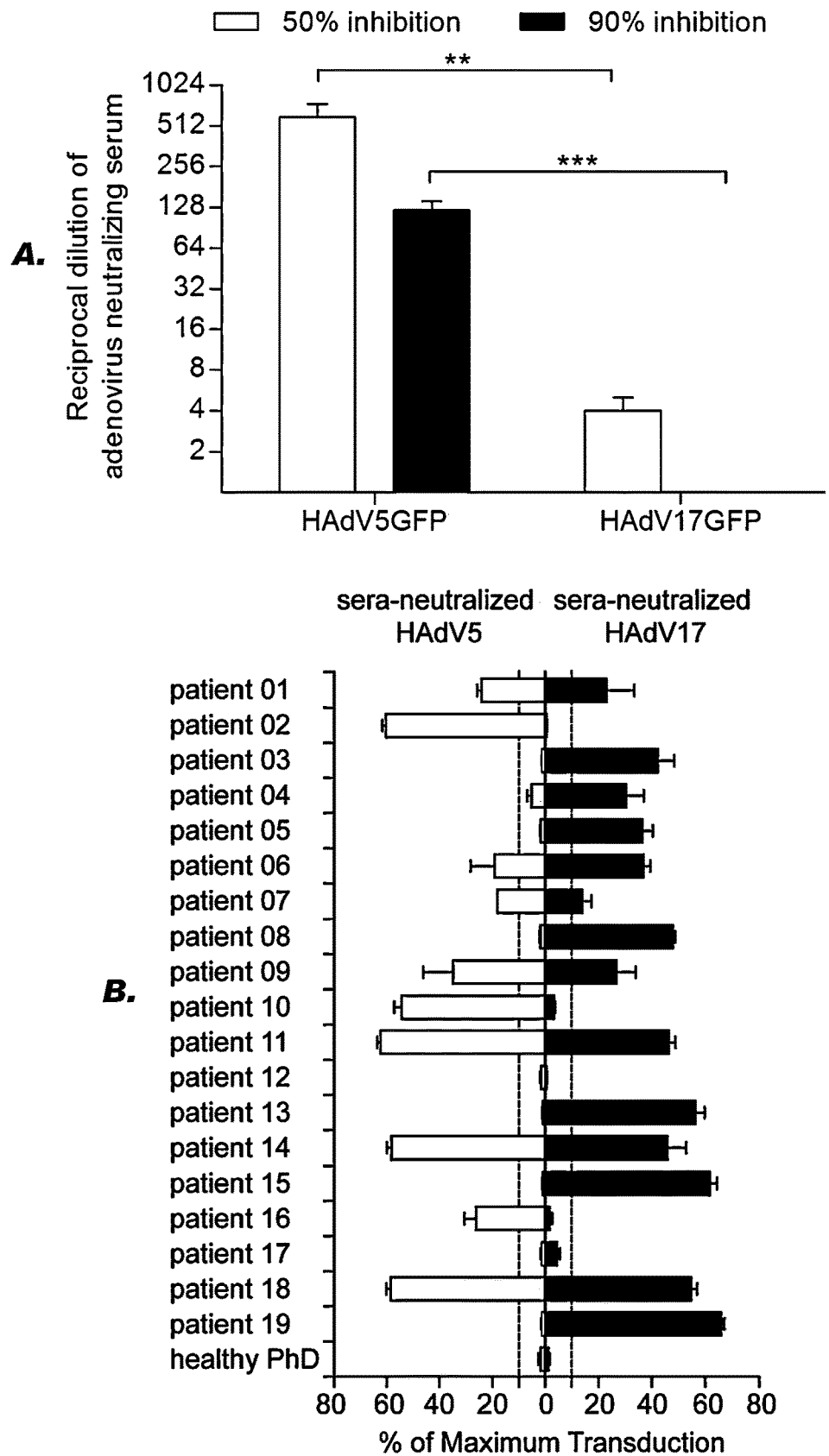

FIG. 16—Neutralising antibody assay for HadV17

(A) Reciprocal dilution of dog serum, immunised with HAdV-5, was incubated with HAdV17GFP and HAdV5GFP. The serum-virus mixture was used to infect HEK293 cells and 24 hours post-infection, GFP expression levels were determined. (B) Preexisting immunity to HAdV17 in patients. Transduction assays were carried out in the presence of serum samples from 19 patients. Samples were considered neutralising if greater than 90% reduction in transduction (below 10% residual transduction) was seen in comparison to a no-serum control.

Figure 17:
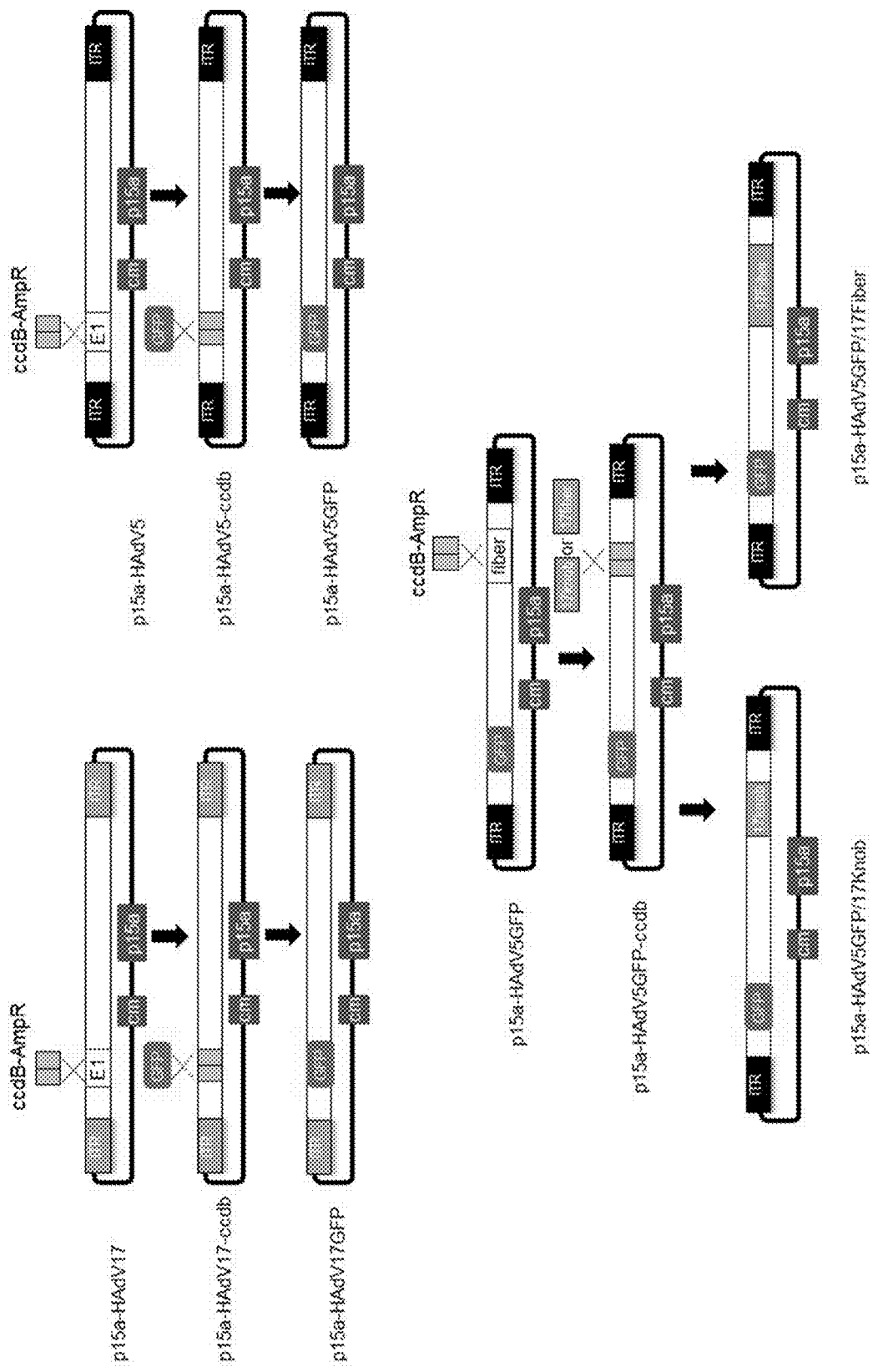

FIG. 17—Schematic structure of different virus vectors used in Example 3

(A) Diagram of ccdB recombineering to construct first generation p15a-HAdV17GFP. (B) Schematic structure of pseudotyping HAdV5GFP with knob or fiber from HAdV17.

Figure 18A:
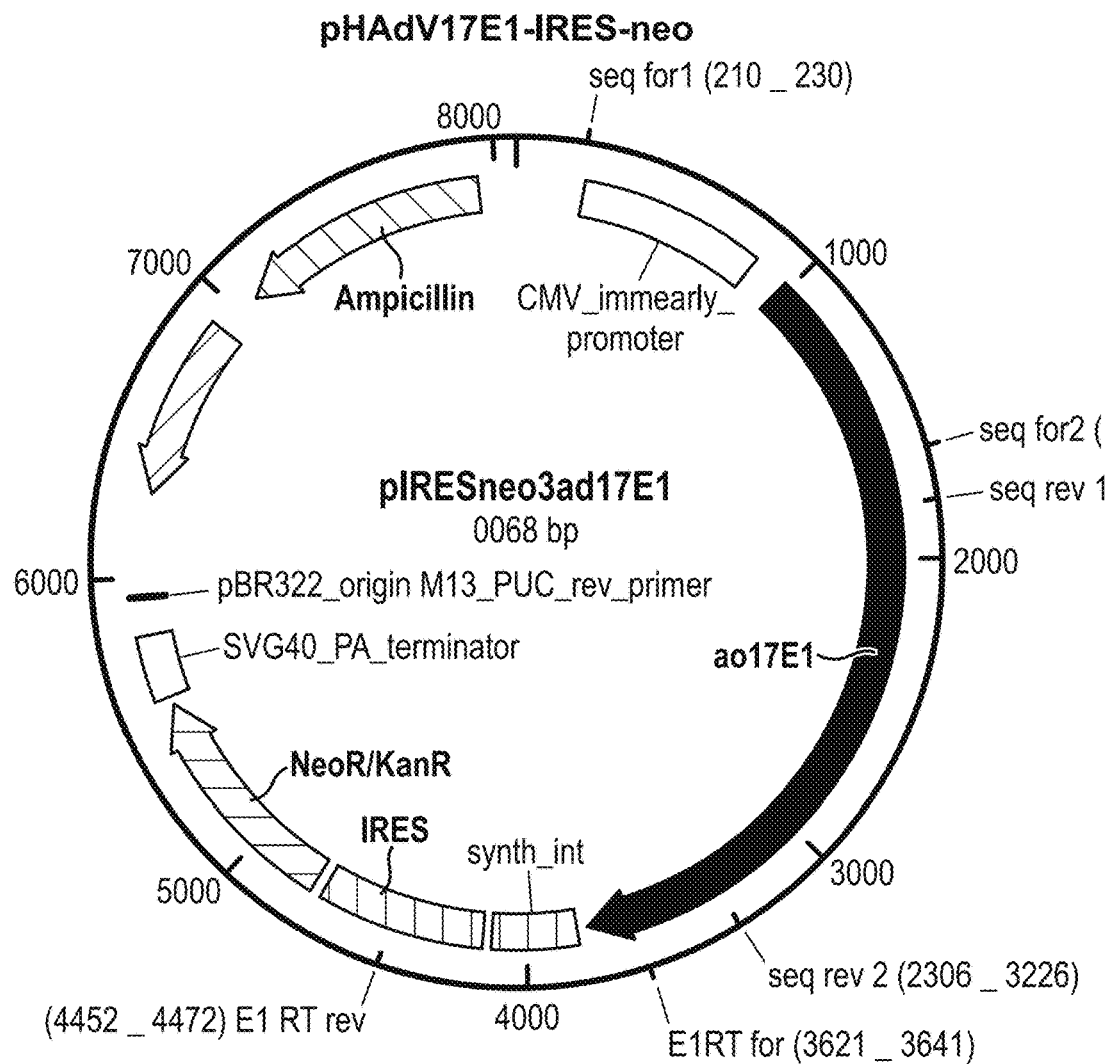
Figure 18B:
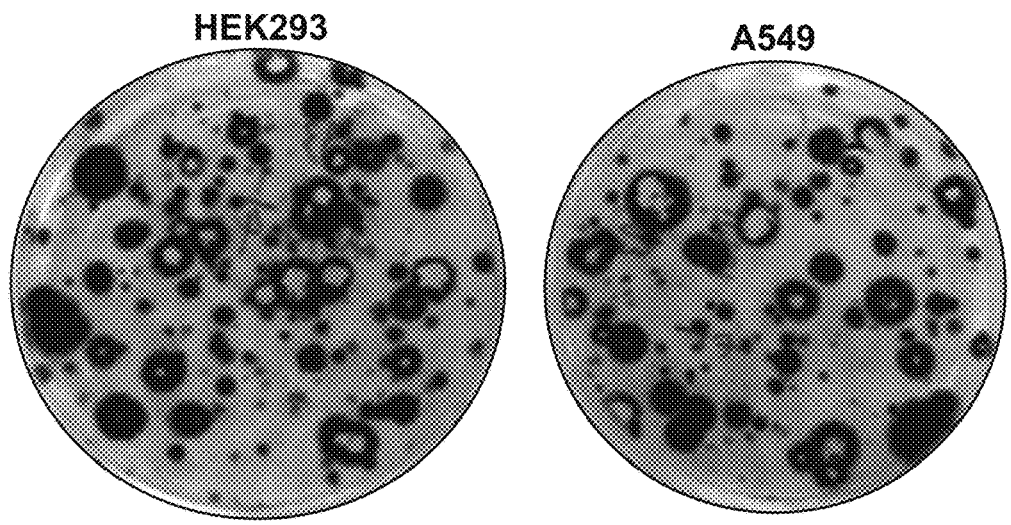

FIG. 18—Generating stable complementing cell lines based on HEK293 and A549 cells using the plasmid pIRES-neo (A) E1 cassette from HAdV17 (2808 bp) was amplified by PCR and ligated into multi cloning site of pIRESneo3 (clontech) to construct the vector pCMV-HAdV17E1-IRES-neo. (B) Methylene blue staining was performed to mark the positive cell clones. (C) PCR and RT-PCR were performed to analyse each cell clone. Genomic DNA was isolated from each cell clone and eluted in $dH_2O$. Total RNA was isolated and resuspended in RNase-free H2O. Reverse transcription was performed, and 5 μl of the cDNA was used for PCR. A negative control without reverse transcriptase was performed.

FIG. 19—Histograms show the surface markers of hCAR and CD46 expression level in various cell lines by flow cytometry $0.5\times10^6$ cells (HEK293, A549, HeLa, EA.hy926, MMDH3 and HCT116) were counted and washed with PBS supplemented with 1% BSA, centrifuged (1500 g, 3 min), and resuspended in 100 μl PBS/BSA and 2.5 μl anti-hCAR antibody (Santa Cruz, sc-56892) following an incubation step at 4° C. for 1 hour. Afterwards the cells were washed again with PBS/BSA to remove unbound antibody, resuspended in 100 μl PBS/BSA and 0.5 μl of an APC labeled goat anti-mouse secondary antibody (Santa Cruz, sc-3818), and incubated for 1.5 hours at 4° C. with continuous shaking. Afterwards cells were again washed with PBS/BSA and finally resuspended in 400 μl PBS for flow cytometry using FACS (BD). As negative controls each cell line was also incubated without supplementation of the primary antibody. Data points represent mean standard error (n=3).

Figure 20:
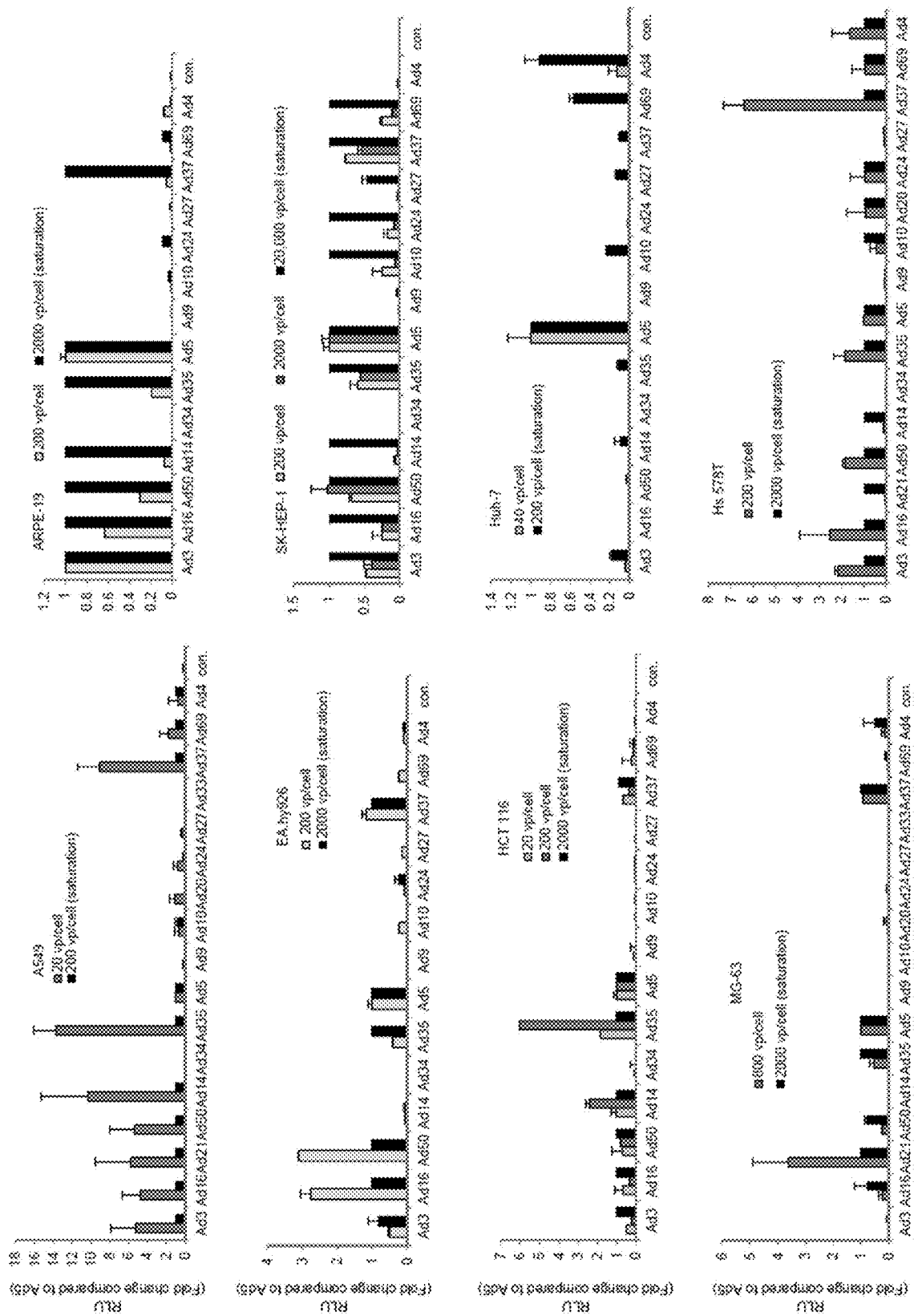

FIG. 20—High-throughput screening (HTS) of the reporter-tagged human adenovirus library in a panel of human tumour cells Transgene expression efficiency of different adenovirus types (Ad type number) was tested in a panel of disease-specific cell lines. Levels were compared to the commonly used adenovirus type 5 (Ad5) and indicated as fold change. Luciferase expression was measured by addition of Furimazine substrate and expressed as relative light units (RLU). In all cell lines error bars represent mean±SD with the exception that in A549 and MG-63 is mean±SEM.

Figure 21:
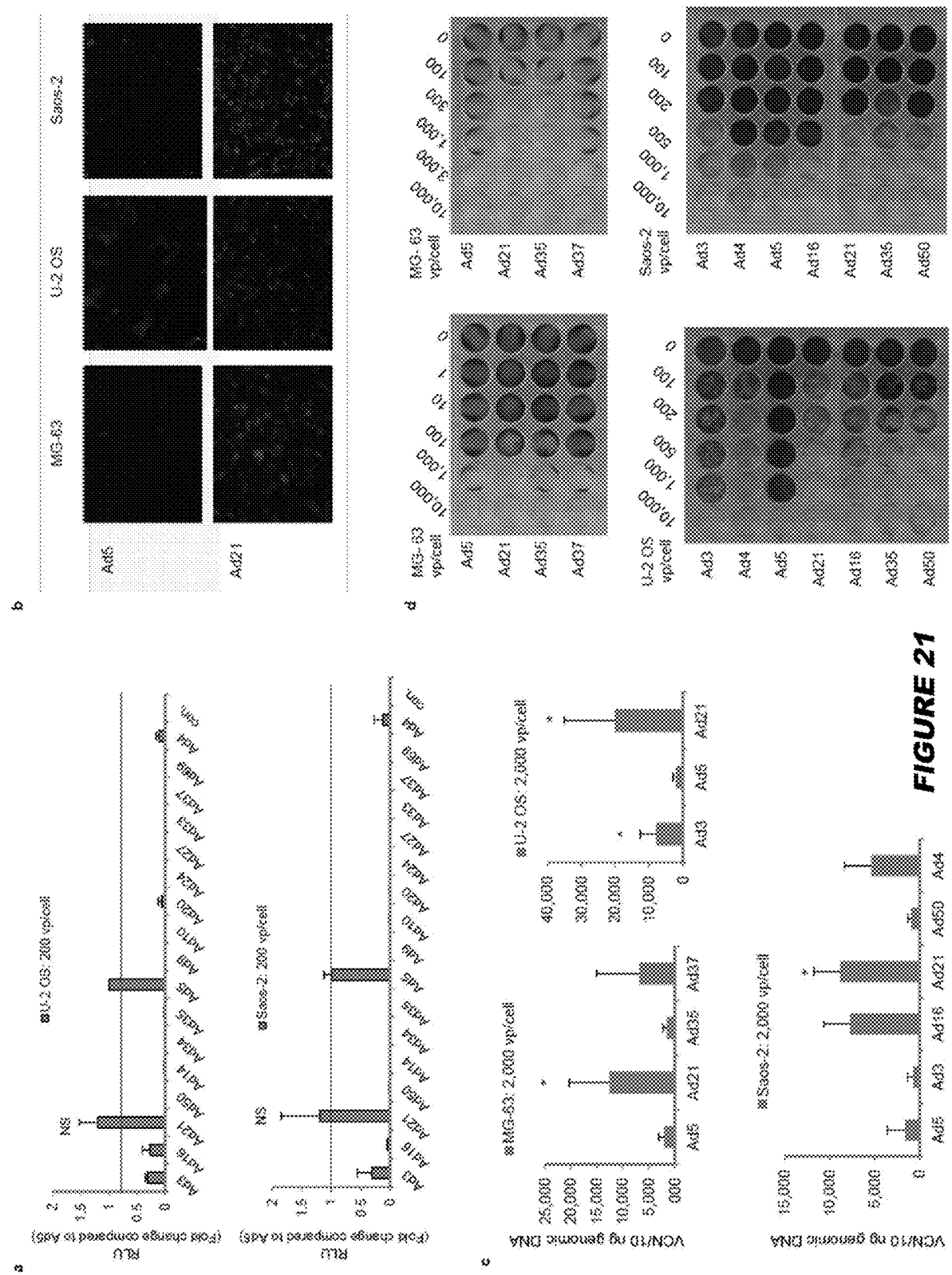

FIG. 21—High-throughput screening (HTS) to identify virus candidates with high oncolytic potency in osteosarcoma cells (A) Transduction of two osteosarcoma cell lines. 200 vp/cell were applied with three independent experiments performed. Error bars denote s.e.m. Data were analysed by two-tailed unpaired t-test. P-values for analysed virus types compared to Ad5 were <0.05 if not otherwise stated. NS, not significant; vp, viral particles.
(B) Virus internalization efficiency in three osteosarcoma cell lines. Cells were infected with individual viruses at 2,000 vp/cell for three hours to determine viral genome copy numbers (VCN), which were quantified by qPCR and expressed as VCN per 10 ng total DNA. Error bars represent mean±SD. n=3 per group. Data were analysed by two-tailed unpaired t-test. P-values for analysed virus types compared to Ad5 were >0.05 if not otherwise stated. *, significant (p<0.05).
(C) Visualization of GFP-expression 2 days post infection. Cells were infected at 1,000 viral particle (vp) per cell.
(D) Crystal violet staining of viable cells was used to evaluate oncolytic activity 7 days after infection.

Figure 22:
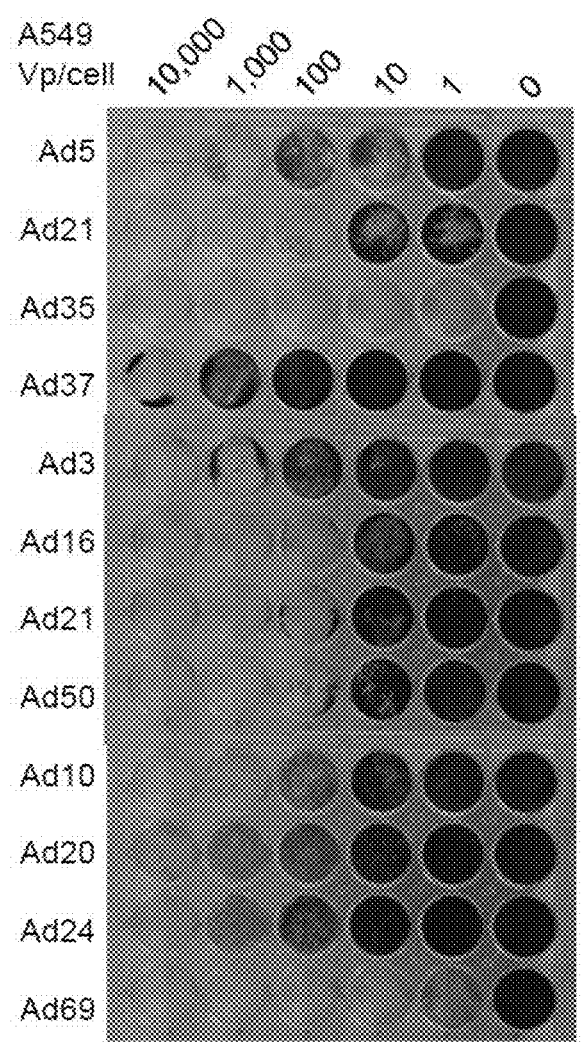

FIG. 22—High-throughput screening (HTS) to identify virus candidates with high oncolytic potency Oncolysis assay performed in A549 cells as oncolytic assay control. Crystal violet staining of viable cells was used to evaluate oncolytic activity 7 days after infection.

FIG. 23—Transgene expression efficiency of different adenovirus types (Ad type number) in the cell line RG2 [D74] at 2000 virus particle per cell (vp/c)

Ad5, Ad21 and Ad37 showed high luciferase (26 hs p.i.) and GFP expression (2 ds p.i.), albeit without being significant. All three viruses reached about the same dimension of efficiency. Furthermore Ad20 reached more than 20% of the efficiency of Ad5. Luciferase expression was measured by addition of Furimazine subtract and expressed as relative light units (RLU). Transgene expression levels were compared to the commonly used adenovirus type 5 (Ad5) and indicated as fold change. Error bars represent standard error of the mean (SEM). Data were analysed by two-tailed unpaired t-test. P-values for analyzed virus types compared to Ad5 were <0.05 if not otherwise stated. "NS" means "not significant (p>=0.05)".

The invention is further described with reference to the following non-limiting examples:

EXAMPLES

Example 1—Cloning Adenoviral Genomes

Figure 1:
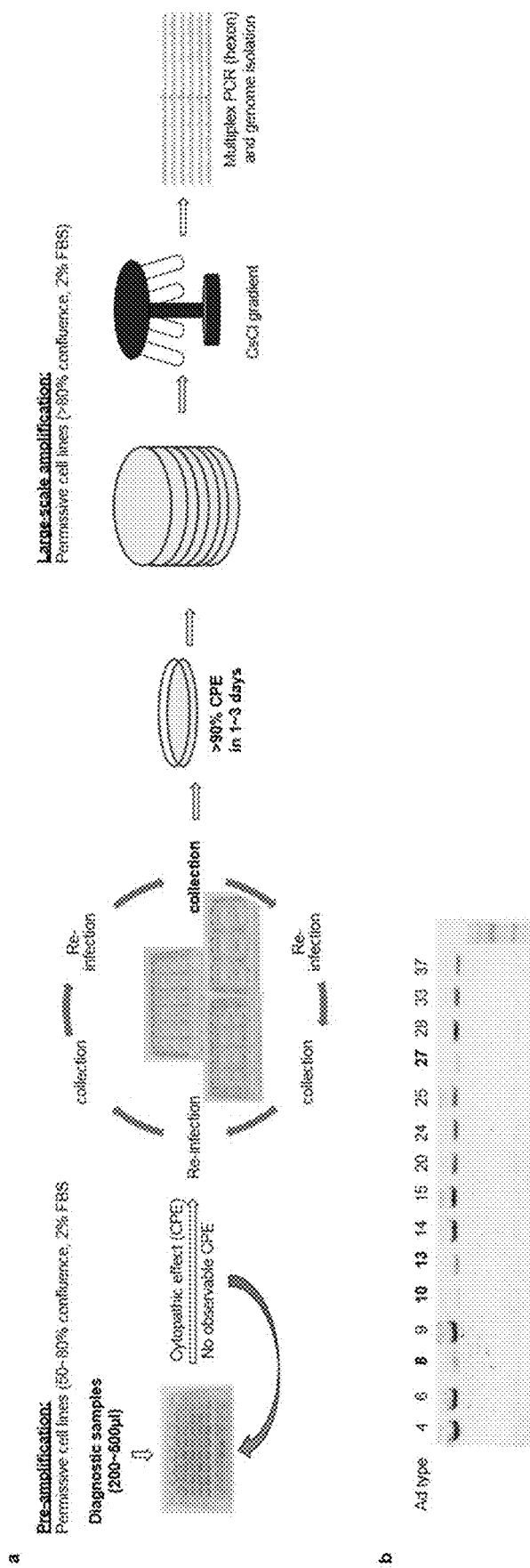
FIG. 1—Schematic outline of wild-type adenovirus amplification and viral genome isolation
a) Wild-type human adenoviruses from clinical isolation were first pre-amplified in individual permissive cell lines (50~80% confluence, 2% FBS) using repeated infection circles to achieve 90% cytopathic effect (CPE). Then each virus was amplified in a large scale manner in 10-20 15 cm tissue culture dishes. Crude cell lysates were used to purify viruses by CsCl gradients, followed by viral genome isolation and sequence verification.

Clinical isolates of wild type (WT) Ad were amplified in permissive cell lines (e.g. HeLa, HEK, A549) using serial amplification steps. After large-scale amplification Ads were purified by cesium chloride gradients (FIG. 1). To verify the Ad type a multiplex hexon-specific PCR was performed and the DNA sequence was confirmed. Viral genomes of purified Ad particles were isolated (FIG. 1) and LLHR was applied to directly clone isolated viral genomes as schematically shown in FIG. 2. We first established a fast and reliable strategy to generate master clones for direct Ad genome cloning based on annealing of 4 PCR fragments in one step. These PCR fragments with homology arms (HA) for directed cloning contained the 5' and 3' ITR sequences, the previously published selection marker ccdB10 and ampicillin for advanced positive and counter selection and the plasmid backbone with a p15A origin of replication and the chloramphenicol resistance gene (FIG. 1). Different ratios of PCR products were tested, and after homologous recombination (HR) in a RecET expressing E. coli strain this resulted into the novel medium copy plasmid p15A-cm-adHA. Equal amounts of all 4 PCR fragments resulted in highest cloning efficiency (FIG. 2b).

Next, isolated linear Ad genomes were cloned into this plasmid using LLHR. FIG. 2c shows recombineering efficiencies of direct viral genome cloning using various amounts of viral DNA (0 to 1 µg) and 1 µg of the linearised shuttle vector. The plasmid backbone for direct cloning of large dsDNA viruses containing the p15A origin of replication results in significantly increased cloning efficiencies and is easier to handle compared to commonly-used bacterial artificial chromosomes (BAC). Since numerous viral genomes show high sequence homologies in their ITR sequences, viral genomes could be cloned simultaneously using the same shuttle vector p15A-cm-adHA containing the same HA. Only 50 bp HA are required, enabling fast and reliable direct HTC. The same strategy was used for Ad from species D, B2 and C.

Integrity of all cloned Ad genomes was checked by diagnostic restriction enzyme digests and compared to originally isolated Ad genomes from virions (FIG. 2). NGS was used to determine exact sequences of all Ad containing plasmids. Extensive rescue experiments were performed and the strategy optimised by testing different molecular forms (precise excision of the Ad genome, linearised Ad containing plasmid and circular Ad genome containing plasmid) (FIG. 3). After introduction of viral DNA into Ad permissive cell lines, viral replication was monitored by quantitative PCR (qPCR) over more than 5 serial passaging steps and the precise excision of the Ad DNA molecule from the plasmid was most sufficient in rescuing Ad. This strategy was then applied to all cloned human Ad.

To further explore the cloned human Ad library, viral genomes were tagged with a 2A peptide-mediated multicistronic-expression cassette (GLN, SEQ ID NO:227) providing a TurboGFP fluorescent protein as an in vitro marker, a NanoLuc luciferase for in vivo studies and kanamycin/neomycin as a selection marker. As schematically outlined in FIG. 3, LCHR was applied for marker insertion into the early gene E3 region of the cloned Ad genomes of the library. In a first step, spectomycin acetyltransferase was inserted via HR in E. coli strain GB05-Red into the adenoviral genome, followed by GLN cloning. By using a conserved region in the E3 region, different Ad genomes could be tagged in a high-throughput manner using the identical shuttle vector for different Ad types (FIG. 4). Tagged Ads were rescued in permissive cell lines.

Tagging of Ad enabled in vitro and in vivo characterisation of chosen Ad types. After infection of cell lines originating from different cell types derived from different organs (epithelium, endothelium, muscle, blood, liver) and measurement of luciferase and GFP expression it was found that tagged Ad show a distinct tropism (FIG. 3). The in vivo tropism was analysed by systemically injected tagged HAdV-B3, HAdV-616, HAdV-650, HAdV-05, and HAdV-E4 into 057Bl/6 mice. As shown in FIG. 3, viruses also showed a distinct biodistribution as detected by transgene expression levels and viral genome level. A summary of the complete pipeline to study natural Ad diversity and to generate an engineered Ad library including tagging of viral genomes is shown in FIG. 5.

Methods for Example 1 and Other Examples

Cell Culture—

Human Hela cells, A549 cells, HEK293, and EA.hy926 cells were grown in high glucose Dulbecco's Modified Eagle's Medium (DMEM, PAN BIOTECH) supplemented with 10% FBS (GE Healthcare), 100 U ml-1 penicillin (PAN-BIOTECH), and 100 µg ml-1 streptomycin (PAN BIOTECH). For human hepatocyte Huh7, Non-Essential Amino Acid (NEAA) was added. For Jurkat cells, RPMI-1640 based Medium supplemented with 10% FBS, 100 U ml-1 penicillin and 100 µg ml-1 streptomycin was used. For the murine cell line Neuro2a (N2a) cells, Eagle's Minimum Essential Medium (EMEM, GE Healthcare), supplemented with 10% FBS, 100 U ml-1 penicillin and 100 µg ml-1 streptomycin was used. For the murine myoblast C2C12 cells, DMEM supplemented with 10% FBS, 100 U ml-1 penicillin and 100 µg ml-1 streptomycin was used.

Wild Type Adenoviruses—

HAdV-05 (ATCC® VR5™) strain and HAdV-F41 (ATCC® VR930™) was obtained from the American Type Culture Collection (ATCC). HAdV-A12, -A18, -A31, -B3, -B16, B21, -B11, -B14, -B35, -C6, -D9, -D10, -D13, -D17, -D20, -D24, -D25, -D26, -D27, -D33, -D37, -D69 and -E4 were clinical isolates obtained from the diagnostic group of the Max von Pettenkofer-Institute (Department of Virology) at the Ludwig-Maximilians-University Munich in Germany. HAdV-B7, -B50, -B34, -C1, -C2, -D8 and -G52 were kindly provided by the Heinrich Pette Institut (HPI) Hamburg, Germany.

Ad Amplification, Purification and Titration—

WT human Ad from clinical isolates were first pre-amplified in individual permissive cell lines (50~80% confluence), with serial infection circles to achieve 90% cytopathic effect (CPE). Each virus was amplified to large scale in 10-20 15 cm tissue culture dishes. For virus amplification DMEM supplemented with 2% FBS was used. Crude cell lysates were used to purify viruses by a CsCl gradient-based ultracentrifugation method (Beckman Coulter), followed by a desalting step based on disposable PD-10 desalting columns (GE Healthcare). The purified virus was aliquoted and stored at −80° C. for further use. Ad particle concentrations were determined by measuring the optical density at 260 nm and expressed as viral particles (VPs) per milliliter.

Adenoviral genomic DNA isolation from virions—

For cloning of viral genomes, viral genomic DNA was extracted from purified particles by the addition of proteinase K, subsequent phenol-chloroform extraction, and ethanol precipitation. A detailed protocol for isolating viral genomic DNA is found in Example 7. To confirm the Ad type on genome level, multiplex PCR and sequencing were performed using the primer pair hexon-fwd (ATGGC-CACCCCATCGATGATGC) (SEQ ID NO: 1452) and hexon-rev (TTATGTGGTGGCGTTGCCGGCC) (SEQ ID NO: 1453) amplifying the hexon regions of the viral genomes. To verify the end-sequence of the adenoviral genome for the following homologous recombineering step, primers reading into the ITR region were designed.

Plasmid Construction— p15A-cm-MCS; p15A-amp-ccdB; pR6K-spect-adapter; pR6K-GLN; Linear-linear homologous recombination (LLHR)-mediated adenoviral genome cloning. Linear-circular homologous recombination (LCHR)-mediated adenovirus genome tagging.

PCR—

Homology arm (HA)-containing long primer-mediated PCR was performed with Phusion® High-Fidelity DNA Polymerase (New England Biolabs, Frankfurt, Germany) according to the manufacture's protocol. Notably, only the primer binding sequence (~20 bp) was used for calculating the annealing temperature. The PCR product purified with the Wizard® SV Gel and PCR Clean-Up System (Promega, Mannheim, Germany) and eluted in ddH2O was used for electroporation. To check virus reconstitution and amplification, OneTaq® 2X Master Mix (New England Biolabs, Frankfurt, Germany) was used according to the manufacture's standard protocol.

NGS and bioinformatics analyses—

For sequencing of plasmids, 200 ng purified DNA was subjected to standard Illumina DNA library preparation. In brief, DNA was enzymatically sheared (NEBnext dsDNA Fragmentase, New England Biolabs). After XP bead purification (Beckman Coulter), ends were polished and A-tailed and universal adapters were ligated (Ultra Directional DNA Library Prep Kit, New England Biolabs). For adapter ligation, custom adaptors were used (Adaptor-Oligo 1: 5'-ACA-CTC-TTT-CCC-TAC-ACG-ACG-CTC-TTC-CGA-TCT-3' (SEQ ID NO: 1454), Adaptor-Oligo 2: 5'-P-GAT-CGG-AAG-AGC-ACA-CGT-CTG-AAC-TCC-AGT-CAC-3' (SEQ ID NO: 1455)). After ligation, adapters were depleted by XP bead purification (Beckman Coulter). Sample indexing was done in the following PCR enrichment (15 cycles). For Illumina flow cell production, samples were equimolar pooled and distributed on two Illumina MiSeq flow cells for 300 bp paired-end sequencing. The Illumina TruSeq adapter and regions of low quality (phred quality <20) were trimmed with cutadapt requiring a minimum length of 50 bp. Trimmed reads were mapped with BWA onto the reference sequence of the vector and reads consisting entirely of vector sequence were discarded whereas reads without or with only partial vector sequence were kept. Each adenovirus dataset was assembled with IVA de novo as well using the respective GenBank sequence as anchor. The better assembly was chosen based on number of sequences, total length and presence of vector sequence at the flanks of the assembled sequence. The remaining vector sequence was identified with BLAT and removed with in-house Perl scripts and the final assembled sequence was orientated according to the respective GenBank reference sequence. Annotation of coding sequences (CDS) was done with Glimmer in two steps. First, known adenovirus CDS from the GenBank were compared to the assembled sequences using exonerate. The resulting alignments served as training set for Glimmer which then predicted the final CDS regions. Functional identification of CDS was based on BLASTP against known adenovirus protein sequences from GenBank. To align and visualize the adenovirus sequences obtained by NGS against their respective GenBank reference sequences, we used the zPicture program (webpage: zpicture.dcode.org/). Sequence alignments between adenovirus sequence and GenBank reference were done with BLASTZ. As cut-off value, we used a minimum sequence identity of 99% which minimizes false-positive alignments but still allows for studying single nucleotide variants between adenovirus sequences and respective GenBank references. Multiple sequence alignments for conserved E3 and ITR sequences were generated using clustal Omega (www.ebi.ac.uk/Tools/msa/clustalo/) with default parameters and for visualized extent of conservation in aligned sequence sets we used WebLogo (webpage: weblogo.berkeley.edu/logo.cgi). Plasmid DNA transfection and virus rescue—10 µg of the p15A-based adenovirus genome containing plasmids were either digested with a combination of two restriction enzymes (PmeI/SbfI or PacI/SwaI) releasing the adenovirus backbone, or with the restriction enzyme I-SceI linearizing the p15A-based Ad genome. To purify and concentrate digested DNA, ethanol precipitation was performed for DNA digested with PmeI/SbfI and PacI/SwaI, and for I-SceI digested DNA a phenol-chloroform extraction followed by ethanol precipitation was conducted.

A549 cells were plated in 6-well plates and at 50-80% confluency 3 µg of digested viral DNA was transfected using Superfect transfection Reagent (Qiagen) according to the manufacturer's protocol. After 24-48 hrs, when the cells grew to up to >90% confluency, the medium was changed to 2% FBS-supplemented DMEM. The cells were maintained for up to two weeks, until cytopathic effect (CPE) was observed. If no CPE was obtained, the cell/virus lysate was collected and ½ or ⅓ of the lysate was used to infect a new well of A549 cells at a confluency of 90-95%. To release the virus from infected cells, the crude lysate was subjected to three freeze/cycles in liquid nitrogen and in a 37° C. water bath. A small aliquot of cells was collected for qPCR analysis.

qPCR Analysis—

To monitor virus replication during rescue, quantitative real-time PCR (qPCR) was performed using the CFX96 Touch™ Real-Time PCR Detection System (Bio-Rad). Previously described primer pairs and probes (Damen, M et al, 2008, JoCM) binding to the hexon of Ad were used to determine the copy number of Ad genomes in infected cells. The PCR was based on the following program: pre-incubation/activation at 95° C. for 5 min, amplification and data collection during 40 cycles (95° C. for 15 s and 60° C. for 30 s). The Sso Fast™ Probes Supermix (Bio-Rad) was used for these PCRs.

Characterization of Tagged Ad In Vitro and In Vivo—

All reconstituted GLN-tagged viruses were confirmed by hexon-PCR of isolated adenoviral genomes. Adenovirus particle concentrations were determined by measuring the optical density at 260 nm and expressed as viral particles (vps) per millilitre.

Nano-Glo Luciferase Assay—

Individual tested cells were grown to confluence in 96-well tissue culture plate and infected with different viral partials (VPs) per cells. 26 h after infection NLuc activity was measured with the Nano-Glo assay system (Promega), and luminescence was detected with a plate reader (Tecan).

Genome Uptake Measured by Internalization Assay—

To quantify the cell entry efficiency, a defined number of Ad particles (vp) was used to infect pre-seeded tumor cells and incubated for 2 hours. Cell monolayers was digested and flushed off with trypsin, followed by extensive washing with PBS. Genomic DNA was extracted by incubation in TE buffer (10 mM Tris-HCl, 10 mM EDTA, pH 8.0) with 0.5% SDS and 0.5 mg/ml proteinase K. Subsequently a phenol-chloroform extraction and ethanol precipitation was performed. To monitor virus genome uptake efficiency, quantitative real-time PCR (qPCR) detecting the transgene (GLN gene cassette) was performed.

Oncolytic Assays with Most Promising Ad Candidates—

Oncolytic assay was performed in 24 well plates. A 10-fold dilution series of individual Ads was prepared freshly to infect pre-seeded cancer cells. Cytopathic effect (CPE) was checked daily until at least one of the viruses on one plate at the lowest dosage showed CPE or until maximal 14 days. The cells were first fixed with 3.7% formaldehyde then stained with crystal violet solution.

Statistics—

Statistical analyses were conducted with Microsoft Excel. Experimental differences were evaluated by a Student's one-tailed t-test assuming equal variance.

Example 2—Gene Annotation

Genes were predicted using Gene Locator and Interpolated Markov ModelER (Glimmer)[38]. For each sequenced genome, protein sequences of known genes of the respective reference from GenBank were aligned with exonerate[39] to the assembled genome sequence. The coordinates of the best hits were then used to build a Glimmer model which was subsequently used for prediction of location and orientation of genes in the sequenced genome.

Next, protein sequences were compared between virus genomes. The result of this analysis is given in FIG. 6. Shown are genome organisations for 28 sequenced human adenoviruses. Genes and their orientation are shown as gray-shaded shapes on both strands of the genome (solid line). All genomes show the canonical organization of the Mastadenovirus genus.

Shading of a gene reflects its maximum sequence divergence across all 28 viruses determined through an all-vs-all Blast analysis.

Example 3—Cell Tropism of Human Adenovirus D17

A new first generation adenovirus based on human adenovirus D17 was constructed and labelled with a green fluorescent protein (GFP) marker using the recombineering technology described in Example 1. The early E1 gene was deleted in the HAdV17 vector, and a corresponding E1-deleted, GFP-labeled HAdV5 vector was constructed for comparison.

Viruses were rescued in complementary E1-expressing stable cell lines, and then screened against a panel of different cell lines by fluorescence activated cell sorting (FACS) analysis and quantitative PCR. HAdV17 was found to have a tropism for endothelial cells, whereas endothelial cells are normally refractory to HAdV5 infection. This finding was further verified using primary human umbilical vein endothelial cells (HUVEC).

Competition assays based on soluble recombinant fiber knob blocking reagents[40, 17] (5knob, 17knob, JO4, Augmab) were used to characterize the receptor interaction with these vectors in vitro. It was found that HAdV17 could utilize both CD46 (a membrane cofactor protein which is expressed on all nucleated cells) and CAR (coxsackievirus and adenovirus receptor) as cell attachment receptors. The endothelial cell tropism was CD46-dependent and could be blocked by the CD46 blocking reagent Augmab.

In vivo biodistribution analyses were performed after intravenous injection of recombinant viruses into both normal and CD46-transgenic mice. These studies showed significantly increased vector genome copies (VCN) in various organs of CD46-transgenic mice compared to normal mice, indicating the involvement of CD46 as a receptor. These results were confirmed by quantitative PCR (qPCR) and immunohistology analysis.

Neutralising antibody assays revealed that there was less seroprevalence with HAdV17 compared to HAdV5 in humans.

Accordingly, HAdV17-based vectors, which can use both hCAR and CD46 as receptors and display an endothelial cell tropism, hold great promise for gene therapy in endothelial disease.

See also FIGS. 11-19.

Example 4—Delivery of all Components of the CRISPR/Cas9 System Using High-Capacity Adenoviral Vectors A new CRISPR/Cas9 shuttle plasmid toolbox was generated, containing the Cas9 nuclease gene, either utilising a constitutive or an inducible promoter, and a gRNA expression unit. The toolbox allows cloning or recombining of all CRISPR/Cas9 components into the HCAdV genome in one step. To use several gRNA expression units for multiplexing the CRISPR/Cas9 system, further gRNA expression units can be easily included. To enable fast assembly of recombinant CRISPR-HCAdV genomes, DNA recombineering was used to introduce all CRISPR/Cas9 expression units into the HCAdV genome contained in the bacterial artificial chromosome pBHCA. For insertion of multiple gRNA expression units into the HCAdV genome, the established pAdV-FTC plasmid was used in concert with homing endonuclease directed cloning. CRISPR-HCAdVs were produced using a shortened amplification and purification procedure.

The toolbox was used to produce several CRISPR-HCAdVs carrying single and multiplex gRNA units specific for different targets including hCCR5, hDMD, and HPV16- and HPV18-E6 genes, yielding sufficient titers within a short time. T7E1 assays[41] were applied to prove CRISPR/Cas9-mediated cleavage of respective targets. Infection of cultured human cells with respective CRISPR-HCAdVs resulted in efficient site-specific gene editing.

In summary, this new platform enables customisation, cloning and production of CRISPR-HCAdV vectors for single or multiplex approaches within a short time. It simplifies the delivery of the CRISPR/Cas9 machinery by only using one single viral vector. Inducible Cas9 expression helps to avoid targeting of the genome of producer cell lines during vector production and may be beneficial for special approaches where constitutive expression is unwanted.

Example 5—Enhanced Oncolytic Activity Mediated by a Novel Human Adenovirus Type 6-Based Vector Most existing oncolytic adenoviruses (AdV) are based on human AdV type 5 (hAdV-5). Clinical efficacy of hAdV-5 based oncolytic viruses is limited by variable expression levels of coxsackie- and adenovirus receptor (CAR) in different tumour cells, and insufficient replication rates. Additionally, high prevalence of neutralising antibodies against hAdV-5, resulting in lower efficiency, makes hAdV-5 a less suitable candidate for systemic application. Recent studies have highlighted human adenovirus type 6 (hAdV-6) as a promising candidate for oncolytic and vaccine vectors. Thus, development of novel oncolytic AdV based on hAdV-6 may help to overcome these limitations. Oncolytic efficacy of the candidate virus can be augmented by expression of RNAi suppressor protein P19, as has been shown previously for hAdV-5[31]. In this example, a novel hAdV-6-based, p19-containing oncolytic AdV was evaluated as a candidate for oncolytic applications in different tumour cell lines.

A P19-containing hAdV-6 based virus (hAdV-6FP19) was cloned by a novel seamless recombineering technique (see Example 1). In order to allow P19 expression from the adenoviral vector genome, the P19 cDNA was fused via an internal ribosome entry site (IRES) to the late fiber gene. After release of the respective recombinant adenoviral genomes from plasmids containing the complete DNA molecule, linearised viral DNA was transfected into HEK 293 cells for virus reconstitution. After initial amplification steps which were monitored by virus specific PCRs, upscaling and virus purification using cesium chloride density gradient ultracentrifugation was performed. Rescue and amplification efficiencies were comparable to commonly used hAdV-5 based vectors.

Various cancer cell lines from different origin were used to perform oncolysis assays. These included: A549 (lung carcinoma), HCT 116 (colon carcinoma), HeLa (cervical carcinoma) and Huh7 (hepatocellular carcinoma). Cells were infected with hAdV-6FP19, hAdV-6 and hAdV-5 at various multiplicities of infection (MOI). Two to three days after infection, cells were fixed and stained with methylene blue. Significantly higher cell lysis (up to 100-fold) was observed for hAdV-6FP19-infected cells as compared to hAdV-5 and 6 at identical MOIs. Higher cell lysis rates for hAdV-6FP19 compared to wildtype virus were present in all evaluated cell lines, suggesting significantly enhanced oncolytic potential for hAdV-6FP19. In summary, hAdV6-based vectors hold great promise for oncolytic applications and their oncolytic effectiveness can be further improved by RNAi suppression.

Example 6—High Throughput Screening (HTS) of Adenovirus Library as a Novel Resource for Disease-Specific Targeting To fully explore our cloned Ad library as a resource for developing of novel translational approaches, the library was further tested on a panel of cell lines using an HTS approach. Cell lines originating from different cell types were infected with the reporter-labelled virus types of the Ad library. Transduction efficiencies measured by luciferase expression levels were compared to the commonly used adenoviral vector type 5 (Ad5). Initial screening revealed that species B adenoviruses have high transduction efficiencies in epithelial (A549, HCT 116, ARPE-19) and endothelial (EA.hy926) cells. While in the liver originated cell lines SK-HEP-1 and Huh-7, the common used vector type 5 (Ad5) highest infection efficiencies (FIG. 20). Also included was an osteosarcoma derived cell line (MG-63) and the breast cancer-derived cell line Hs 578T derived form a triple-negative breast cancer (TNBC). In the TNBC 207 cell line, Ad37 was identified as the most efficient Ad type, while other species B types (Ad16, 50 and 35) revealed improved efficiency compared to the commonly used Ad5 (FIG. 20). After performing HTS on osteosarcoma derived MG-63 cells, it was discovered that Ad21 showed highest transduction efficiencies (FIG. 20).

Therefore, Ad21 was further pursued as a potential oncolytic agent to treat osteosarcoma, because this type of cancer is the most frequent primary cancer of bone which predominantly occurring in the second decade of life. Regarding the age group from 15-19 years, osteosarcomas represent >10% of all solid cancers. Therefore, a panel of osteosarcoma cell lines with different grading related features, including Saos-2 and U-2 OS cells, was further examined.

As displayed in FIG. 21a and in concordance with results obtained in MG-63 cells (FIG. 20), Ad21 was identified as a promising alternative Ad type to transduce osteosarcoma cell lines, which was also confirmed by GFP also expressed form the tagged Ads (FIG. 21b) and by virus internalization assays measuring uptake of virus genomes 3 hrs post-infection (FIG. 21c). The oncolytic potency of selected Ad types was analysed in all three osteosarcoma cells and it was found that Ad21 consistently resulted in efficient oncolysis of respective cell lines at different MOIs tested (FIG. 21d). To show that oncolytic potential varied between different cancer cell lines we also tested the tagged Ad library on lung carcinoma derived A549 cells revealing that in contrast to osteosarcoma cell lines, Ad35 and -69 showed highest oncolytic potency (FIG. 22). This proof-of principle experiment demonstrates that a novel virus candidate for disease specific targeting can be identified by HTS allowing development of novel therapeutic agents in further steps.

Using the same methodology, FIG. 23 shows the high infectivity rates of the Ad5, Ad21 and Ad37 adenoviruses in the glioblastoma derived cell-line RG2 [D74]. This indicates that adenoviral vectors derived from these adenovirus types would be effective in targeting glioblastoma cells.

Example 7—Protocol to Isolate Adenoviral Genomic DNA for Use in the Cloning Step 1. Incubate certain volume of purified virus for 2 hours (or overnight) with proteinase K-SDS solution pH 7.5-8 (TE buffer, 0.5% SDS, 100~500 µg/ml proteinase K) at 56° C., with low speed shake (300 rpm).
2. Add equal volume mixture of phenol:chloroform:isoamyl alcohol (25:24:1) to the sample from step 1. In doing this, go inside to the mixture, and do not take the surface layer. To increase the recovery rate, use a phase lock gel tube (Phase Lock Gel Heavy 1.5 ml, uk.vwr.com/store/product/826754/phase-lock-gel).
3. Centrifuge for 5 min at full speed (15,000 g) at room temperature in a microcentrifuge and then transfer the aqueous phases to another clean eppendorf tubes.
4. Precipitate viral DNA by adding 1/10 volume of 3 M sodium acetate (pH 5), 2 µg glycogen and 2.5~3 times of precooled EtOH (99.8%; stored at −20° C.). Mix gently by inverting the tube several times. To increase the recovery rate, put the mixture in −20° C. for 30 mins.
5. Centrifuge for 10 min at full speed (15,000 g) at room temperature in a microcentrifuge and discard the supernatant by pipetting.
6. Add 600 µl of 70% ethanol and mix gently by inverting the tube several times. After centrifugation at 15,000 g at room temperature for 5 min, remove the supernatant by pipetting.
7. Repeat step 6
8. Air-dry the DNA pellet briefly and resuspend in 20~50 µl of sterilized dH2O low speed shake (300 rpm) at room temperature for 15 mins.

In this protocol, which is provided by way of example, it is important that the large genomic DNA is never vortexed or vigorously pipetted during isolation.

REFERENCES

[1] Aiuti, A. et al. Lentiviral hematopoietic stem cell gene therapy in patients with Wiskott-Aldrich syndrome. Science 341, 1233151, (2013).
[2] Nathwani, A. C. et al. Adenovirus-associated virus vector-mediated gene transfer in hemophilia B. The New England journal of medicine 365, 2357-2365, (2011).
[3] Biffi, A. et al. Lentiviral hematopoietic stem cell gene therapy benefits metachromatic leukodystrophy. Science 341, 1233158, (2013).
[4] Wiley, J. M. Gene Therapy Clinical Trials Worldwide. J. Gene Med., (2015).
[5] Crystal, R. G. Adenovirus: the first effective in vivo gene delivery vector. Human gene therapy 25, 3-11, (2014).
[6] Zabner, J. et al. Adenovirus-mediated gene transfer transiently corrects the chloride transport defect in nasal epithelia of patients with cystic fibrosis. Cell 75, 207-216 (1993).
[7] Wilson, J. M. Gendicine: the first commercial gene therapy product. Human gene therapy 16, 1014-1015, (2005).
[8] Kaufman, H. L., Kohlhapp, F. J. & Zloza, A. Oncolytic viruses: a new class of immunotherapy drugs. Nature reviews. Drug discovery 14, 642-662, (2015).
[9] Hage, E. et al. Human Adenovirus type 70: A novel, multiple recombinant species D adenovirus isolated from diarrheal faeces of a haematopoietic stem cell transplantation recipient. J. Gen. Virol. 96, 2734-2742, (2015).
[10] Davison, A. J., et al. Genetic content and evolution of adenoviruses. J. Gen. Virol. 84, 2895-2908, (2003).
[11] Fu, J. et al. Full-length RecE enhances linear-linear homologous recombination and facilitates direct cloning for bioprospecting. Nature biotech. 30, 440-446, (2012).
[12] Wang, H. et al. Improved seamless mutagenesis by recombineering using ccdB for counterselection. Nucleic acids research 42, e37, (2014).
[13] Harrach, B. et al. Adenoviridae. In "Virus Taxonomy" (ed. King, A. M. Q., Adams, M. J., Carstens, E. B. and Lefkowitz, E. J.), 125-141 (Elsevier, 2011).
[14] Bradley, R R. et al. Adenovirus serotype 5 neutralizing antibodies target both hexon and fiber following vaccination and natural infection. J. Virol. 86, 625-629, (2012)
[15] Zhang, Y. and Bergelson, J. M. Adenovirus receptors. J. Virol. 79, 12125-12131, (2005).
[16] Ghebremedhin, B. Human adenovirus: viral pathogen with increasing importance. Eur. J. Microbiol. Immunol. 4, 26-33, (2014).
[17] Wang, H. et al. Desmoglein 2 is a receptor for adenovirus serotypes 3, 7, 11 and 14. Nat. Med. 17, 96-105, (2011)
[18] Tuve, S. et al. A new group B adenovirus receptor is expressed at high levels on human stem and tumor cells. J. Virol. 80, 12109-12120, (2006).
[19] Danthinne, X. and Imperiale, M J. Production of first generation adenovirus vectors: a review. Gene Ther. 7, 1707-1714, (2000).
[20] WO 2011/154927
[21] Cong, L. et al. Multiplex Genome Engineering using CRISPR/Cas Systems. Science 15, 819-823, (2013).
[22] Li, X. et al. PiggyBac transposase tools for genome engineering. Proc. Nat. Acad. Sci. USA 110, E2279-E2287, (2013).
[23] Hausl, M. et al. Development of Adenovirus Hybrid Vectors for Sleeping Beauty Transposition in Large Mammals. Curr. Gene Ther. 11, 363-374, (2011).
[24] Penaloza-MacMaster, P. Alternative serotype adenovirus vaccine vectors elicit memory T cells with enhanced anamnestic capacity compared to Ad5 vectors. J. Virol. 87, 1373-1384, (2013).
[25] Wold, W. S. M. and Toth, K. Adenovirus vectors for gene therapy, vaccination and cancer gene therapy. Curr. Gene Ther. 13, 421-433 (2013).

[26] Barouch, D. H. Novel adenovirus vector-based vaccines for HIV-1. Curr. Opin. HIV AIDS 5, 386-390, (2010)

[27] Geisbert, T. W. et al. Recombinant adenovirus serotype 26 (Ad26) and Ad35 vaccine vectors bypass immunity to Ad5 and protect nonhuman primates against Ebolavirus challenge. J. Virol. 85, 4222-4233, (2011).

[28] Barnes, E. et al. Novel adenovirus-based vaccines induce broad and sustained T cell responses to HCV in man. Sci. Transl. Med. 4, 115ra1, (2012)

[29] Yamamoto, M. and Curiel, D. T. Current issues and future directions of oncolytic adenoviruses. Mol Ther. 18, 243-250, (2010).

[30] Cheong, S. C. et al. E1A-expressing adenoviral E3B mutants act synergistically with chemotherapeutics in immunocompetent tumor models. Cancer Gene Ther. 15, 40-50, (2008).

[31] Rauschhuber, C. et al. RNAi suppressor P19 can be broadly exploited for enhanced adenovirus replication and microRNA knockdown experiments. Sci. rep. 3, 1363 (2013).

[32] Rodriguez, R. et al. Prostate attenuated replication competent adenovirus (ARCA) CN706: a selective cytotoxic for prostate-specific antigen-positive prostate cancer cells. Cancer Res. 57, 2559-2563, (1997).

[33] Cody, J. J. and Douglas, J. T. Armed replicating adenoviruses for cancer virotherapy. Cancer Gene Ther. 16, 473-488, (2009).

[34] Green, N. K. et al. Extended plasma circulation time and decreased toxicity of polymer-coated adenovirus. Gene Ther. 11, 1256-1263, (2004).

[35] Doronin, K. et al. Chemical modification with high molecular weight polyethylene glycol reduces transduction of hepatocytes and increases efficacy of intravenously delivered oncolytic adenoviruses. Hum. Gene Ther. 20, 975-988, (2009).

[36] WO 2009/104094

[37] Wang, H. et al. Improved seamless mutagenesis by recombineering using ccdB for counterselection. Nucleic Acids Res. 42, e37, (2014)

[38] Salzberg, S. L. et al. Microbial gene identification using interpolated Markov models. Nucleic Acids Research 26, 544-548, (1998)

[39] Slater, G. and Birney, E. Automated generation of heuristics for biological sequence comparison. BMC Bioinformatics 6, 31, (2005)

[40] Gaggar, A. et al. CD46 is a cellular receptor for group B adenoviruses. Nat. Med. 9, 1408-1412 (2003).

[41] Mashal R. D. et al. Detection of mutations by cleavage of DNA heteroduplexes with bacteriophage resolvases. Nat. Genet. 9, 177-183, (1995).

SEQUENCE LISTING

The patent contains a lengthy sequence listing. A copy of the sequence listing is available in electronic form from the USPTO web site (https://seqdata.uspto.gov/?pageRequest=docDetail&DocID=US11866724B2). An electronic copy of the sequence listing will also be available from the USPTO upon request and payment of the fee set forth in 37 CFR 1.19(b)(3).

The invention claimed is:

1. A method for cloning an adenoviral sequence, wherein the adenoviral sequence is a full length adenoviral genome sequence, comprising:
   a) providing a first linear nucleic acid molecule which comprises the full length adenoviral genome sequence;
   b) providing a linearized medium copy plasmid which shares at least two regions of sequence homology with the first linear nucleic acid molecule; and
   c) bringing the first linear nucleic acid molecule and the linearized medium copy plasmid into contact in the presence of a 5' to 3' exonuclease and an annealing protein such that the first linear nucleic acid molecule and the linearized medium copy plasmid recombine to form a circular plasmid containing the full length adenoviral genome sequence;
   wherein the 5' to 3' exonuclease is full length RecE of SEQ ID NO:1412, or a protein with at least 95% sequence identity to SEQ ID NO:1412, and the annealing protein is RecT,
   and wherein a first region of the at least two regions of sequence homology is a region of sequence homology with the 5' ITR of the adenoviral sequence in the first linear nucleic acid molecule, and a second region of the at least two regions of sequence homology is a region of sequence homology with the 3' ITR of the adenoviral sequence in the first linear nucleic acid molecule, and wherein each of the first region and the second region is 40-80 nucleotides in length.

2. The method of claim 1, wherein the first linear nucleic acid molecule is present in a mixture.

3. The method of claim 1, wherein the linearized medium copy plasmid is a p15A origin-based vector.

4. The method of claim 1, further comprising the generation of an adenoviral vector from the circular medium-copy plasmid comprising the full length adenoviral genome sequence, comprising:
   a) providing a second linear nucleic acid molecule which shares at least two regions of sequence homology with the circular medium-copy plasmid comprising the full length adenoviral genome sequence, wherein the second linear nucleic acid molecule comprises one or more transgenes of interest situated between two regions of sequence homology; and
   b) bringing the circular medium-copy plasmid comprising the full length adenoviral genome sequence and the second linear nucleic acid molecule into contact in the presence of a 5' to 3' exonuclease and an annealing protein such that sequences between the regions of homology in the second linear nucleic acid molecule are introduced into the circular medium-copy plasmid;
   wherein:
   i) the 5' to 3' exonuclease is RecE and the annealing protein is RecT; or ii) the 5' to 3' exonuclease is Red alpha and the annealing protein is Red beta.

5. The method of claim 4, further comprising a step of releasing the adenoviral vector in linear form from the circular medium copy plasmid.

6. The method of claim 4, wherein the one or more transgenes include one or more reporter genes.

7. The method of claim 6, wherein the one or more reporter genes include one or more genes encoding a fluorescent protein and/or a luciferase gene.

8. The method of claim 1, further comprising a step of creating a library comprising two or more medium copy plasmids each comprising a full length adenoviral genome sequence.

9. The method of claim 8, wherein the cloned adenoviruses in the library are tagged with one or more reporter genes.

10. The method of claim 9, wherein the one or more reporter genes include one or more genes encoding a fluorescent protein and/or a luciferase gene.

* * * * *